United States Patent [19]
Wong

[11] Patent Number: 5,614,615
[45] Date of Patent: Mar. 25, 1997

[54] SIALYL LEWIS X MIMETICS INCORPORATING FUCOPEPTIDES

[75] Inventor: Chi-Huey Wong, Rancho Santa Fe, Calif.

[73] Assignee: The Scripps Research Institute, La Jolla, Calif.

[21] Appl. No.: 519,203

[22] Filed: Aug. 25, 1995

Related U.S. Application Data

[63] Continuation-in-part of Ser. No. 407,912, Mar. 21, 1995.

[51] Int. Cl.$^6$ .......................... C07K 9/00; A61K 31/70; A61K 38/14; C07H 15/00
[52] U.S. Cl. ....................... 536/17.9; 536/29.1; 530/322
[58] Field of Search ............................... 536/17.9, 29.1; 530/322; 514/2, 25, 42

[56] References Cited

U.S. PATENT DOCUMENTS

| | | | |
|---|---|---|---|
| 3,871,958 | 3/1975 | Nakazawa et al. | 435/106 |
| 5,079,353 | 1/1992 | Ratcliffe et al. | 536/53 |
| 5,143,712 | 9/1992 | Brandley et al. | 424/1.73 |
| 5,296,594 | 3/1994 | Ratcliffe et al. | 536/53 |
| 5,508,387 | 4/1996 | Tang et al. | 530/403 |

FOREIGN PATENT DOCUMENTS

WO91/19501  12/1991  WIPO.
WO91/19502  12/1991  WIPO.

OTHER PUBLICATIONS

Allanson, et al., "A Novel Mimic of the Sialyl Lewis X Determinant" *Tetrahedron Lett.*, 34: 3945–3948 (1993).
Ball, et al., "Synthesis and Structural Analysis Using 2–D NMR of Sialyl Lewis X (Sle) and Lewis X (Le) Oligosaccharides: Ligands Related to E–Selectin (ELAM–1) Binding", *J. Am. Chem. Soc.*, 114: 5449–5451 (1992).
Brandley, et al., "Structure–Function Studies on Selectin Carbohydrate Ligands. Modifications to Fucose, Sialic Acid and Sulphate as a Sialic Acid Replacement", *Glycobiology*, 3:633–639 (1993).
DeFrees, et al., "Ligand Recognition by E–Selectin: Analysis of Conformation and Activity of Synthetic Monomeric and Bivalent Sialyl Lewis X Analogs", *J. Am. Chem. Soc.*, 115: 7549–7550 (1993).
DeFrees, et al., "Ligand Recognition by E–Selectin: Synthesis, Inhibitory Activity, and Conformational Analysis of Bivalent Sialyl Lewis X Analogs", *J. Am. Chem. Soc.*, 117: 66–79 (1995).
Giannis, "The Sialyl Lewis X Group and its Analogues as Ligands for Selectins: Chemoenzymatic Synthesis and Biological Functions", *Angew. Chem. Int. Ed. Engl.* 33: 178–180 (1994).

Graves, et al., "Insight into E–Selectin/Ligand Interaction from the Crystal Structure and Mutagenesis of the lec/EGF Domains", *Nature*, 367: 532–538 (1994).
Hanessian, et al., "A Novel Asymmetric Synthesis of Alpha–and Beta–Amino Aryl Phosphonic Acids", *Synlett*, 868:35–36 (1993).
Huang, et al., "Synthesis of Biologically Active Sialyl Lewis X Mimetics", *J. Org. Chem.*, 60: 3100–3106 (1995).
Ichikawa, et al., "Chemical Enzymatic Synthesis and Conformational Analysis of Sialyl Lewis X and Derivatives", *J. Am. Chem. Soc.*, 114: 9283–9298 (1992).
Lin, et al., "Conformational Studies of Sialyl Lewis X in Aqueous Solution", *J. Am. Chem. Soc.*, 114: 5452–5454 (1992).
Mulligan, et al., "Protective Effects of Oligosaccharides in P–Selectin–Dependent Lung Injury", *Nature*, 364: 149–151 (1993).
Narasinga Rao, et al., "Sialyl Lewis X Mimics Derived from a Pharmacophore Search are Selectin Inhibitors with Anti-–Inflammatory Activity", *J. Biol. Chem.*, 269: 19663–19666 (1994).
Nelson, et al., "Higher–Affinity Oligosaccharide Ligands for E–Selectin", *J. Clin. Invest.*, 91: 1157–1166 (1993).
Prodger, et al., "Synthesis of a Novel Analogue of Sialyl Lewis X", *Tetrahedron Lett.*, 36: 2339–2342 (1995).
Ragan, et al., "Synthesis of a Galactose–Fucose Disaccharide Mimic of Sialyl Lewis X", *Bioorganic Med. Chem. Lett.*, 4: 2563–2566 (1994).
Ramphal, et al., "Structure–Activity Relationships of Sialyl Lewis–X–Containing Oligosaccharides. 1. Effect of Modifications of the Fucose Moiety" *J. Med. Chem.*, 37: 3459–3463 (1994).
Tyrrell, et al., "Structural Requirements for the Carbohydrate Ligand of E–Selectin", *Proc. Natl. Acad. Sci., USA*, 88: 10372–10376 (1991).
Uchiyama, et al., "Design and Synthesis of Sialyl Lewis X Mimetics", *J. Am. Chem. Soc.*, 117: 5395–5396 (1995).

*Primary Examiner*—Gary L. Kunz
*Assistant Examiner*—Kathleen Kahler Fonda
*Attorney, Agent, or Firm*—Donald G. Lewis

[57] ABSTRACT

Sialyl Lewis X mimetics incorporating fucopeptides are synthesized and shown to mimic the configuration and essential functional groups of sialyl Lewis X in space. The fucopeptides exhibit substantially the same biological activity as sialyl Lewis X in the E-selectin binding assay and can be employed for blocking neutrophil inflammatory conditions.

18 Claims, 18 Drawing Sheets

29

IC$_{50}$ = 6mM

32

$IC_{50} = 7mM$

37

IC$_{50}$ = 1.5 mM (2S, 3R)

37

$IC_{50} = 1.5$ mM (2S, 3R)

37

$IC_{50} = 5.0$ mM, (2S, 3S)

46a, R = Et: IC$_{50}$ = 0.5 mM

56

$IC_{50} = 5.0$ mM $IC_{50} = 0.065$ mM $IC_{50} = 0.065$ mM $IC_{50} = 0.9$ mM

68

$IC_{50} = 0.50$ mM

IC$_{50}$ = inactive up to 10 mM

SIALYL LEWIS X MIMETICS INCORPORATING FUCOPEPTIDES

STATEMENT OF GOVERNMENT RIGHTS

This invention was made with government support under Grant No. CHE-9310081 awarded by the National Science Foundation. The U.S. Government has certain rights in the invention.

CROSS-REFERENCE TO RELATED APPLICATION

The present application is a continuation-in-part of U.S. copending patent application Ser. No. 08/407,912, filed Mar. 21, 1995, whose disclosures are incorporated herein by reference.

TECHNICAL FIELD

The present invention relates to compounds that inhibit cellular adhesion. More particularly, the present invention relates to sialyl Lewis X mimetics which incorporate fucopeptides and which mimic the inhibition of selectin-mediated cellular adhesion by sialyl Lewis X.

BACKGROUND

Sialyl Lewis X ($SLe^x$) is a cell surface carbohydrate ligand found on neutrophils, anchored onto the outer membrane thereof by integral membrane glycoproteins and/or glycolipids. $SLe^x$ mediates binding of neutrophils to vascular endothelial cells by binding to E-selectin. (M. Phillips, et al., *Science.* 1990, 250, 1130.; J. Lowe, et al, *Cell.* 1990, 63, 475; T. Feizi, *Trends. Biochem. Sci.* 1991, 16, 84; M. Tiemeyer., et al., *Proc. Natl. Acad. Sci. U.S.A.* 1991, 88, 1138; L. Lasky. *Science.* 1992, 258, 964; and T. Springer, L. A. Lasky, *Nature* 1991, 349, 196.) E-selectin is a cell surface protein inducibly expressed in endothelial cells in response to inflammatory factors such as interleukin Iβ(IL-Iβ) and tumor necrosis factor α (TNFα), leukotriene $B_4$, neurotoxins and bacterial endotoxins, e.g., lipopolysaccharides. These compounds augment polymorphonuclear leukocyte (neutrophil), and monocyte adhesion. Binding of neutrophils to endothelial cells is observed at an early stage after tissue injury and is associated with various acute and chronic inflammations. Neutrophil-mediated inflammatory diseases may be treated by administration of $sLe^x$. Administration of $sLe^x$ inhibits the $sLe^x$/E-selectin interaction and blocks adhesion of neutophils to endothelial cells. (M. Buerke, et al., *J. Clin. Invest.*, 1994, 1140.)

In addition to binding to neutrophils, vascular endothelial cells play key roles in a number of biological responses by selectively binding certain cells, for instance phagocytic leukocytes, in the bloodstream. For example, endothelial cells preferentially bind monocytes and granulocytes prior to their migration through the blood vessel wall and into surrounding tissue in an inflammatory response.

Certain inflammation-triggering compounds are known to act directly on the vascular endothelium to promote the adhesion of leukocytes to vessel walls. Cells then move through the walls and into areas of injury or infection.

Cellular adhesion to vascular endothelium is also thought to be involved in tumor metastasis. Circulating cancer cells apparently take advantage of the body's normal inflammatory mechanisms and bind to areas of blood vessel walls where the endothelium is activated.

Blood platelets are also involved in similar responses. Platelets are known to become activated during the initiation of hemostasis and undergo major morphological, biochemical, and functional changes (e.g., rapid granule exocytosis, or degranulation), in which the platelet alpha granule membrane fuses with the external plasma membrane. As a result, new cell surface proteins become expressed that confer on the activated platelet new functions, such as the ability to bind both other activated platelets and other cells. Activated platelets are recruited into growing thrombi, or are cleared rapidly from the blood circulation. Activated platelets are known to bind to phagocytic leukocytes, including monocytes and neutrophils. Examples of pathological and other biological processes that are thought to be mediated by this process include atherosclerosis, blood clotting and inflammation.

Specialized cell surface receptors on endothelial cells and platelets, designated E-selectin (endothelial leukocyte adhesion molecule-1; ELAM-1 ) and P-selectin (granule membrane protein-140; GMP-140), respectively, are involved in the recognition of various circulating cells by the endothelium and platelets. For example, E-selectin has been shown to mediate endothelial leukocyte adhesion, which is the first step in many inflammatory responses. Specifically, E-selectin binds human neutrophils, monocytes, eosinophils, certain T-lymphocytes, NK cells, and the promyelocytic cell line HL-60.

P-selectin (also known as GMP-140 and PADGEM) is present on the surface of platelets and endothelial cells, where it mediates platelet-leukocyte and endothelium-leukocyte interactions. Thus, for example, activated platelets that express P-selectin on their surface are known to bind to monocytes and neutrophils, and also to bind monocyte-like cell lines, e.g., HL-60 and U937.

P-selectin is an alpha granule membrane protein of molecular mass 140,000 that is expressed on the surface of activated platelets upon platelet stimulation and granule secretion. It is also found in megakaryocytes within the Weibel-Palade bodies. Furie et al., U.S. Pat. No. 4,783,330, describe monoclonal antibodies reactive with P-selectin.

A third receptor is the lymphocyte homing receptor, MEL-14 antigen or its human counterpart LAM-1 (L-selectin). In addition to lymphocyte homing, MEL-14 antigen/LAM-1 is believed to function early in neutrophil binding to the endothelium.

The term "selectin" has been suggested for a general class of receptors, which includes E-selectin (ELAM-1), P-selectin (GMP-140) and L-selectin (MEL-14), because of their lectin-like domain and the selective nature of their adhesive functions. The structure and function of selectin receptors has been elucidated by cloning and expression of full length cDNA encoding each of the above receptors.

The extracellular portion of selectins can be divided into three segments based on homologies to previously described proteins. The N-terminal region (about 120 amino acids) is related to the C-type mammalian lectin protein family as described by Drickamer, *J. Biol. Chem.*, 263:9557–9560 (1988) that induces low affinity IgE receptor CD23. A polypeptide segment follows, which has a sequence that is related to proteins containing the epidermal growth factor (EGF) motif. Lastly, after the EGF domain are one or more tandem repetitive motifs of about 60 amino acids each, related to those found in a family of complement regulatory proteins.

U.S. Pat. No. 5,079,353 and its divisional U.S. Pat. No. 5,296,594 teach the synthesis and use of the sialyl Lewis X (sialyl Le$^x$ or SLe$^x$) and sialyl Lewis A (sialyl Le$^a$ or Sle$^a$) antigens that are present in cancerous tissues, and are ligands for the before-described selectin receptors. U.S. Pat. No. 5,143,712 teaches the binding interactions between various receptors such as ELAM-1 (E-selectin) and ligands such as sialyl Le$^x$ as well as ligands containing a plurality of N-acetyllactosamine (LacNAc) units along with a terminal sialyl group and one or more fucosyl groups that are bonded to the GlcNAc portion of a LacNAc unit.

Published International application WO 91/19501 and WO 91/19502 disclose that oligosaccharides containing the pentameric and hexameric structures shown below inhibited selective cellular binding between cells containing the ligand (below) and those containing a selectin receptor, and that the penta- and hexasaccharides assayed provided better inhibition than did SLe$^x$.

NeuAcα2→3Galβ1→4(Fucα1→3)GlcNAcβ1,3Galβ—;
NeuAcα2→3Galβ1→4(Fucα1→3)GlcNAcβ1,3Galβ1, 4Glc—; and
NeuAcα2→3Galβ1→4(Fucα1→3)GlcNAc=Sle$^x$.

Mulligan et al., *Nature*, 364; 149–151 (1993) reported upon the in vivo effects of Sle$^x$ and a pentamer such as that above present as a —O(CH$_2$)$_5$CO$_2$CH$_3$ glycoside in a neutrophil/P-selectin-dependent rat model. Those authors found that intravenous infusion of up to 200 μg of SLe$^x$ or the pentamer dramatically reduced lung injury and diminished tissue accumulation of neutrophils in rats that received an intravenous infusion of cobra venom. Based on the concentrations used, 200 μg, the effective intravenous concentration of SLe$^x$ was calculated to be less than 1 μM.

DeFrees et al., *J. Am. Chem. Soc.*, 117:66–79 (1995) reported on the in vitro inhibition of binding between E-selectin and SLe$^x$-bearing HL-60 cells for a number of SLe$^x$-related materials including SLe$^x$ itself, an ethyl glycoside of the above pentamer and a number of bivalent SLe$^x$ analogs. Those authors noted that although the affinity of SLe$^x$ for E-selectin is relatively weak in vitro, the IC$_{50}$ value in vivo for protecting against lung injury in rats was in the 1 μM range.

Although SLe$^x$ has been considered to be potentially useful as anti-inflammatory agent and its synthesis on large scales has been developed for clinical evaluation, this natural saccharide can only be used as an injectable form in cases presenting with acute symptoms as it is orally inactive and unstable in the blood stream, because of glycosidase reductions.

The search for novel SLe$^x$ mimetics with simpler structure, higher affinity for the receptor, and better stability against glycosidases, especially fucosidase and sialidase, has been of current interest. A sLe$^x$ mimetic is a compound which includes the functional groups of sLe$^x$ and which mimics the active conformation of sLe$^x$ in space, but which lacks one or more of the glycosidic bonds of sLe$^x$ and/or one or more of the saccharide subunits or analogs thereof. Several active sLe$^x$ mimetics and sLe$^x$ analogs have been designed and synthesized, e.g., a) Allanson, et al., *Tetrahedron Lett*, 34:3945 (1993), 3945 (30-fold less active than SLe$^x$); b) Ragan, et al., *Bioorg. Med. Chem. Lett*, 4:2563 (1994) (a mixture of 4 diastereomers with 40- to 50-fold less activity); c) Hanessian, et al., *Synlett*, 868 (1993) (inactive); and d) H. Huang and C.-H. Wong. *J. Org. Chem.* 1995, 60, 3100; J. C. Prodger, et al. *Tetrahedron Left.* 1995, 36, 2339; and B. N. Narasinga Rao,. *J. Biol. Chem.* 1994, 269, 19663. Two sLe$^x$ mimetics synthesized by Uchiyama et al. are of particular note because they exhibit activities similar to sLe$^x$ in the E-selectin binding assay. (T. Uchiyama, et al. *J. Am. Chem. Soc.* 1995, 117, 5395.) For active natural products inhibiting E-selectin, see Narasinga Rao, et al., *J. Biol. Chem.*, 269:19663 (1994).

The key structural features of sLe$^x$ required for recognition by E-selectin have been determined by structural and conformational studies and by comparative studies of the blocking activity of sLe$^x$ analog families. (B. Brandley, *Glycobiology* 1993, 3, 633; S. DeFrees, *J. Am. Chem. Soc.* 1993, 115, 7549; J. Ramphal, *J. Med. Chem.* 1994, 37, 3459; D. Tyrrell, *Proc. Natl. Acad. Sci. USA* 1991, 88, 10372; R. Nelson,. *J. Clin. Invest.* 1993, 91, 1157; and A. Giannis, *Angew. Chem. Int. Ed. Engl.* 1994. 33. 178.) The solution conformation of sLe$^x$ has been characterized using physical methodologies. (Y. C. Lin, et al., *J. Am. Chem. Soc.* 1992, 114, 5452; Y. Ichikawa, et al. *J. Am. Chem. Soc.*, 1992, 114, 9283; and G. E. Ball et al., *J. Am. Chem. Soc.*, 1992, 114, 5449.) The three-dimensional structure of the human E-selectin has been characterized by X-ray diffraction. (B. J. Graves, et al., *Nature*, 1994, 367, 532.) It has been found that the L-fucose, D-galactose (Gal) and sialic acid moieties of sLe$^x$ are the major components that interact with E-selectin. N-acetylglucosamine unit appears to act merely as a linker to connect L-fucose and sialyl galactose. The six functional groups of sLe$^x$ molecule including the 2-, 3- and 4-OH groups of L-fucose, the 4- and 6-OH groups of Gal and the —CO; group of sialic acid are essential for E-selectin recognition, as illustrated in FIG. 1.

Although sLe$^x$ and active sLe$^x$ analogs can be employed as anti-inflammatory agents, these tetrasaccharides can only be used in acute symptoms as they are unstable in the blood and orally inactive. In addition, it is generally difficult to synthesize oligosaccharides on a large-scale. The use of sLe$^x$ mimetics can obviate the above problems associated with sLe$^x$ analogs. Unfortunately, sLe$^x$ mimetics generally have low activity. What are needed are sLe$^x$ mimetics which are more stable as compared to sLe$^x$ and sLe$^x$ analogs; which possess better bioavailability as compared to sLe$^x$ and sLe$^x$ analogs; which are easier to synthesize than sLe$^x$ and sLe$^x$ analogs; and which exhibit greater activity as compared to known sLe$^x$ mimetics.

SUMMARY OF THE INVENTION

The invention is directed to sLe$^x$ mimetics which incorporate fucopeptides. One subgenus of the invention employs a cyclohexane bridge between the fucose subunit and the peptide moiety. A second subgenus of the invention employs a branched alkyl bridge between the fucose subunit and the peptide moiety. The first subgenus may be represented by compounds of the following formula:

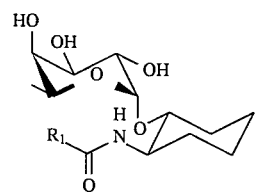

wherein $R_1$ is selected from the following group:

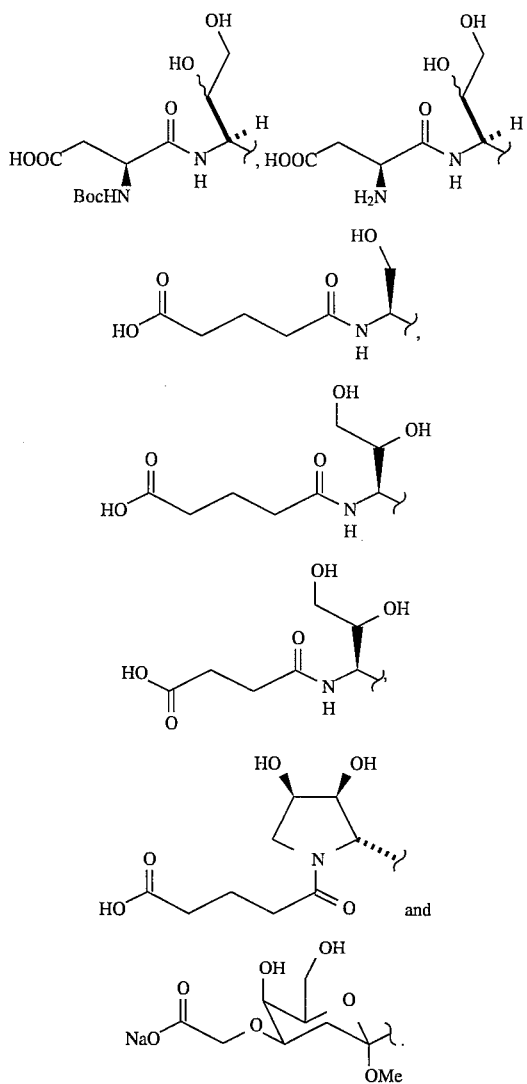

The second subgenus may be represented by compounds of the following formula:

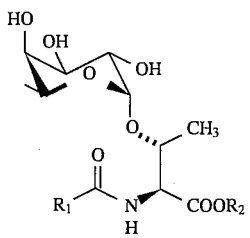

wherein $R_2$ is selected from the group consisting of hydrogen and alkyl groups (C1–C6) and $R_1$ is selected from the following group:

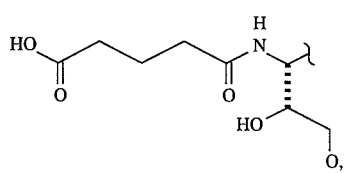

-continued

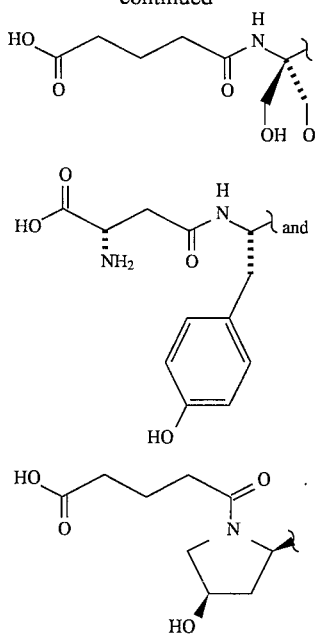

DETAILED DESCRIPTION

Figure 1A:
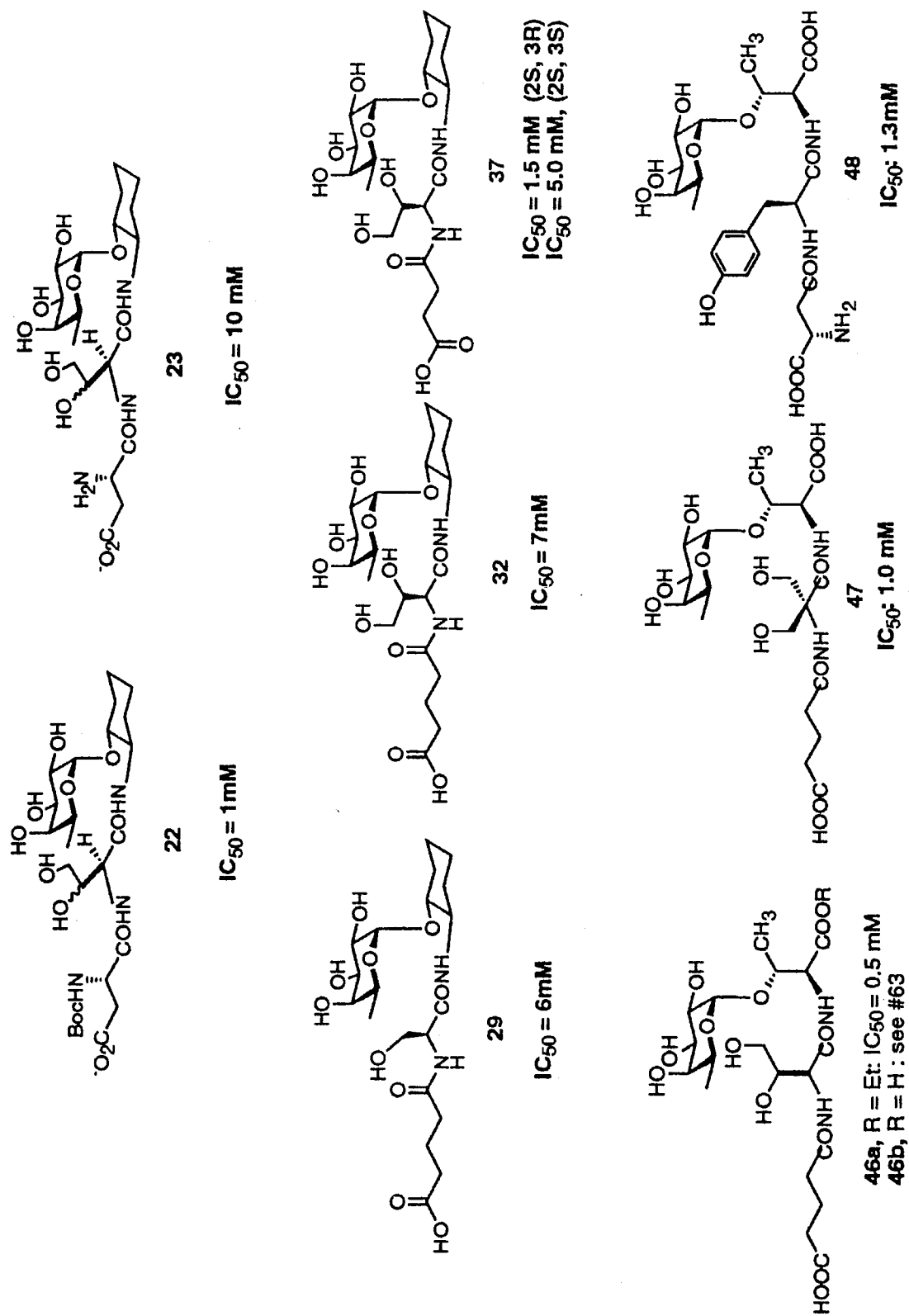
FIG. 1 illustrates the structure of Sialyl Lewis X ($SLe^x$) and its E-selectin Binding domain. The Sialyl Lewis X mimetics 46a, 46b, 47 and 48 are also depicted.
Figure 1B:
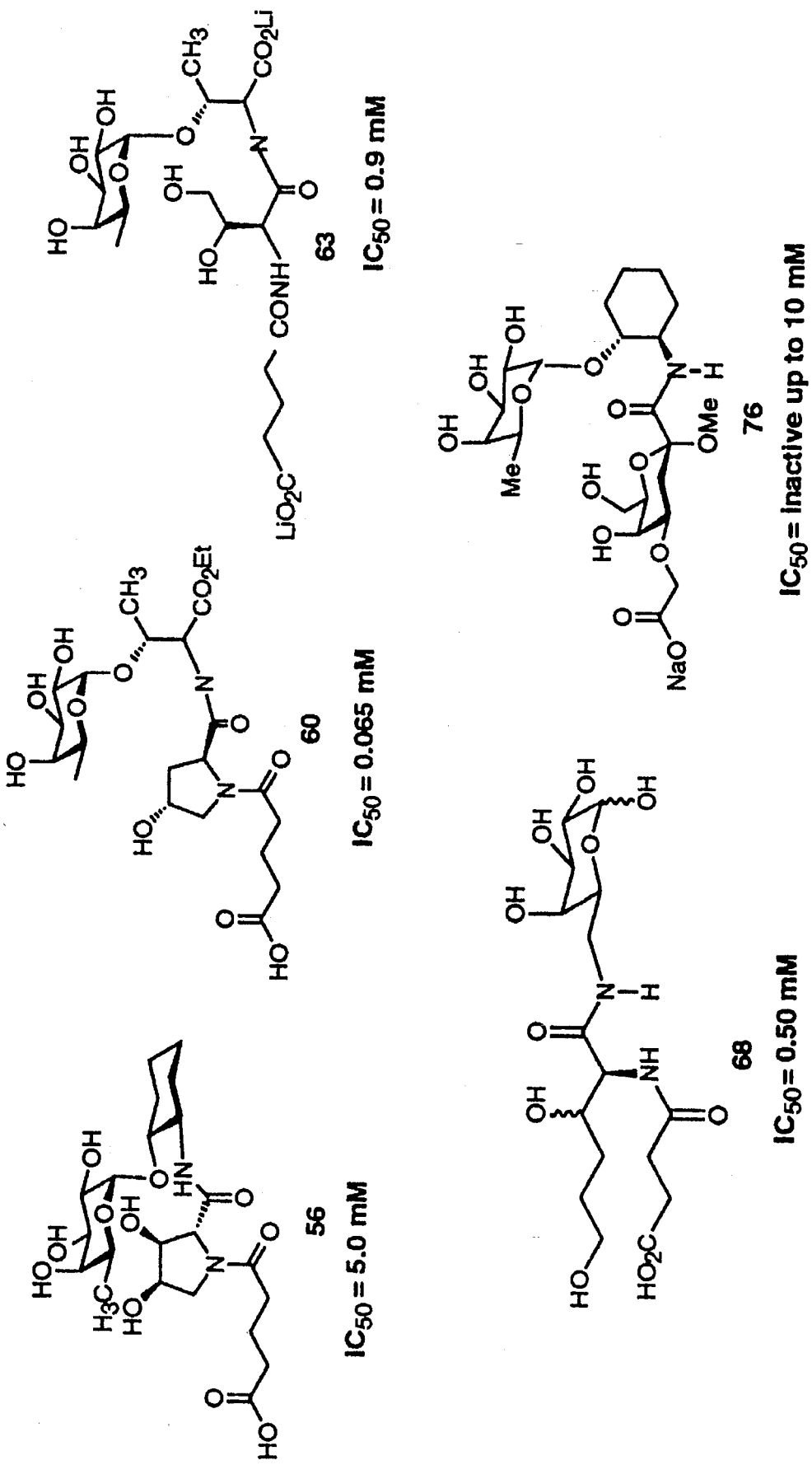
Figure 2:
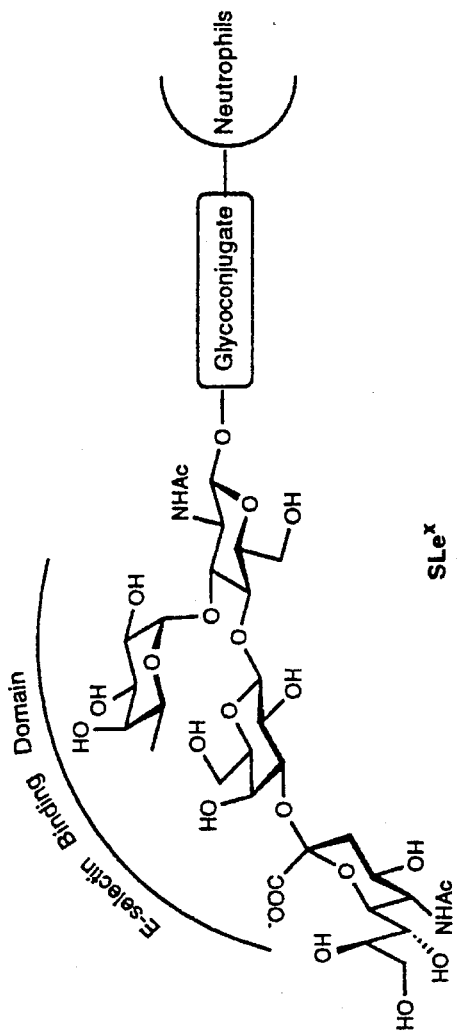
FIG. 2 illustrates the structure of the active mimetics and lists each $IC_{50}$ value.
Figure 2:
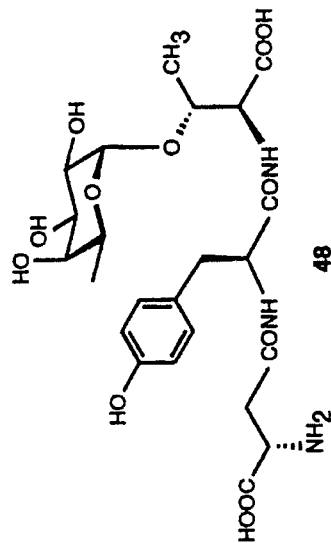
Figure 2:
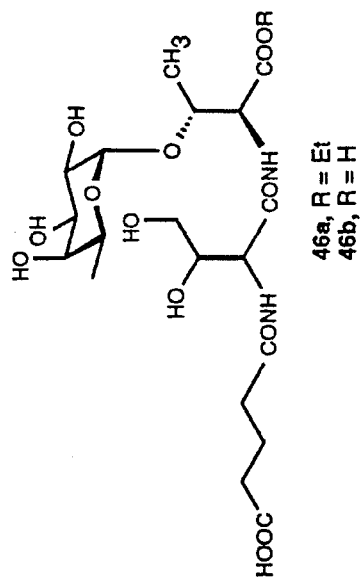
Figure 2:
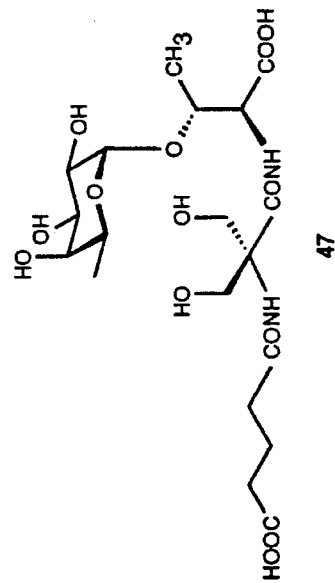
Figure 3A:
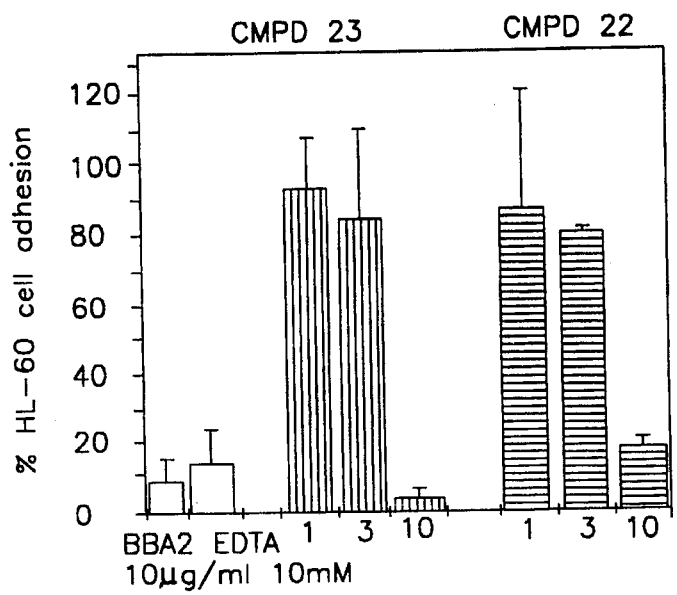
FIGS. 3A and 3B illustrate the HL-60/E-selectin flat-BOTTOM adhesion binding assay for compounds 22 and 23.
Figure 3B:
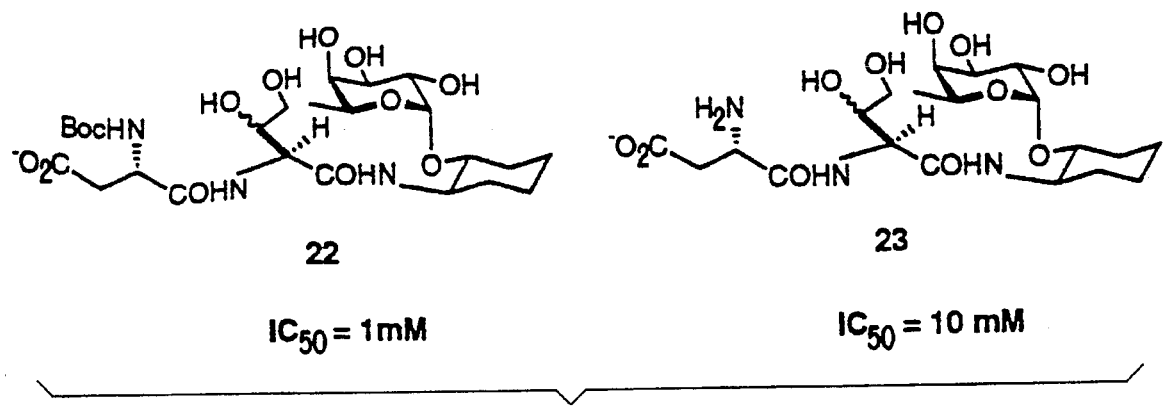
Figure 4A:
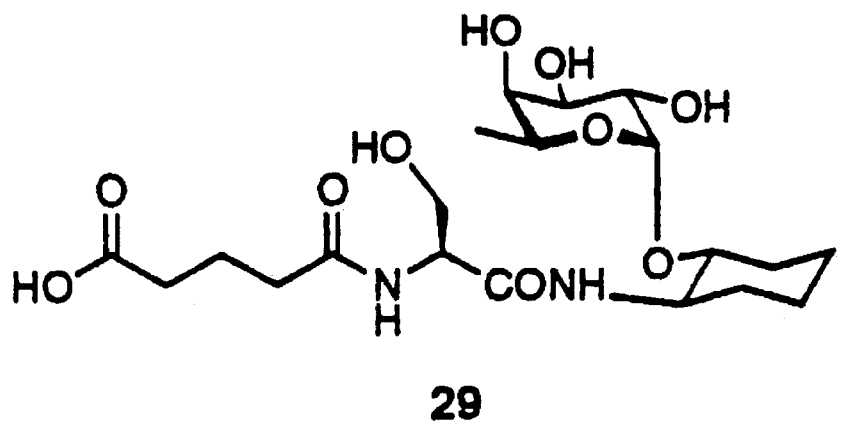
FIGS. 4A and 4B illustrate the sLeX polymer/E-selecting binding assay for compound 29. Each point represents the mean +/− standard deviation of one experiment run in triplicates.
Figure 4B:
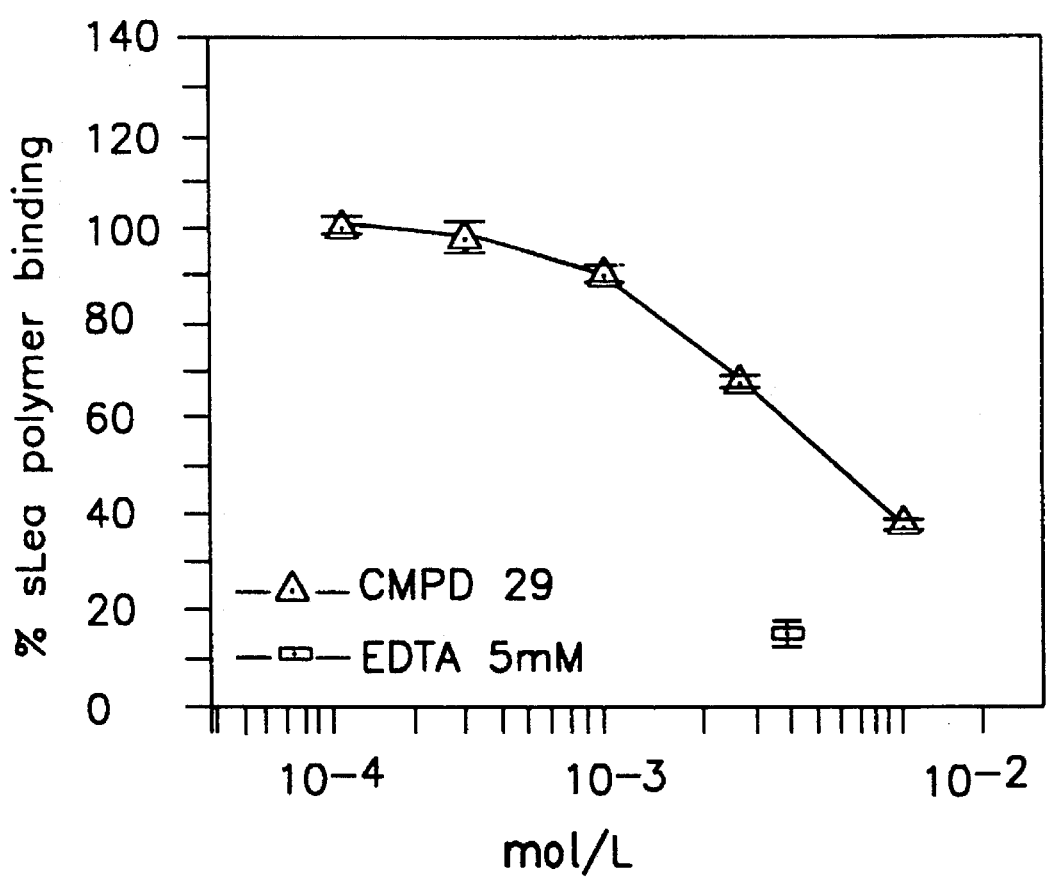
Figure 5A:
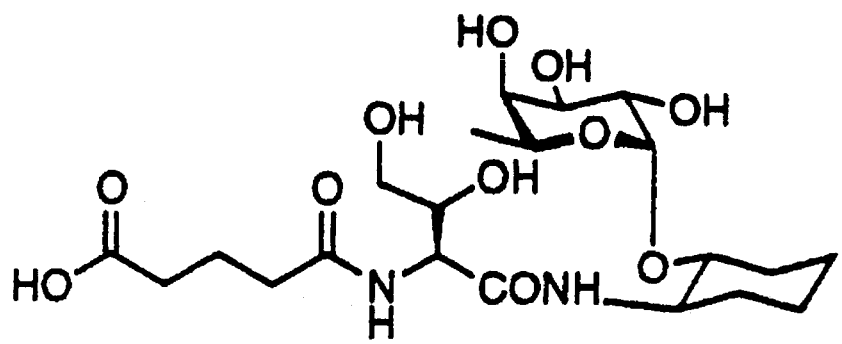
FIGS. 5A and 5B illustrates the $sLe^x$ polymer/E-selecting binding assay for compound 32. Each point represents the mean +/− standard deviation of one experiment run in triplicates.
Figure 5B:
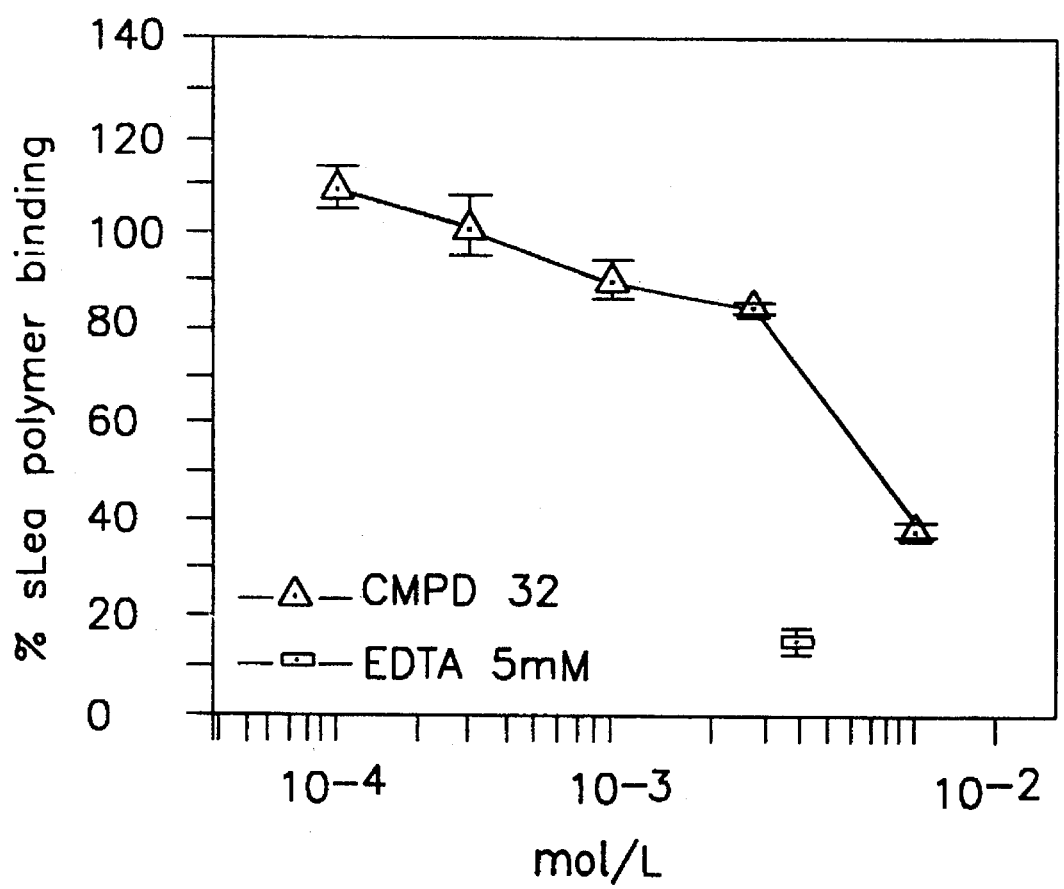
Figure 6A:
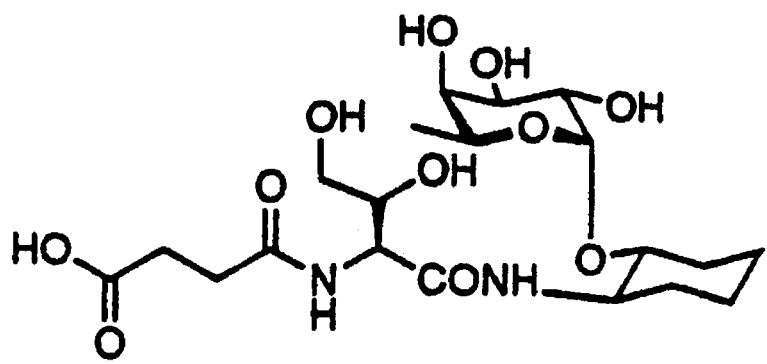
FIGS. 6A and 6B illustrates the $sLe^x$ polymer/E-selecting binding assay for compound 37 (2S, 3R). Each point represents the mean +/− standard deviation of one experiment run in triplicates.
Figure 6B:
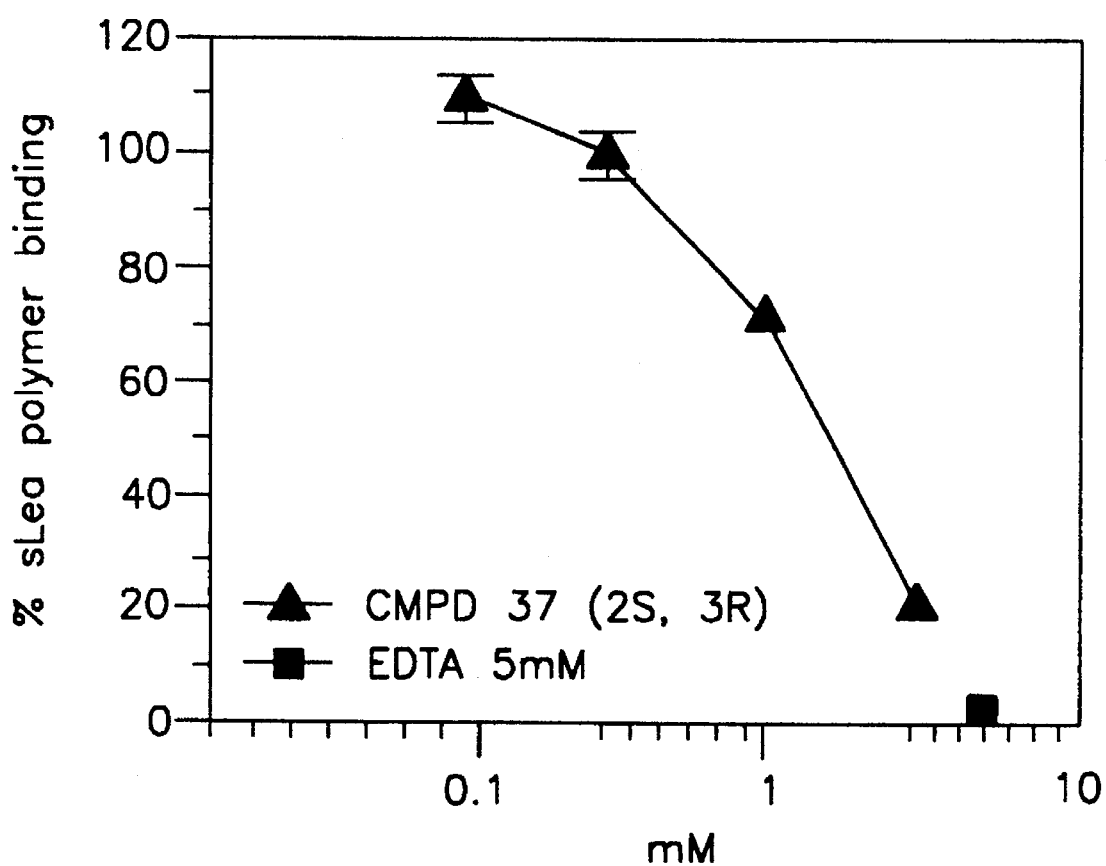
Figure 7A:
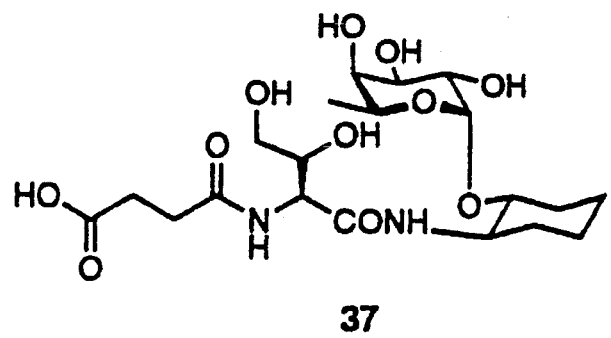
FIGS. 7A and 7B illustrates the HL-60/E-selectin flat-BOTTOM adhesion binding assay for compounds 37 (2S, 3R).
Figure 7B:
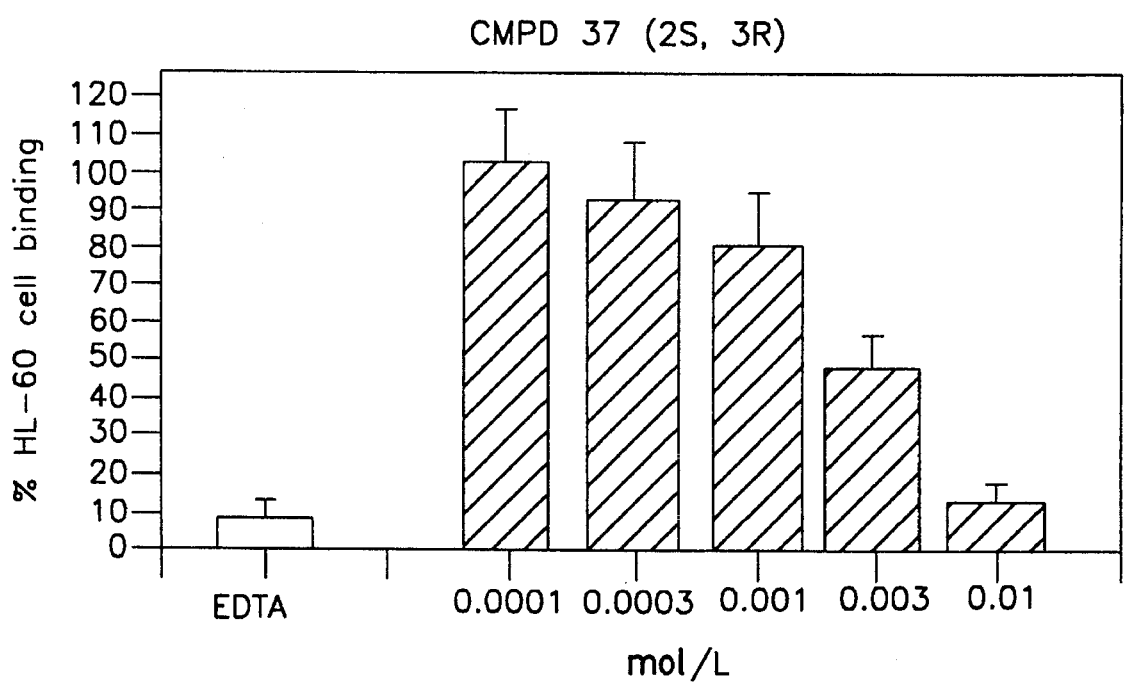
Figure 8A:
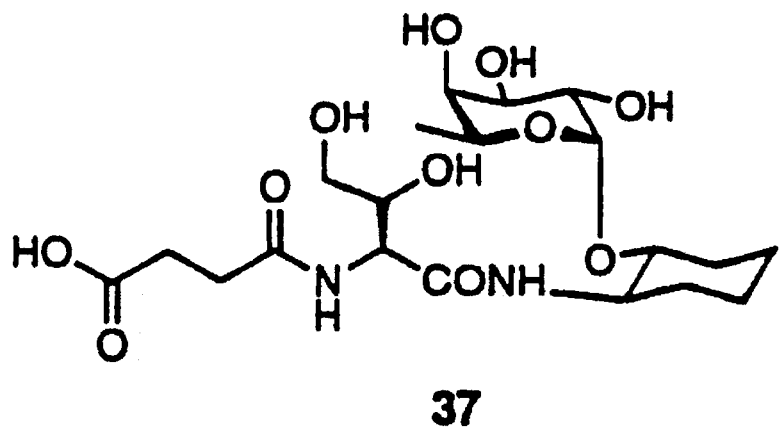
FIGS. 8A and 8B illustrates the $sLe^x$ polymer/E-selecting binding assay for compound 37 (2S, 3S). Each point represents the mean +/− standard deviation of one experiment run in triplicates.
Figure 8B:
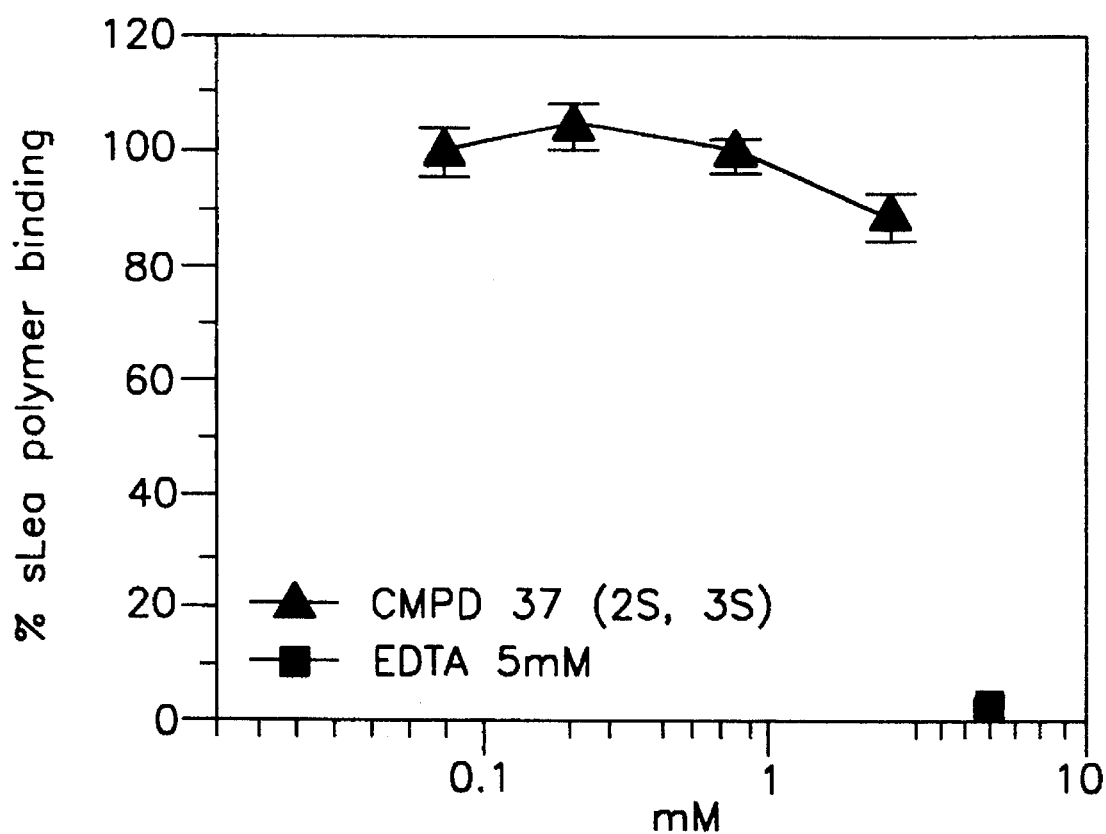
Figure 9A:
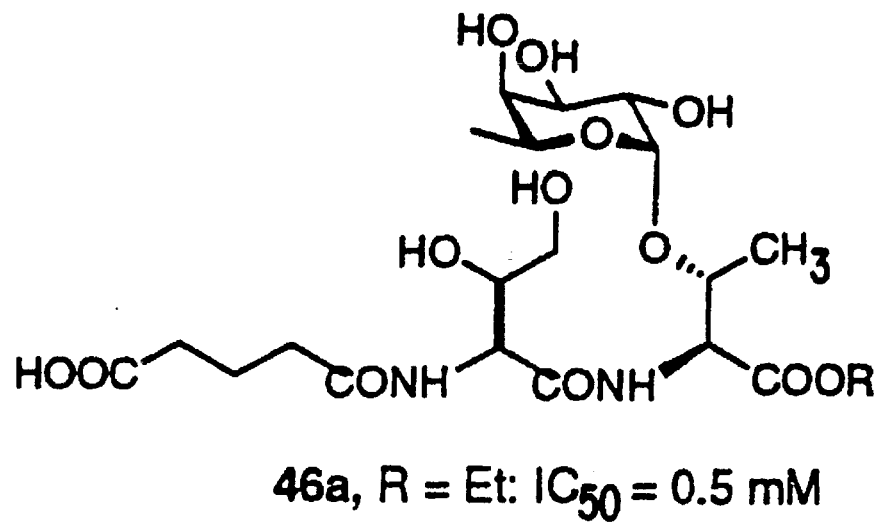
FIGS. 9A and 9B illustrate the $sLe^x$ polymer/E-selecting binding assay for compound 46a. Each point represents the mean +/− standard deviation of one experiment run in triplicates.
Figure 9B:
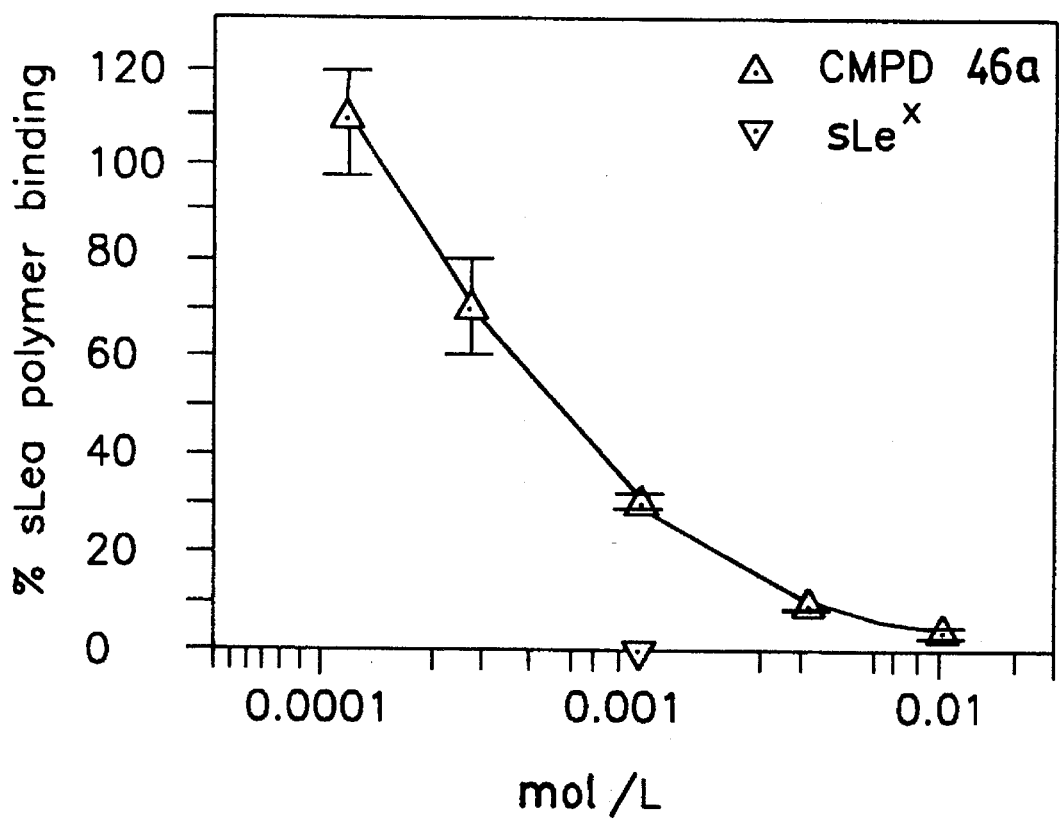
Figure 10A:
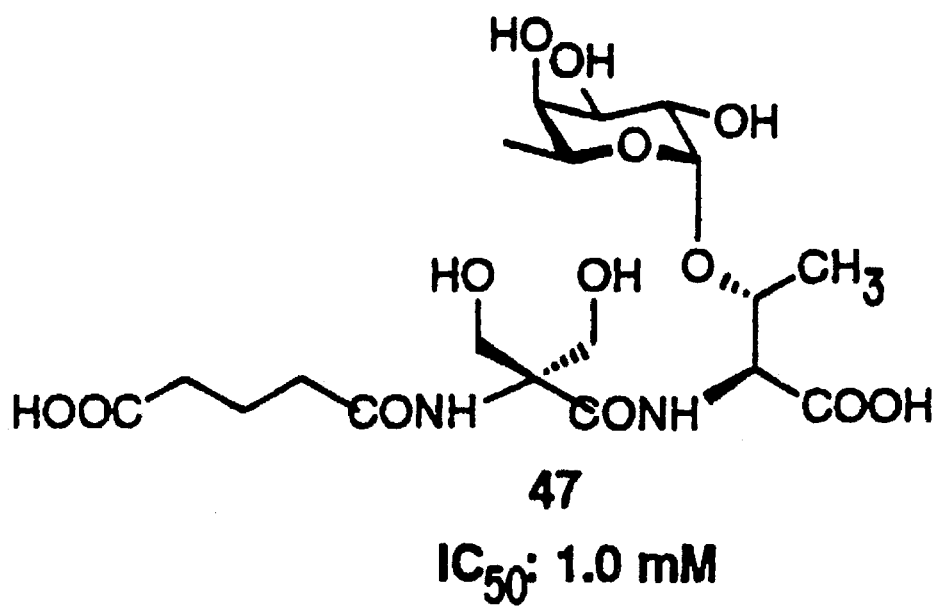
FIGS. 10A and 10B illustrate the $sLe^x$ polymer/E-selecting binding assay for compound 47. Each point represents the mean +/− standard deviation of one experiment run in triplicates.
Figure 10B:
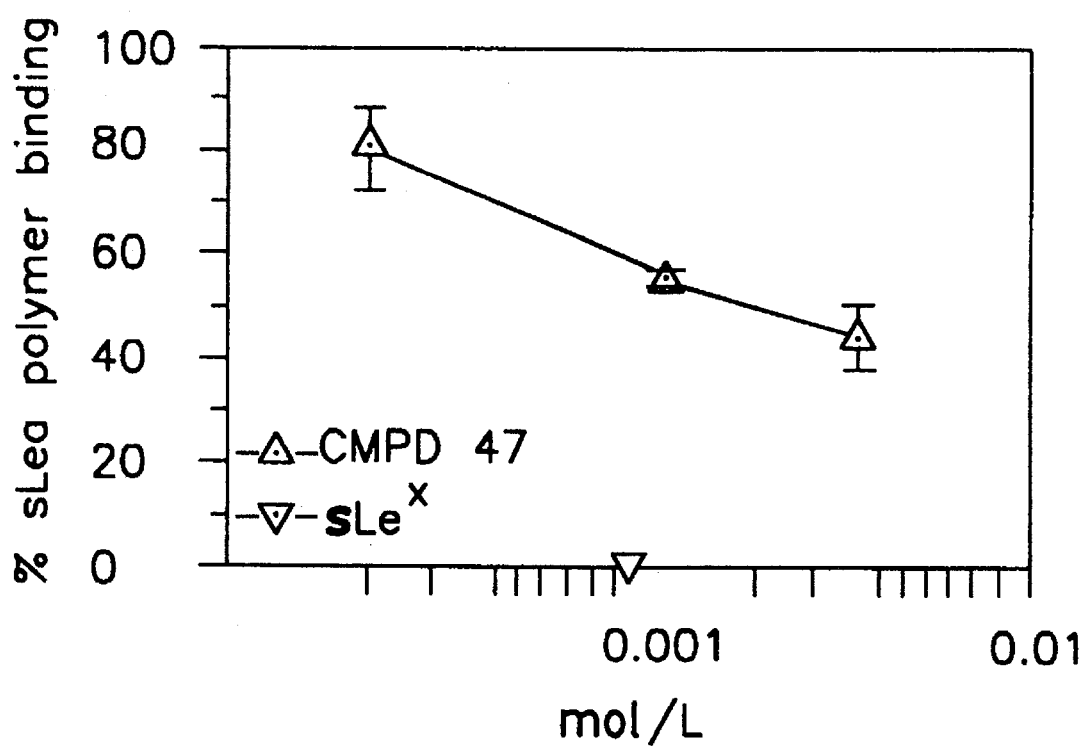
Figure 11A:
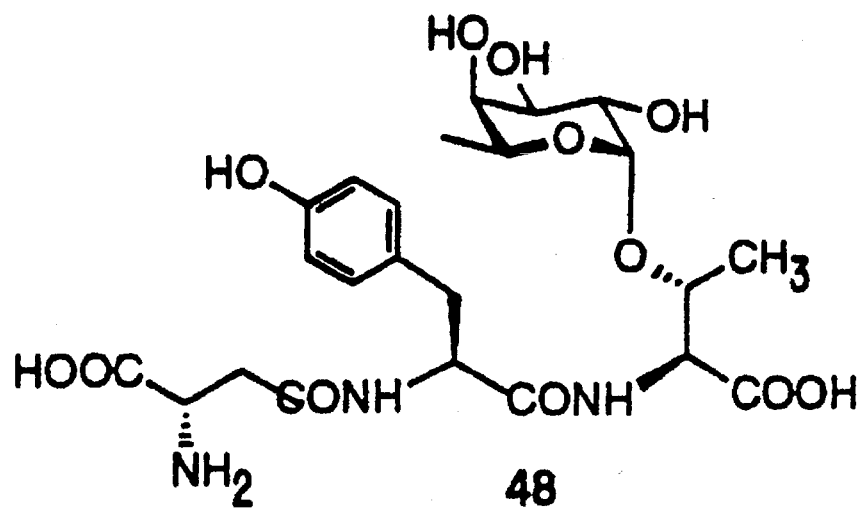
FIGS. 11A and 11B illustrate the $sLe^x$ polymer/E-selecting binding assay for compound 48. Each point represents the mean +/− standard deviation of one experiment run in triplicates.
Figure 11B:
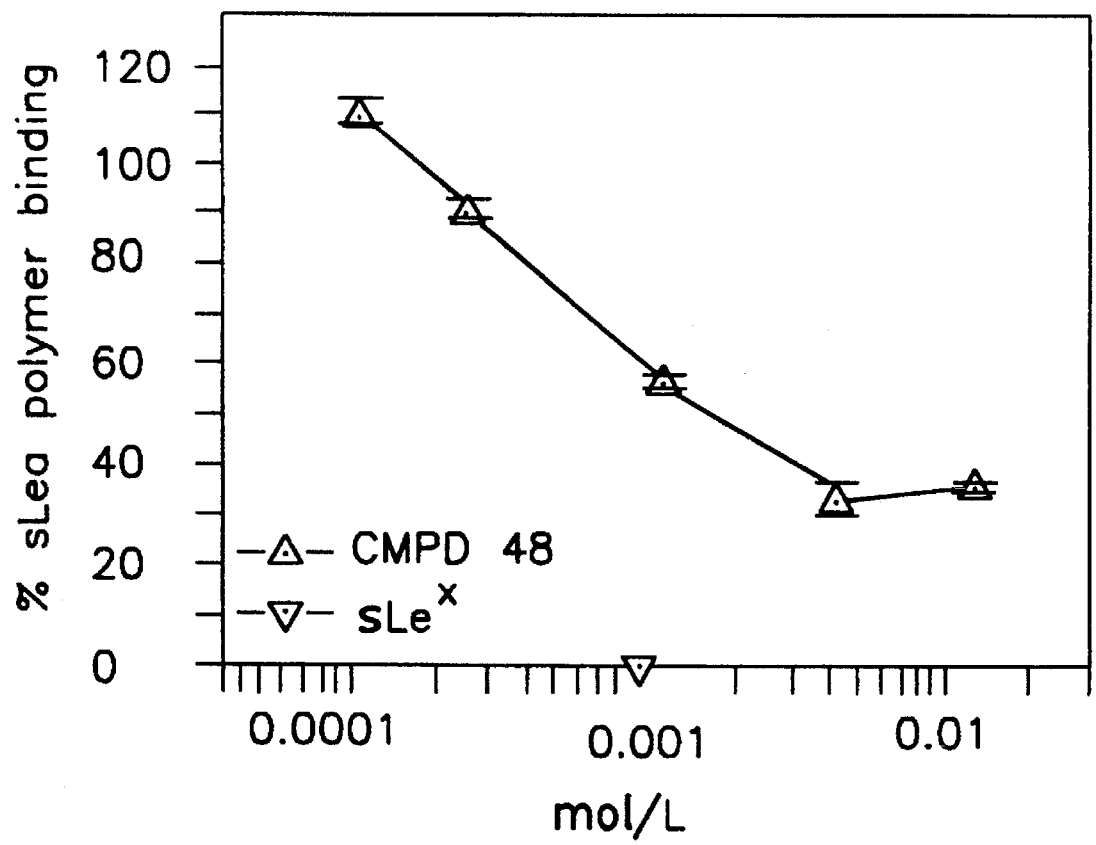
Figure 12A:
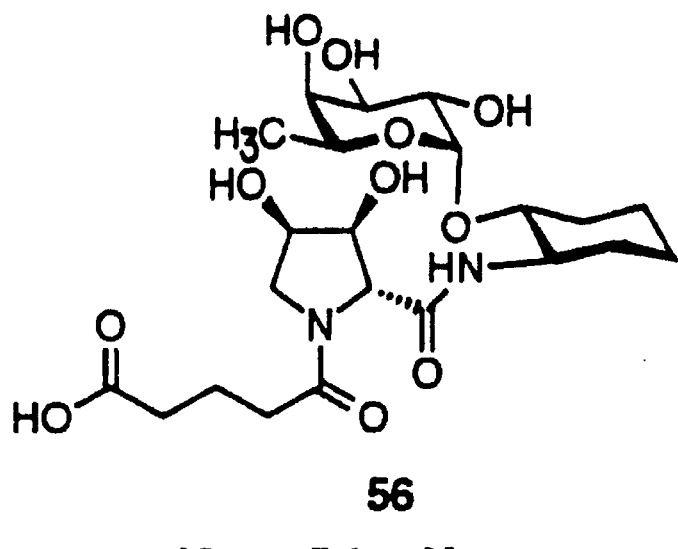
FIGS. 12A and 12B illustrate the sLe$^x$ polymer/E-selecting binding assay for compound 56. Each run in point represents the mean +/− standard deviation of one experiment triplicates.
Figure 12B:
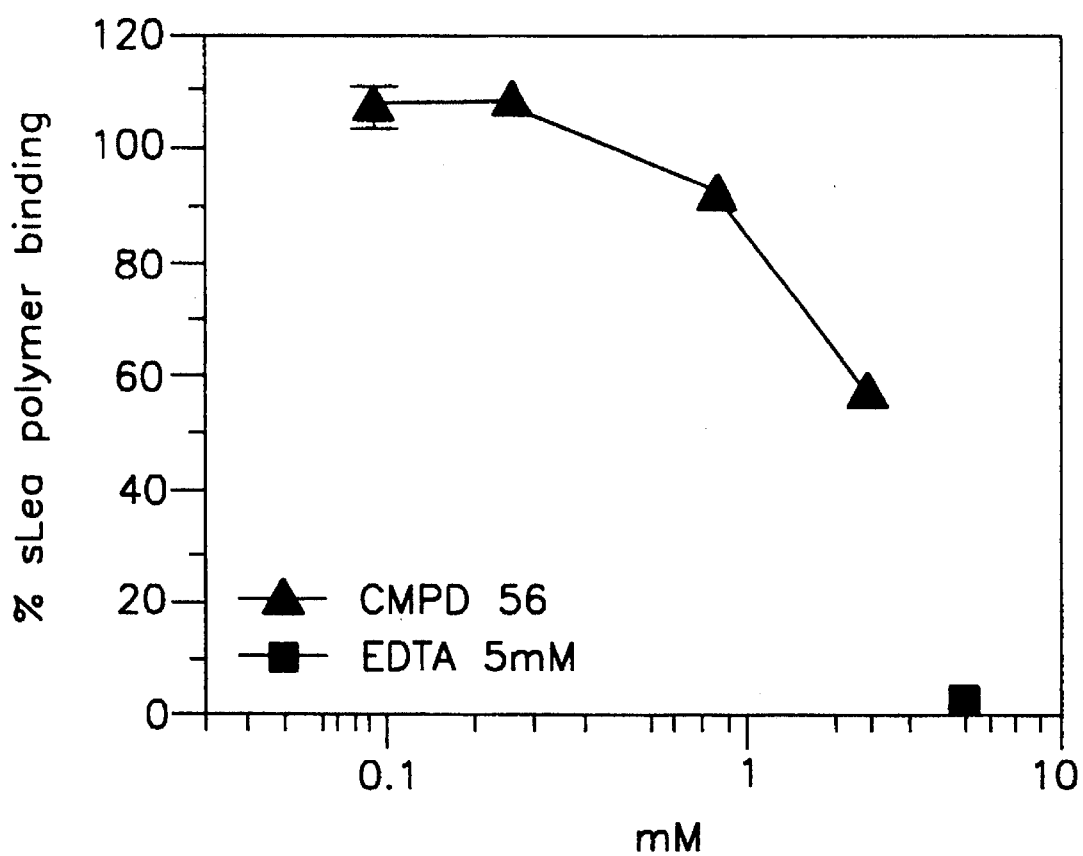
Figure 13A:
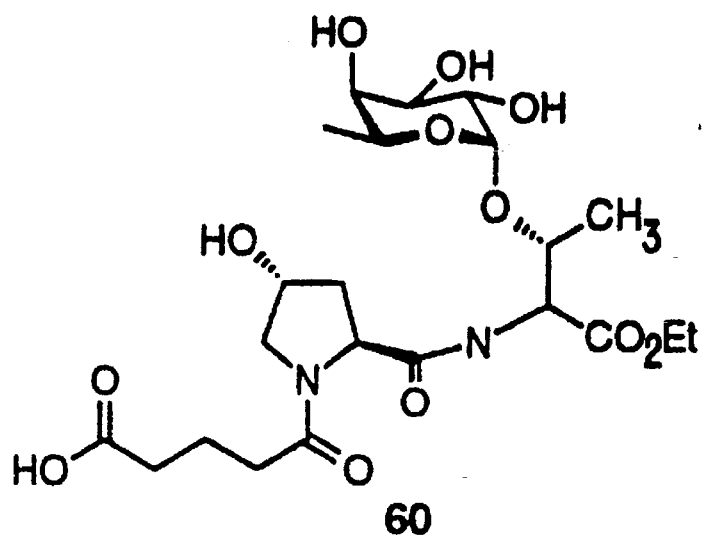
FIGS. 13A and 13B illustrate the sLe$^x$ polymer/E-selecting binding assay for compound 60. Each point represents the mean +/− standard deviation of one experiment run in triplicates.
Figure 13B:
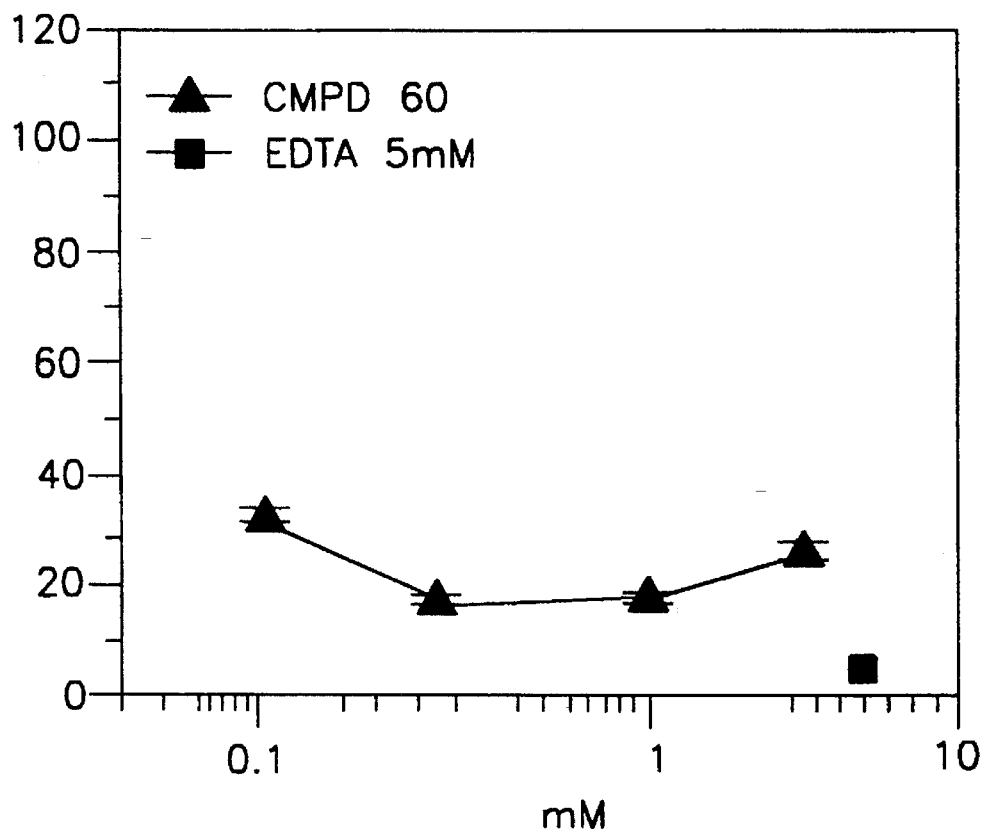
Figure 14A:
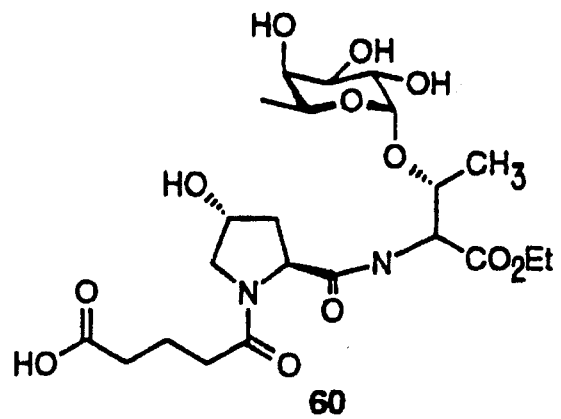
FIGS. 14A and 14B illustrates the HL-60/E-selectin flat-BOTTOM adhesion binding assay for compounds 60.
Figure 14B:
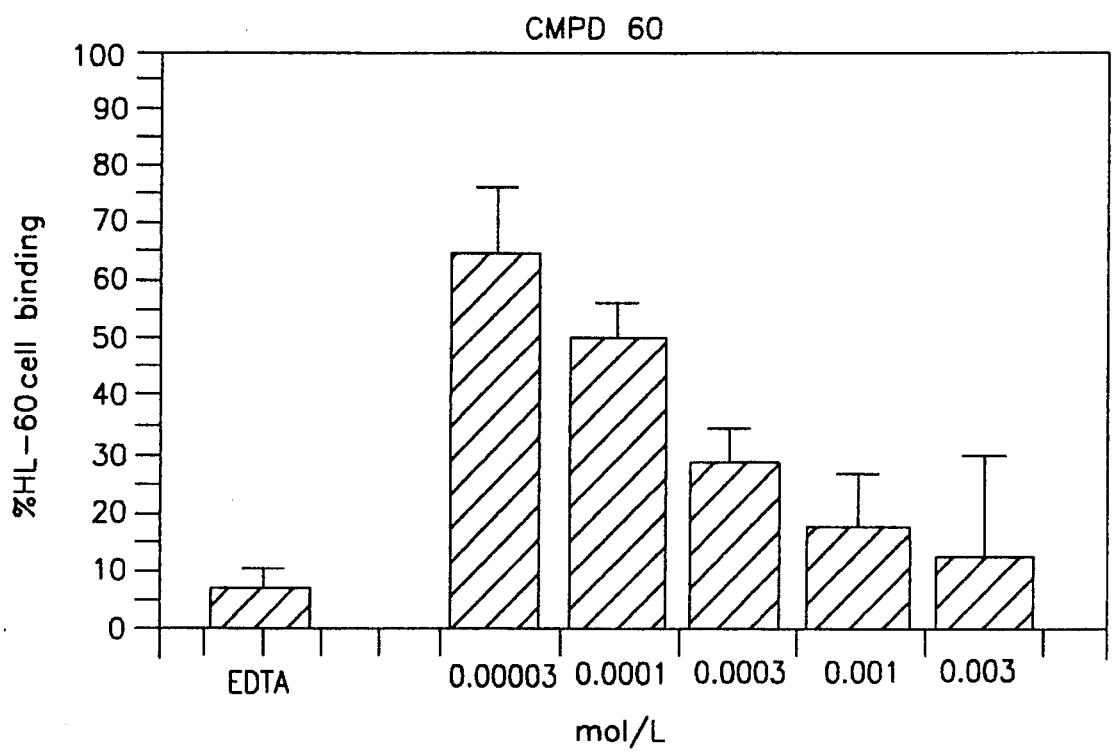
Figure 15A:
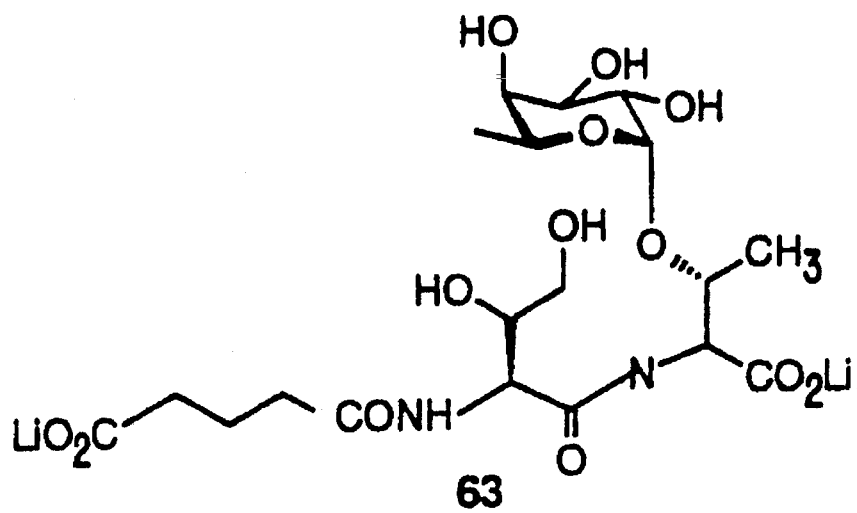
FIGS. 15A and 15B illustrate the sLe$^x$ polymer/E-selecting binding assay for compound 63. Each point represents the mean +/− standard deviation of one experiment run in triplicates.
Figure 15B:
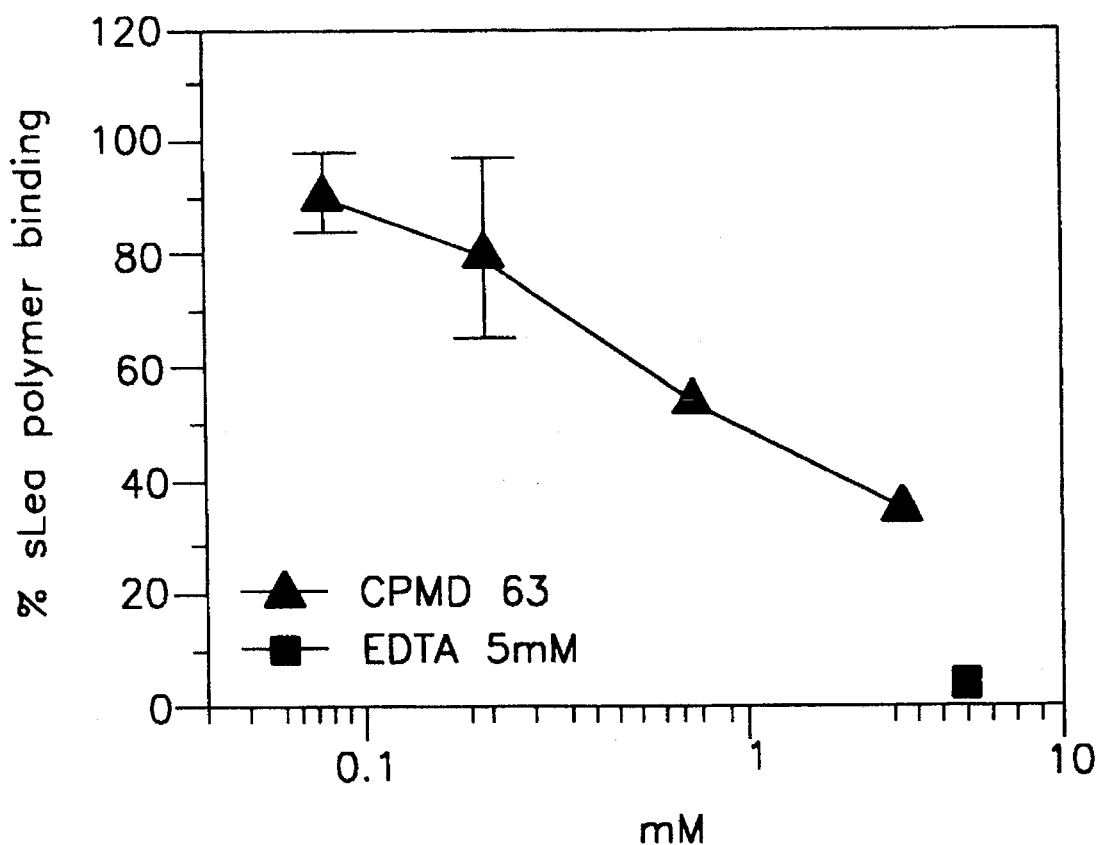
Figure 16A:
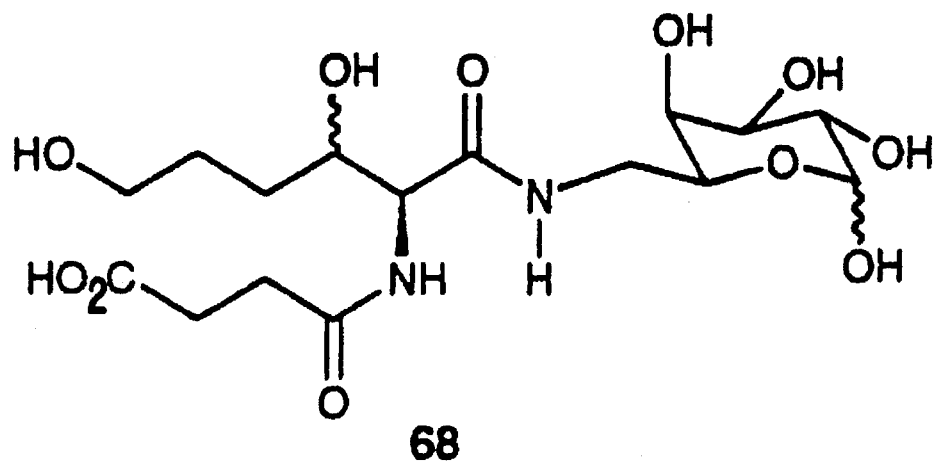
FIGS. 16A and 16B illustrate the sLe$^x$ polymer/E-selecting binding assay for compound 68. Each point represents the mean +/− standard deviation of one experiment run in triplicates.
Figure 16B:
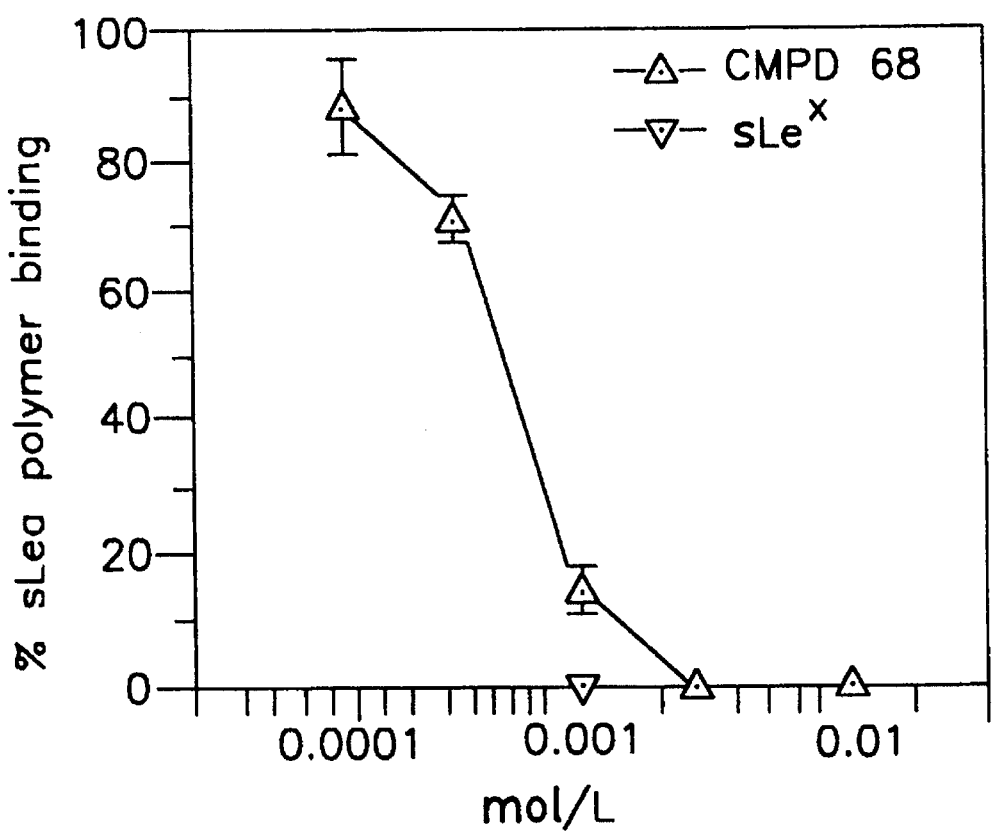
Figure 17A:
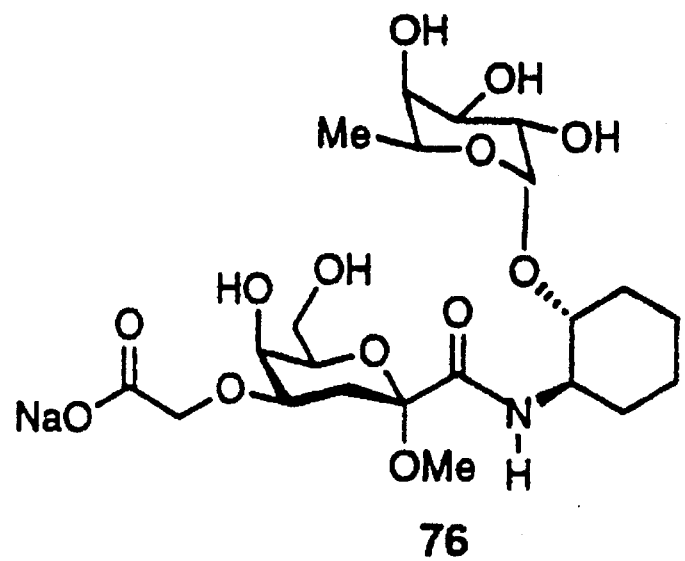
FIGS. 17A and 17B illustrate the sLe$^x$ polymer/E-selecting binding assay for compound 76. Each point represents the mean +/− standard deviation of one experiment run in triplicates.
Figure 17B:
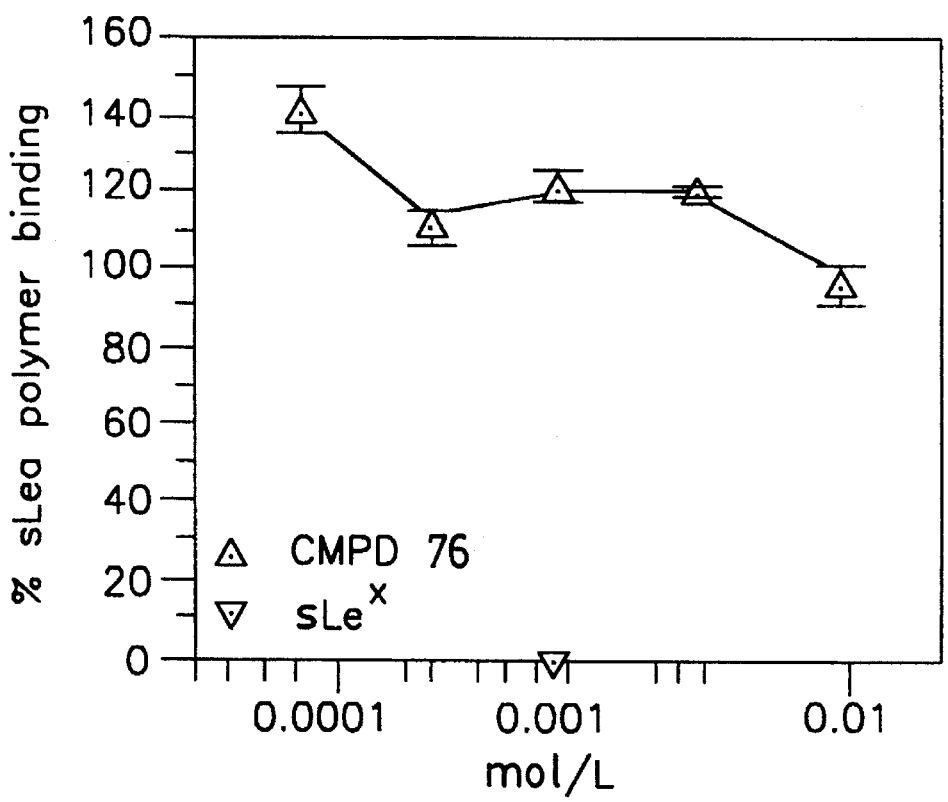

The design, synthesis, and activity of simple sLe$^x$ mimetics incorporating fucopeptides are dislosed. Compounds of this class of sLe$^x$ mimetics possess substantially the same activity as sLe$^x$ in the E-selectin binding assay. The fucopeptide (46a) is one of the preferred compounds of the invention. Compound 46a contains a L-fucose residue, two OH groups from (1S,2R)-1-amino-2,3-dihydroxybutyric acid to mimic the 4- and 6-OH groups of the Gal residue and a —$CO_2$— group from glutarate residue to mimic the negative charge of the sialic acid residue. Using L-threonine to replace N-acetylglucosamine is expected to retain a similar configuration for the glycosidic linkages. Molecular modeling indeed indicates that compound 46a matches the six functional groups of the active sLe$^x$ in space. Compounds 47 and 48 were designed in a similar way except that the dihydroxy amino acid is replaced with another amino acid in order to address its role in recognition.

The synthesis of 46a is shown in Scheme 6. L-Fucose was first converted to tribenzylfucosyl phosphite by the method of Muller et al. as modified by Kondo et al. (T. Muller, et al. *Liebigs Ann. Chem.* 1994, 325; and H. Kondo, et al. *J. Org. Chem.* 1994, 59, 864.) The product thereof was then successfully coupled to Boc-L-Thr-OEt using trifluromethanesulfonic acid (or TMSOTf) as catalyst to give the Boc-L-Thr (tri-O-benzyl-a-Fuc)-OEt (40) in 80% yield. Following the Boc deprotection of 40 (30% TFA in $CH_2Cl_2$, 25° C., 30 min), L-Thr (tri-O-benzyl-a-Fuc)-OEt was coupled with ( 1S, 2R)-N-Boc-1-amino-3-benzyloxy-2-hydroxy butyric acid (1.5 equiv of EDCI, 1.5 equiv of HOBt, $CH_2Cl_2$, 0° C., 30 h, 60%) to provide 44. This unusual amino acid was prepared from glycine and O-benzylglycolaldehyde by L-threonine aldolase-catalyzed reaction according to the method of V. P. Vassilev, et al., viz. *Tetrahedron Lett.* 1995, 36, 4081. α-Hydroxymethyl serine was prepared according to the procedure of Otani et al., viz. *Arch. Biochem. Biophys.* 1960, 90, 254. Boc deprotection of 5 followed by coupling with monobenzyl glutarate provided compound 45 (1.5 equiv of EDCI, 1.5 equiv of HOBt, $CH_2Cl_2$, 25° C., 20 h, 70%). The benzyl groups of 45 were cleaved by hydrogenation over 20% Pd(OH)$_2$/C in MeOH and the crude product was purified on Biogel P-2 chromatography to obtain 46a (54%). Compound 46a and other key intermediates were characterized by $^1$H NMR and high resolution mass analysis. Compounds 47 and 48 were synthesized from the key intermediate 4 by the same methods.

Analysis of these compounds as inhibitors of sLe$^x$ glycoconjugate binding to E-selectin provides IC$_{50}$ values: 46a, 0.55 mM; 47, 1.0 mM; 48, 1.3 mM, according to the method of S. A. DeFrees, et al., viz. *J. Am. Chem. Soc.* 1995, 117, 66. Conversion of 46a to 46b weakens the activity (IC$_{50}$=1.0 mM). Since compound 46a has almost the same biological activity as sLe$^x$ (0.50 mM). All the functional groups required for E-selectin binding in sLe$^x$ therefore exist in 46a. Compounds 46b and 47 are slightly less active than sLe$^x$, probably due to the presence of free carboxyl group in the Thr moiety. Compound 48 is, however, surprisingly active as the OH group of Tyr in 48 is not exactly a mimic in space of the essential OH groups of Gal residue in sLe$^x$. Whether the hydrophobic nature of the aromatic group or the additional amino group contributes to binding is unclear. Replacement of the dihydroxy amino acid with L-Thr, L-Ser, Phe, Ala or Gly, however, resulted in a nearly complete loss of activity (IC$_{50}$>10 mM). This study thus confirms the minimum structural elements required for E-selectin recognition and provides a new direction to the development of sLe$^x$ mimetics. Compared to sLe$^x$, the synthesis of 46a is very straightforward and can be easily scaled up.

The synthesis, physical characterization, and activity of other exemplary compounds of this genus of sLe$^x$ mimetics incorporating fucopeptides are provided below.

Overview of Assay for the Biological Activity of SLe$^x$ Mimetics

A soluble form of E-selectin (sol-E-selectin) was prepared for inhibition assays of the SLe$^x$ Mimetics. A 1.67 kbp DNA fragment encoding a truncated structural gene for E-selectin was isolated by PCR amplification of cDNA derived from messenger RNA that was isolated from IL-1 activated human endothelial cells. The cDNA was subcloned into the vector pBluescript II and was transfected into 293 cells. The clones were screened for the production of sol-E-selectin, and the clone 293#3 was selected as the stable cell line that produced the greatest amount of sol-E-selectin per cell. Sol-E-selectin was produced on a large scale from this line using a Nunc cell factory. Recombinant sol-E-selectin was isolated from the media using immunoaffinity chromatography.

The SLe$^x$ Mimetics were assayed for ability to block the adhesion of HL-60 cells to immobilized ol-E-selectins (either on a polymeric column solid support or onto the surface of the assay vessle). Immobilized E-selectin was incubated first with inhibitor and then with HL-60 cells. The bound cells were lysed, and myeloperoxidase released from the bound cells was detected with o-phenylenediamine and hydrogen peroxide. The percentage inhibition was determined by comparing the absorbance of the resulting solution at 492 nm to that in wells containing no inhibitor.

Each data point in the E-selectin assay is a direct measure of cells bound using a quantitative enzyme assay. The values were then plotted to give the titration curve and IC$_{50}$ values. On average, five assays were performed for each inhibitor, and the results were highly reproducible. The standard deviation did not exceed 6.3% for any data point. The IC$_{50}$ values reported here is derived from all the data.

Cellular Binding Assays

A modified recombinant soluble E-selectin/HL-60 cell adhesion assay was used to provide a simple and highly reproducible method with which to compare the E-selectin-blocking potential of a SLe$^x$ mimetic compound. In this assay, recombinant soluble E-selectin (rELAM) is bound to the plastic surface of a 96 well ELISA plate. Dilutions of SLe$^x$ mimetic compound to be assayed are added to the wells followed by HL-60 cells which bear the ligand for E-selectin. The cells are allowed to adhere to the E-selectin coated assay plate and the nonadherent cells are removed by washing the plate with an automated plate washer. Bound cells are quantitated by measuring the cellular enzyme myeloperoxidase. The molar concentration of assayed SLe$^x$ mimetic required to achieve 50 percent inhibition of control adhesion such as that inhibited by free SLe$^x$ is used to compare the contemplated mimetics for potency. The efficacy of using a similar bound recombinant soluble portion of ELAM-1 as a substrate for binding HL-60 and other cells that bind to cells containing the ELAM-1 (E-selectin) receptor has been demonstrated by Lobb et al., *J. Immunol.*, 147:124–129 (1991), and more recently in DeFrees et al., *J. AM. Chem. Soc.*, 117:66–79 (1995).

MATERIALS AND METHODS

Materials

ELISA plate, Immulon 2 (Dynatec Laboratories) (Fisher 14-245-61)

0.2 m filter units (Nalgene #150-0020)

RELAM (recombinant modified ELAM-1) affinity purified, prepared as follows below. Each batch of RELAM was tested functionally to determine the appropriate concentration for use in the assay. Small aliquots were then prepared, quick frozen in a dry-ice acetone bath and stored at −70° C. Each aliquot was opened only one time and then discarded or saved for use in other types of assays.

The soluble form of E-selectin (RELAM or sol-E-selectin) used here was engineered by deleting the transmembrane domain from the CDNA. This recombinant CDNA was cloned into a mammalian expression vector pCDNA1 [a derivative of pCDM8; Seed, *Nature,* 329:840 (1987)] that contains the chimeric cytomegalovirus/human immunodeficiency virus promoter. When introduced into the adenovirus-transformed human kidney cell line 293, expression of the CMV promoter is efficiently activated by the E1 gene products by a mechanism that has not been fully delineated. The PCDNA1-sol-E-selectin construction was introduced, via calcium phosphate-mediated gene transfer, into 293 cells and a stable cell line expressing high levels of sol-E-selectin was generated. The sol-E-selectin produced by these cells was purified by immunoaffinity chromatography on an anti-E-selectin monoclonal antibody Protein-A Sepharose column.

More specifically, the adenovirus transformed human kidney cell line 293 was obtained from the ATCC (CRL-1573). 293 Cells were grown as adherent cultures in DMEM, obtained from Whittaker Bioproducts (Walkersville, Md.), supplemented with 10 percent fetal bovine serum (FBS), obtained from JRH Biochemical (Lenexa, Kans.).

The plasmid PCDNA1, a derivative of PCDM8 [Seed, *Nature,* 339:840 (1987)], was obtained from Invitrogen (San Diego, Calif.). The plasmid pBluescript II was obtained from Stratagene (San Diego, Calif.). The plasmid pSV2-neo [Southern et al., *J. Mol. Appl. Gen.,* 1:327 (1982)] contains the *E. coli* gene encoding the aminoglycoside 3'-phosphotransferase gene. When PSV2-neo is introduced into mammalian cells, the transfected cells exhibit resistance to the antibiotic G418.

A 1.67 Kbp DNA fragment encoding a truncated structural gene for E-selectin was isolated by polymerase chain reaction (PCR) amplification of CDNA derived from messenger RNA that was isolated from IL-1-activated human endothelial cells. The 5'-amplimer inserted a unique ClaI restriction site 28 nucleotides upstream from the initiation codon of the E-selectin structural gene. The 3'-amplimer inserted the termination codon TGA after amino acid number 527 of the mature E-selectin, followed by a unique XhoI restriction site. The carboxy-terminus of sol-E-selectin is located at the carboxy terminus of the sixth consensus repeat element, thereby deleting the transmembrane domain. The 1.67 Kbp PCR fragment was codigested with ClaI and XhoI restriction endonucleases and sub-cloned into the ClaI and XhoI restriction sites of the cloning vector pBLUESCRIPT II, providing vector pBS11-sol-E-selectin. Expressed soluble-E-selectin is 527 amino acid residues in length and contains 11 potential N-glycosylation sites.

A 1.67 Kbp DNA fragment containing the sol-E-selectin cDNA was isolated from pBS 11-sol-E-selectin and sub-cloned into the EcoRV and XhoI sites of the expression vector pCDNAI, thereby providing vector pCDNAI-sol-E-selectin.

pCDNAI-sol-E-selectin was cotransfected with pSV2-neo, via the calcium phosphate technique [Kriegler, *Gene Transfer and Expression: A Laboratory Manual,* W. H. Freeman, New York, N.Y. (1991)] into 293 cells. Forty-eight hours post-transfection, the transfected 293 cells were trypsinized and plated into DMEM, 10 percent FBS, and 600 μg/mL (potency) of G418 (Geneticin, Sigma). The selection medium was changed every three days until a stable G418-resistant population was established.

Single clones of G418-resistant cells were isolated by cloning cylinders. Isolated clones were screened for the synthesis of sol-E-selectin by enzyme-linked immunosorbent assay (ELISA) utilizing the anti-E-selectin monoclonal antibody designated CY1787 as the primary antibody. Positive clones were plated at $10^6$ cells/100 mm dish. They were metabolically labeled 24 hours later with [$^{35}$S]-methionine for five hours. Labeled sol-E-selectin was immunoprecipitated from the medium with the anti-E-selectin monoclonal antibody CY1787 and electrophoresed through a 10 percent PAGE gel, the gel dried and subjected to autoradiograph. Clone 293#3 was selected as the stable cell line that produced the greatest amount of the 110-Kd sol-E-selectin protein/cell.

A 10-chambered Nuc Cell Factory (6250 cm$^2$ total surface area, Nunc) was seeded with 2.78×10$^8$ cells (clone 293#3) in 850 mL in DMEM supplemented with five percent FBS and incubated at 37° C. for 72 hours. The medium was harvested and replaced with 850 mL of DMEM five percent FBS. After the cell factory was incubated at 37° C. for 48 hours, the medium was harvested a second time and replaced with 850 mL DMEM, five percent FBS. After the cell factory was incubated at 37° C. for 48 hours, the medium was harvested a third (and final) time.

After each harvest, 0.02 percent sodium azide was added to the medium. The medium was clarified by centrifugation (5000×g), passed through a 0.2 μm filter and stored at 4° C. until further purification.

Monoclonal antibody CY1787 was conjugated to protein-A Sepharose essentially as described by Schneider et al., *J. Biol. Chem.,* 257:10766 (1982). Briefly, 28 mg of monoclonal CY1787 (5 mg/mL) in PBS was mixed with 5 mL of protein-A Sepharose for 30 minutes at room temperature. The beads were then washed four times by centrifugation with 25 mL of 0.2M borate buffer, pH 8.2, followed by two washes with 10 mL of 0.2M triethanolamine, pH 8.2. The resin was then suspended in 40 mL of 0.2M triethanolamine buffer, pH 8.2, containing 0.02M dimethylpimelimidate. After reacting for 45 minutes at room temperature on a rotator, the resin was washed twice with 0.02M ethanolamine, pH 8.2, followed with three washes with 10 mL of 0.2M borate buffer, pH 8.2. Unbound antibody was removed by elution with 0.1M sodium acetate buffer, pH 4.5. Of the antibody applied, 89 percent was conjugated to the protein-A Sepharose.

Tissue culture supernatant (2550 mL) was passed through a 0.7 cm×1.5 cm pre-column of protein-A Sepharose connected in series to a 1.5 cm×3 cm affinity column of CY1787-protein-A Sepharose at a flow rate of 20 mL/hr. The columns were then disconnected and the CY1787-containing affinity column was washed with 20 mM Tris buffer, pH 7.5, containing 150 mM NaCl and 2 mM $CaCl_2$ until the absorbance at 280 nm of the eluate approached zero. Bound E-selectin was eluted with 0.1M sodium acetate buffer, pH 3.5, containing 1 mM $CaCl_2$ using gravity flow. Fractions (1 mL) were collected into 300 μL of 2M Tris, pH 10. Protein-containing fractions were pooled and dialyzed against DPBS. Following concentration of an Amicon Centriprep 30 until the protein concentration was approximately 1 mg/mL, the purified E-selectin was aliquoted and stored at −80° C. Purity was greater than 90 percent by SDS-PAGE. A total of 10 mg of E-selectin was purified from 2550 mL of cell culture medium.

Assays were carried out essentially as described in DeFrees etal, *J. Am. Chem. Soc.*, 117:6–79 (1995) and Wong et. al., *J. Am. Chem. Soc.* 1995, 177, 66–79. The foregoing description and the examples are intended as illustrative and are not to be taken as limiting. Still other variations within the spirit and scope of this invention are possible and will readily present themselves to those skilled in the art.

Synthetic Methods and Physical Data

Compound 3

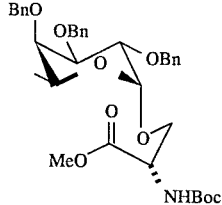

4 Å molecular sieves were added to a solution of 2,3,4-tri-O-benzyl-L-fucopyranosyl fluoride I (L-Fucose was first converted to 2,3,4-tri-O-benzyl-L-fucopyranosyl fluoride from methodology established by Muller et. Al. *Liebigs Ann. Chem.* 1994, 325 and Wong et. Al. *J. Org. Chem.* 1994, 59, 864); (1 grams, 2.3 mmol) in anhydrous dichloromethane (25 mL) at 0° C. under nitrogen and the mixture was stirred for 30 min. Tin(II) chloride (Aldrich company, 0.872 g, 4.6 mmol), silver triflate (1.18 g, 4.6 mmol) and L-Boc-Ser-OMe 2a (Sigma company, 0.76 g, 3.5 mmol) were added and the mixture was warmed to room temperature for 12 hours. The suspension was filtered through celite and the filtrate was washed with water and saturated sodium bicarbonate. The organic layer was dried over $MgSO_4$. Silica gel chromatography afforded 3 (120 mg, 30%, Rf=0.5, hexane/ethylacetate, 2:1) as a clear oil. $^1H$ NMR (500 MHz, $CDCl_3$) δ 1.08 (d, 3H, J=6.5 Hz, H-6), 1.45 (s, 9H, tBu), 3.55 (dd, 1H, J=3.5, 10.0 Hz), 3.61 (m, 1H, H-4), 3.70 (s, 3H, $OCH_3$), 3.72 (m, 1H, H-5), 3.82 (dd, 1H, J=3.0, 10.5 Hz, H-3), 4.01 (dd, J=4.0, 10.5 Hz, H-2), 4.14 (dd, 1H, J=3.0, 10.0 Hz), 4.47 (m, 1H), 4.66 (dd, 1H, J=4.0 Hz, H-1), 4.62–4.97 (m, 6H, 3×$CH_2Ph$), 5.87 (d, 1H, J=9.0 Hz, N—H), 7.31 (m, 15H, 3×$C_6H_5$). HRMS calcd for $C_{36}H_{45}NO_9Cs$ (M+$Cs^+$) 768.2149, found 768.2149.

Compound 4

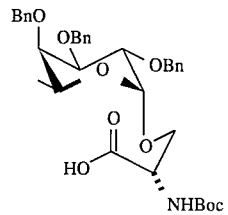

Compound 3 (120 mg, 0.19 mmol) was dissolved in methanol/$H_2O$ (2:1). $LiOH.H_2O$ (9.51 mg, 0.23 mmol) was added and the solution was stirred at room temperature for 12 h. Methanol was evaporated and the remained aqueous solution was acidified to pH 4 by 1N HCl and extracted with ethyl ether. The organic fractions were combined and dried over $MgSO_4$. Evaporation of the solvent afforded 4 (61 mg, 52%) as a clear oil. $^1H$ NMR (500 MHz, $CDCl_3$) δ 1.10 (d, 3H, J=6.5 Hz, H-6), 1.44 (s, 9H, tBu), 3.55 (dd, 1H, J=3.0, 10.0 Hz), 3.74 (m, 1H), 3.78–3.98 (m, 5H), 4.14 (dd, 1H, J=3.0, 9.5 Hz), 4.32 (m, 1H), 4.57–4.89 (m, 6H, 3×$CH_2Ph$), 4.74 (d, 1H, J=4.0 Hz, H-1), 7.27–7.36 (m, 15H, 3×$C_6H_5$). MS cacld for $C_{35}H_{43}NO_9Na$ (M+$Na^+$) 644, found 644.

Compound 5

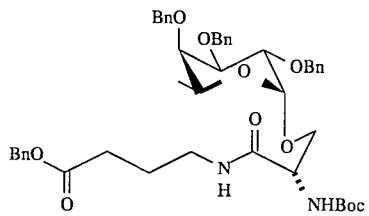

Compound 4 (61 mg, 0.098 mmol), EDAC (1-ethyl-3-(3-dimethylaminopropyl)-carbodiimide; Sigma company; 28.2 mg, 0.147 mmol) and HOBT (1-hydroxybenzotriazole hydrate; Aldrich company; 19.9 mg, 0.147 mmol) was dissolved in dry dichloromethane and 4-aminobutyric acid benzyl ester (24.6 mg, 0.127 mmol) was added. The mixture was stirred at room temperature for 12 hours and diluted with dichloromethane. The organic layer was washed with water twice and dried over $MgSO_4$. Silica gel chromatography (hexane/Ethylacetate, 3:1→2:1) afforded compound 5 (30.3 mg, 71%, Rf=0.4, hexane/Ethylacetate, 1:1). $^1H$ NMR (500 MHz, $CDCl_3$) δ 1.11 (d, 3H, J=6.5 Hz, H-6), 1.44 (s, 9H, tBu), 1.65 (m, 2H), 2.23 (m, 2H), 3.17 (m, 1H), 3.66 (d, 1H, J=2.0 Hz, H-4), 3.88 (m, 2H, H-3 and H-5), 4.03 (dd, 1H, J=4.0, 10.0 Hz, H-2), 4.18 (m, 2H), 4.61 (d, 1H, J=11.5 Hz), 4.67 (d, 1H, J=12.0 Hz), 4.71 (d, 1H, J=3.5 Hz, H-1), 4.75 (s, 2H), 4.92 (dd, 2H, J=11.5, 15.0 Hz), 5.07 (d, 2H, J=2.0 Hz), 7.26–7.40 (m, 20 H). HRMS calcd for $C_{46}H_{57}N_2O_{10}$ (M+$H^+$) 797.4013, found 797.4030.

Compound 6

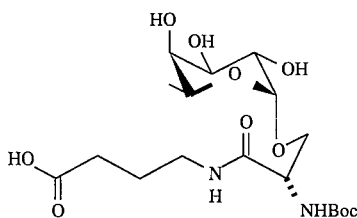

Compound 5 (15 mg, 0.019 mmol) was dissolved in methanol (2 mL) and Pd(OH)$_2$ on carbon (wet, Degussa type E101 NE/W, 5 mg; Aldrich company) was added. The mixture was stirred under hydrogen (1 atm) at room temperature for 12 h. The catalyst was filtered through celite and the filtrate was evaporated to afford 6 (8.3 mg, 100%) as a clear oil. $^1$H NMR (500 MHz, CD$_3$OD) δ 1.24 (d, 3H, J=6.5 Hz, H-6), 1.53 (s, 9H, tBu), 1.84 (m, 2H), 2.38 (t, 2H, J=7.5 Hz), 3.30 (m, 2H), 3.58 (dd, 1H, J=3.0, 10.0 Hz), 3.68 (m, 1H, H-4), 3.71 (dd, 1H, J=3.5, 10.0 Hz, H-3), 3.81 (dd, 1H, J=4.0, 10.0 Hz, H-2), 3.85 (m, 1H, H-5), 4.17 (dd, 1H, J=4.0, 10.0 Hz), 4.27 (m, 1H), 4.78 (d, 1H, J=4.0 Hz, H-1). $^{13}$C NMR (125 MHz, CD$_3$OD) δ 16.56, 26.00, 28.71, 32.27, 39.87, 56.40, 67.80, 68.80, 69.90, 71.50, 73.50, 80.90, 100.2, 157.9, 173.2, 177.1. HRMS cacld for C$_{18}$H$_{33}$N$_2$O$_{10}$ (M+H$^+$) 437.2135, found 437.2130.

Compound 7

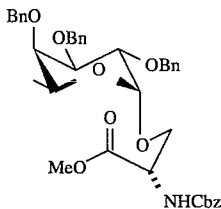

4 Å molecular sieves was added to a solution of 2,3,4-tri-O-benzyl-L-fucopyranosyl fluoride 1(L-Fucose was first converted to 2,3,4-tri-O-benzyl-L-fucopyranosyl fluoride from methodology established by Muller et. Al. *Liebigs Ann. Chem.* 1994, 325 and Wong et. Al. *J. Org. Chem.* 1994, 59, 864); (0.849 g, 1.95 mmol) in anhydrous dichloromethane (25 mL) at 0° C. under nitrogen and the mixture was stirred for 30 min. Tin(II) chloride (0.739 g, 3.90 mmol), silver triflate (1.00 g, 3.90 mmol) and L-cbz-Ser-OMe 2b (Sigma company; 0.69 g, 2.73 mmol) were then added and the mixture was warmed to room temperature and stirred for 12 h. The suspension was filtered through celite and the filtrate was washed twice with water and twice with saturated sodium bicarbonate. The organic layer was dried over anhydrous MgSO$_4$. Purification by silica gel chromatography (hexane/Ethylacetate, 5:1) afforded 7 (31%, 404 mg, Rf=0.45, hexane/Ethylacetate, 4:1) as a clear oil. $^1$H NMR (500 MHz, CDCl$_3$) δ 1.12 (d, 3H, J=6.5 Hz, H-6), 3.59–3.63 (m, 2 H), 3.73 (s, 3 H, OMe), 3.85 (dd, 1H, J=2.5, 10.0 Hz), 4.05 (dd, 1H, J=3.5, 10.0 Hz), 4.20 (dd, 1H, J=3.0, 10.0 Hz), 4.58 (m, 1 H), 4.67 (dd, 2H, J=6.0, 11.5 Hz, 2 H,), 4.71 (d, 1H, J=3.5 Hz, H-1), 4.75 (d, 1H, J=12.0 Hz), 4.84 (dd, 2H, J=6.0, 11.5 Hz), 4.50 (d, 1H, J=11.5 Hz), 5.17 (d, 2H, J=4.5 Hz), 7.26–7.41 (m, 20 H). $^{13}$C NMR (125 MHz, CDCl$_3$) δ 14.1, 16.3, 16.4, 16.5, 52.3, 54.2, 60.3, 66.7, 66.9, 68.8, 73.0, 73.3, 74.7, 78.8, 98.7, 127.4, 127.8, 128.1, 138.1, 156.1, 170.5. HRMS calcd for C$_{39}$H$_{43}$NO$_9$PCS (M+Cs$^+$) 802.1992, found 802.1992.

Compound 8

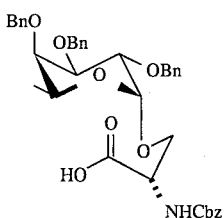

To a solution of 7 in 5:1 mixture methanol to water (25 mL) at 0° C. under nitrogen was added 0.2 equivalents of lithium hydroxide and stirred for 30 min. The suspension was filtered through celite and the filtrate was washed twice with water and twice with saturated ammonium chloride. The organic layer was dried over anhydrous MgSO$_4$. Purification by silica gel chromatography (100% ethylacetate) afforded 8 (54%) as a clear oil.

Compound 9

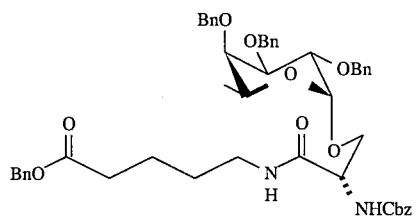

Compound 7 (244 mg, 0.37 mmol) was dissolved in methanol/H$_2$O (2:1) and LiOH.H$_2$O (18.4 mg, 0.44 mmol) was added. The solution was stirred at room temperature for 12 h before methanol was evaporated. The remained aqueous solution was acidified to pH 4 by 1N HCl and extracted with ethyl ether. The organic fractions were combined and dried over anhydrous MgSO$_4$. Evaporation of the solvent afforded 8 (129 mg, 54%) as a clear oil. A solution of 8 (50 mg, 0.076 mmol), EDAC (15.5 mg, 0.11 mmol; 1-ethyl-3-(3-dimethylaminopropyl)-carbodiimide; Sigma company; 28.2 mg, 0.147 mmol) and HOBT (1-hydroxybenzotriazole hydrate; Aldrich company; (15.5 mg, 0.11 mmol) in anhydrous dichloromethane (2 mL) was added 5-aminovaleric acid benzylester (from benzylation of 5-amino-n-valeric acid; 1.0 equiv. KH, methylene chloride, 0° C., 1 hour; Sigma; 19.1 mg, 0.099 mmol). The mixture was stirred at room temperature for 12 h and diluted with dichloromethane. The organic layer was washed with H$_2$O twice and dried over anhydrous MgSO$_4$. Silica gel chromatography (hexane/Ethylacetate, 3:1→1:1) afforded compound 9 (48.3 mg, 75%) as a syrup. $^1$H NMR (500 MHz, CDCl$_3$) δ 1.13 (d, 3H, J=6.5 Hz, H-6), 1.33 (m, 2H), 1.48 (m, 2H), 2.27 (m, 2H), 2.87 (m, 1H), 3.08 (m, 1H), 3.28 (dd, 1H, J=7.5, 9.0 Hz), 3.68 (m, 1H, H-4), 3.89 (m, 2H), 4.04 (dd, 1 H, J=3.5, 10.0 Hz, H-2), 4.18 (m, 1H), 4.27 (m, 1H, H-5), 4.62–5.20 (m, 11H), 7.31 (m, 25H). HRMS calcd for C$_{50}$H$_{56}$N$_2$O$_{10}$Cs (M+Cs$^+$) 977.2989, found 977.2975.

Compound 10

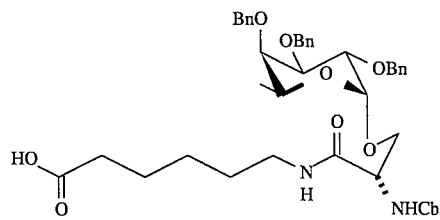

EDAC (1-ethyl-3-(3-dimethylaminopropyl)-carbodiimide; Sigma company); (11.6 mg, 0.060 mmol) and N-hydroxysuccinimide (Aldrich, 6.9 mg, 0.060 mmol) were added to 8 (33.0 mg, 0.050 mmol) in anhydrous dichloromethane (1 mL). The mixture was stirred at room temperature for 3 hours and 6-aminocaproic acid (Sigma company, 6.6 mg, 0.050 mmol), triethylamine (0.5 mL) and DMF (1 mL) were added. After 1 hour, the solvent was evaporated and compound 10 (20 mg, 52%) was obtained after silica gel chromatography. $^1$H NMR (500 MHz, CDCl$_3$) δ 1.10 (d, 3H, J=6.5 Hz, H-6), 1.28–1.57 (m, 6H), 2.25 (m, 2H), 3.12 (m, 2H), 3.50 (dd, 1H, J=3.5, 9.5 Hz), 3.77(m, 2H, H-4), 3.85(dd, 1H, J=3.0, 10.5 Hz, H-3), 3.98 (dd, 1H, J=3.5, 10.0 Hz, H-2), 4.06 (dd, 1H, J=3.0, 9.5 Hz), 4.27 (m, 1H, H-5), 4.59–5.13(m, 8H), 4.77 (d, 1H, J=3.5 Hz, H-1), 7.25–7.41 (m, 20H). HRMS cacld for C$_{44}$H$_{52}$N$_2$O$_{10}$CS (M+Cs$^+$) 901.2676, found 901.2650.

Compound 11

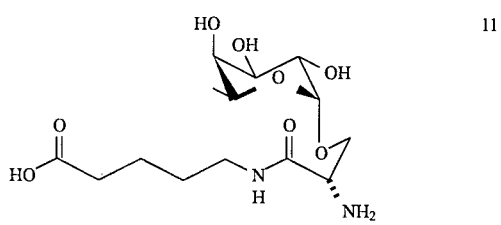

Compound 9 (15 mg, 0.019 mmol) was dissolved in methanol (2 mL) and Pd(OH)$_2$ on carbon (wet, Degussa type E101 NE/W, 5 mg; Aldrich company) was added. The mixture was stirred under hydrogen (1 atm) at room temperature for 12 h. The catalyst was filtered through celite and the filtrate was evaporated to afford 11.10 mg-100% was obtained from compound 9 (24 mg, 0.028 mmol). $^1$H NMR (500 MHz, D$_2$O) δ 1.12 (d, 3H, J=6.5 Hz, H-6), 1.43–1.48 (m, 4H), 2.10–2.13 (m, 2H), 3.14–3.20 (m, 2H), 3.68–3.73 (m, 4H, H-2, H-3, H-4, H-5), 3.76 (dd, 1H, J=3.0, 11.0 Hz), 4.06 (dd, 1H, J=3.0, 11.0 Hz), 4.20 (m, 1H), 4.82 (d, 1H, J=3.5 Hz, H-1). $^{13}$C NMR (D$_2$O, 125 MHz) δ 15.69, 23.61, 28.67, 37.39, 39.93, 53.34, 66.05, 67.59, 68.29, 69.78, 71.94, 98.60, 167.9, 183.4. HRMS calcd for C$_{14}$H$_{27}$N$_2$O$_{10}$ (M+H$^+$) 351.1767, found 351.1769.

Compound 12

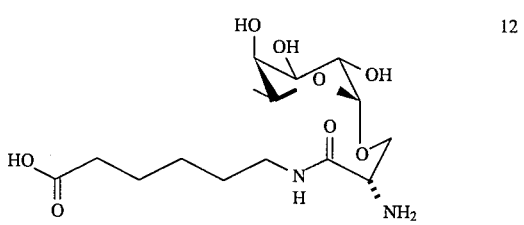

Compound 10 (15 mg, 0.019 mmol) was dissolved in methanol (2 mL) and Pd(OH)$_2$ on carbon (wet, Degussa type E101 NE/W, 5 mg; Aldrich company) was added. The mixture was stirred under hydrogen (1 atm) at room temperature for 12 h. The catalyst was filtered through celite and the filtrate was evaporated to afford 12. Compound 12 (9.5 mg, 100%) was obtained from compound 10 (20 mg, 0.026 mmol). $^1$H NMR (500 MHz, D$_2$O) δ 1.13 (d, 3H, J=6.5 Hz, H-6), 1.25 (m, 2H), 1.44–1.50 (m, 4H), 2.10 (t, 2H, J=7.5 Hz), 3.16 (m, 2H), 3.71 (m, 4H, H-2, H-3, H-4, H-5), 3.74.–3.96 (m, 3H), 4.81 (d, 1H, J=2.5 Hz, H-1). $^{13}$C NMR (125 MHz, D$_2$O) δ 12.22, 15.72, 25.89, 26.46, 28.59, 37.82, 39.97, 42.23, 67.53, 68.31, 69.78, 72.02, 98.89, 154.1, 184.1. HRMS calcd for C$_{15}$H$_{29}$N$_2$O$_8$ (M+H$^+$) 365.1924, found 365.1931.

Compound 13

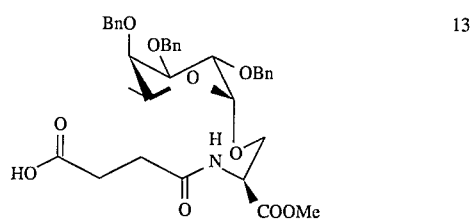

Compound 3 (9.4 mg, 0.015 mmol) was treated with 10% TFA (trifluoracetic acid in CH$_2$Cl$_2$ (2 mL) for 30 min. After the solvent was evaporated, the residue was coevaporated with toluene three times to afford the amine. $^1$H NMR (500 MHz, CDCl$_3$) δ 1.12 (d, 3H, J=6.5 Hz, H-6), 3.50 (m, 2H), 3.67 (m, 2H, H-4 and H-5), 3.72 (s, 3H, OMe), 3.90 (m, 2H, H-3), 4.04 (dd, 1H, J=3.5, 10.0 Hz, H-2), 4.69 (d, 1H, J=3.5 Hz, H-1), 4.59–4.92 (m, 6H), 7.34 (m, 15H). The amine was dissolved in dry dichloromethane (2 mL) and succinic anhydride (15 mg, 0.15 mmol) and triethyl amine (1 mL) were added. The mixture was stirred for 1 hour and the solvent was evaporated. Water was added to the residue and acidified to pH 4 by addition of 1N HCl. The aqueous solution was extracted by CH$_2$Cl$_2$ and the organic fractions were collected and dried over MgSO$_4$. After filtration, the solvent was evaporated and the product 13 (7.0 mg, 74%) was obtained after silica gel chromatography (hexane/Ethylacetate, 1:1→1:2). $^1$H NMR (500 MHz, CDCl$_3$) δ 1.09 (d, 3H, J=6.5 Hz, H-6), 2.35 (m, 2H), 2.60 (m, 2H), 3.54 (dd, 1H, J=3.0 10.0 Hz), 3.67 (m, 1H, H-4), 3.68 (m, 1H, H-5), 3.69 (s, 3H, OMe), 3.86 (dd, 1H, J=2.5, 10.0 Hz, H-3), 4.06 (dd, 1H, J=3.5, 10.0 Hz, H-2), 4.15 (dd, 1H, J=2.5, 10.0 Hz), 4.62–4.97 (m, 7H), 4.69 (d, 1H, J=3.5 Hz, H-1), 7.26–7.40 (m, 15H). HRMS calcd for C$_{35}$H$_{41}$NO$_{10}$Na (M+Na$^+$) 658.2628, found 658.2606.

SCHEME 1

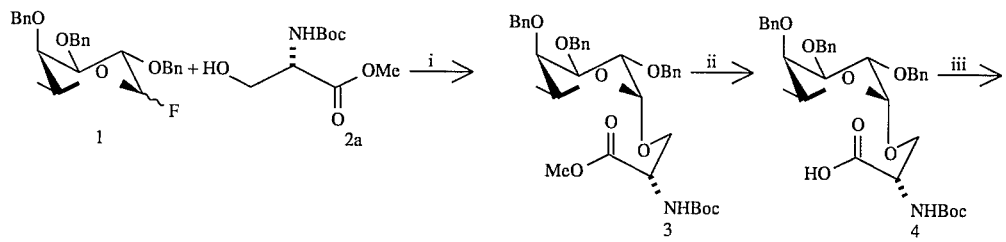

-continued
SCHEME 1
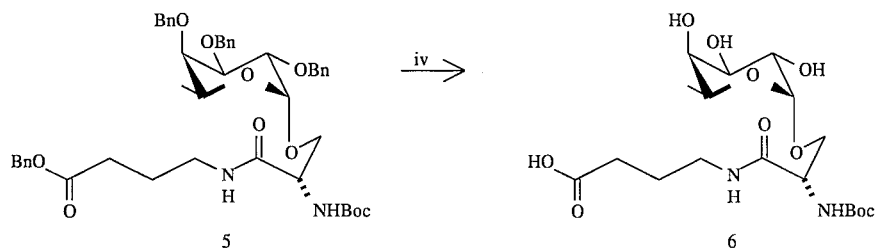
(i) SnCl₂, AgOTf, CH₂Cl₂, 4Å MS (α form, 30%);
(ii) LiOH, MeOH/H₂O (52%);
(iii) EDAC, HOBT, 4-Aminobutyric acid benzyl ester (71%);
(iv) Pd(OH)₂/C, H₂ (100%).
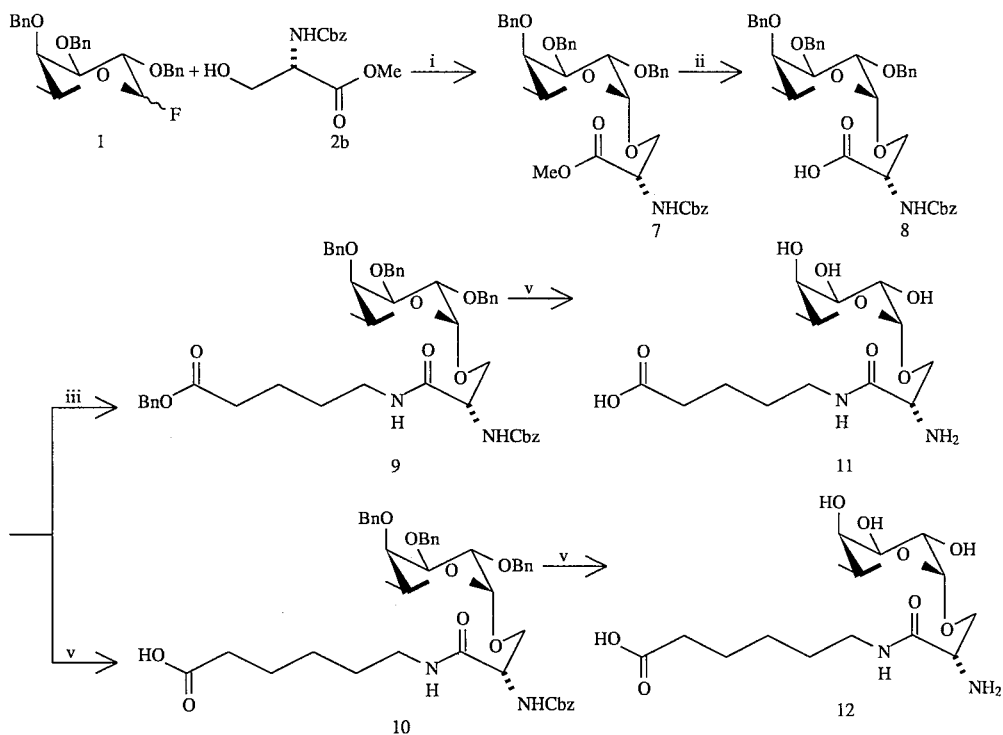
(i) SnCl₂, AgOTf, CH₂Cl₂, 4Å MS (α form, 31%);
(ii) LiOH, MeOH/H₂O (54%);
(iii) EDAC, HOBT, 5-Aminovaleric acid benzyl ester (49%);
(iv) N-Hydroxysuccinimide, EDAC; 6-Aminocaproic acid (52%);
(v) Pd(OH)₂/C, H₂ (100%).

Compound 14

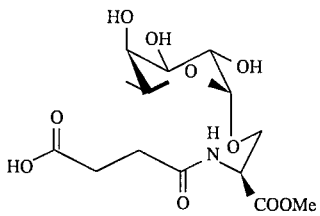

Compound 13 (15 mg, 0.019 mmol) was dissolved in methanol (2 mL) and Pd(OH)$_2$ on carbon (wet, Degussa type E101 NE/W, 5 mg; Aldrich company) was added. The mixture was stirred under hydrogen (1 atm) at room temperature for 12 h. The catalyst was filtered through celite and the filtrate was evaporated to afford 14. Compound 14 (4 mg, 100%) was obtained from compound 13 (7.0 mg, 0.011 mmol). $^1$H NMR (500 MHz, CD$_3$OD) d 1.20 (d, 3H, J=6.5 Hz, H-6), 2.61 (m, 4H), 3.55 (dd, 1H, J=3.0, 10.0 Hz), 3.63 (m, 2H), 3.72 (s, 3H, OMe), 3.76 (m, 2H), 4.17 (dd, 1H, J=3.0, 9.5 Hz), 4.70 (t, J=3.0 Hz, 1H), 4.74 (d, 1H, J=4.0 Hz, H-1). $^{13}$C (125 MHz CD$_3$OD) δ 16.5, 30.0, 31.1, 52.3, 53.7, 67.9, 68.3, 69.8, 71.5, 73.5, 100.2, 144.2, 172.0, 174.5.

Compound 15

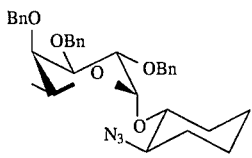

2,3,4-Tri-O-benzyl-L-fucopyranose 1 (L-Fucose was first converted to 2,3,4-tri-O-benzyl-L-fucopyranosyl fluoride from methodology established by Muller et. Al. *Liebigs Ann. Chem.* 1994, 325 and Wong et. Al. *J. Org. Chem.* 1994, 59, 864; 1.9 g, 0.0044 mol) was dissolved in anhydrous dicholomethane at 0° C. and DAST (Aldrich; diethylaminosulfur trifluoride; 1.06 g, 0.0066 mol) was dropped in. After the mixture was stirred at 0° C. for 30 min., the reaction was quenched by the addition of water. The aqueous solution was extracted with dichloromethane and the organic fractions were combined, dried over MgSO$_4$ and filtered. The solvent was evaporated and the fluoride was used for the glycosylation without further purification. 4 Å Molecular sieves, tin (II) chloride (1.67 g, 0.0088 mol) and silver perchloride (1.82 g, 0.0088 mol) were added to a solution of the fluoride in anhydrous dichloromethane (20 mL) at 0° C. The mixture was stirred for 5 min. and (R,R) azidocyclohexanol 2c (0.93 g, 0.0066 mol; from methodology established by Muller et. Al. *Liebigs Ann. Chem.* 1994, 325 and Wong et. Al. *J. Org. Chem.* 1994) was added. The reaction was warmed to room temperature and stirred for 6 hours. The mixture was then filtered through celite and the filtrate was concentrated and applied to silica gel chromatography (hexane/Ethylacetate, 8:1). Compound 15 (2.3 g, 60%) was obtained as a clear oil. $^1$H NMR (500 MHz, CDCl$_3$) δ 1.13 (d, 3H, J=6.5 Hz, H-6), 1.20 (m, 4H), 1.68 (m, 2H), 1.99 (m, 2H), 3.40 (m, 2H), 3.94 (dd, 1H, J=2.5, 10.0 Hz, H-3), 4.06 (m, 2H, H-2 and H-4), 4.14 (m, 1H, H-5), 4.64–4.98 (m, 6H), 4.97 (d, 1H, J=3.0 Hz, H-1), 7.40 (m, 15H) $^{13}$C (125 MHz CDCl$_3$) δ 16.50, 23.28, 23.81, 28.84, 30.50, 64.25, 66.38, 73.12, 73.15, 74.53, 75.71, 75.99, 77.53, 79.17, 93.18, 127.8 (m), 138.4, 138.4, 138.7. HRMS cacld for C$_{33}$H$_{39}$N$_3$O$_5$ (M+Cs) 690, found 690.

Compound 16

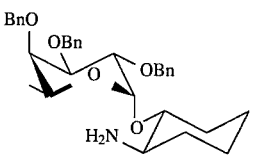

a) Triphenylphosphine Reduction

Compound 15 (1.3 g, 2.33 mmol) was dissolved in tetrahydrofuran (10 mL, containing 1% H$_2$O) and triphenylphosphine (638 mg, 2.56 mmol) was added. The mixture was stirred at room temperature for 5 h and the solvent was evaporated. The residue was applied on a silica gel column and the product was eluted with CHCl$_3$/methanol (50:1→30:1). Compound 16 (730 mg, 59%) was obtained as a syrup.

b) LAH Reduction

LAH (lithium aluminum hydride; 170 mg, 4.5 mmol) was added to compound 15 (250 mg, 0.45 mmol) in anhydrous ethyl ether (3 mL) at 0° C. The mixture was warmed to room temperature and stirred for 4 h. Ethyl acetate (15 mL), water (350 mg), 15% NaOH (350 mg) and water (1.2 g) were added subsequently. The precipitation was filtered through celite and the solvent was evaporated. Compound 16 (334 mg, 100%) was obtained as a clear oil. $^1$H NMR (500 MHz, CDCl$_3$) δ 1.12 (d, 3H, J=6.5 Hz, H-6), 1.20 (m, 4H), 1.85 (m, 4H), 2.76 (m, 1H), 3.20 (m, 1H), 3.69 (m, 1H, H-4), 3.95 (dd, 1H, J=2.5, 10.0 Hz, H-3), 4.03 (m, 1H, H-5), 4.07 (dd, 1H, J=4.0, 10.0 Hz, H-2), 4.65–5.00 (m, 6H), 5.03 (d, 1H, J=4.0 Hz, H-1), 7.34 (m, 15H). $^{13}$C NMR (125 MHz, CDCl$_3$) δ 16.66, 24.45, 24.53, 29.08, 33.73, 54.33, 66.42, 73.04, 73.21, 74.65, 76.05, 77.50, 79.32, 81.05, 93.61, 127.3, 127.4, 127.5, 127.5, 127.9, 128.1, 128.2, 128.3, 128.3, 138.4, 138.5, 138.8. HRMS calcd for C$_{33}$H$_{41}$NO$_5$ (M+H$^+$) 532.3063, found 532.3076.

Compound 17

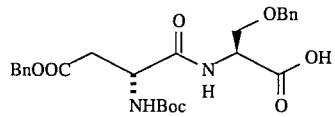

O-Benzyl-N-Boc-L-aspartic acid (from methodology established by Muller et. Al. *Liebigs Ann. Chem.* 1994, 325 and Wong et. Al. *J. Org. Chem.* 1994; 1.08 g, 3.34 mmol) was dissolved in anhydrous dichloromethane and EDAC (1-ethyl-3-(3-dimethylaminopropyl)-carbodiimide; Sigma company; 640.3 mg, 3.34 mmol) and N-hydroxysuccinimide (384.4 mg, 3.34 mmol) were added. The mixture was stirred at 4° C. for 12 h and the solvent was evaporated. The product, O-benzyl-N-Boc-aspartic N-hydroxy succinimide ester (491 mg, 35%), was obtained by silica gel chromatography (Ethylacetate/hexane, 1:1.5→1:1). $^1$H NMR (500 MHz, CDCl$_3$) δ 1.44 (s, 9H, tBoc), 2.78 (m, 4H), 2.97 (dd, 1H, J=4.5, 17.5 Hz), 3.12 (dd, 1H, J=5.0, 17.5 Hz), 5.01 (m, 1H), 5.17 (m, 1H), 5.74 (d, 1H, J=9.0 Hz, NH), 7.35 (m, 5H). $^{13}$C NMR (125 MHz, CDCl$_3$) δ 25.33, 27.96, 36.51, 48.37, 66.87, 80.43, 128.3 (m), 135.1, 154.6, 166.8, 168.5, 169.8. HRMS calcd for C$_{20}$H$_{24}$N$_2$O$_8$Cs (M+Cs$^+$) 553.0587, found 553.0573. O-Benzyl-N-Boc-aspartic N-succinimide ester (603 mg, 1.44 mmol) and O-benzyl-serine (Sigma company; 281 mg, 1.44 mmol) were dissolved in DMF (dimethylformamide; 2 mL) and Et$_3$N (1 mL) was added. The mixture was stirred at room temperature for 1 hour. After evaporation of the solvent, the product 17 (367 mg, 51%) was obtained after silica gel chromatography (CHCl$_3$). $^1$H NMR (500 MHz, CD$_3$OD) δ 1.40 (S, 9H), 2.75 (dd, 1H, J=8.0, 16.5 Hz), 2.90 (dd, 1H, J=5.5, 16.5 Hz), 3.72 (dd, 1H, J=3.0, 9.5 Hz), 3.89 (dd, 1H, J=4.0, 9.5 Hz), 4.46 (d, 2H, J=6.0 Hz), 4.60 (m, 2H), 5.08 (d, 2H, J=5.5 Hz), 7.29 (m, 10H). Unit MS calcd for $C_{26}H_{32}N_2O_8Na$ (M+Na$^+$) 523, found 523.

Compound 18

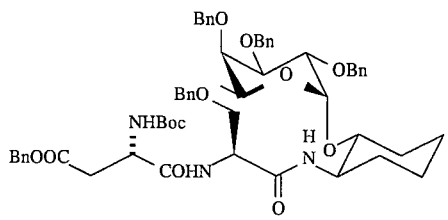
18

Acid 17 (141 mg, 0.29 mmol), EDAC (1-ethyl-3-(3-dimethylaminopropyl)-carbodiimide; Sigma company; 81 mg, 0.42 mmol) and HOBT (1-hydroxybenzotriazole hydrate; Aldrich company; 57 mg, 0.42 mmol) were dissolved in dichloromethane (2 mL) at room temperature and stirred for 5 min before compound 16 (148 mg, 0.56 mmol) was added. The mixture was stirred at room temperature for 3 hours and the solvent was evaporated. The residue was applied to a silica gel column (hexane/Ethylacetate, 1.5:1→1:1) and compound 18 (122 mg, 43%) was obtained as a syrup. $^1$H NMR (500 MHz, CDCl$_3$) δ 1.20 (d, 3H, J=6.5 Hz, H-6), 1.08–1.60 (m, 4H), 1.44 (s, 9H), 1.73 (m, 1H), 1.94 (m, 3H), 2.71 (m, 1H), 3.05 (m, 1H), 3.65 (dd, 1H, J=3.5, 9.5 Hz), 3.76 (m, 1H, H-4), 3.89 (dd, 1H, J=3.0, 9.5 Hz), 3.98 (dd, 1H, J=2.5, 10.0 Hz, H-3), 4.04 (dd, 1H, J=3.5, 10.0 Hz, H-2), 4.10 (m, 1H, H-5), 4.44 (m, 1H), 4.61 (m, 1H), 4.68 (m, 1H), 4.95 (d, 1H, J=3.5 Hz, H-1), 4.45–5.17 (m, 10H), 5.68 (m, 1H), 7.33 (m, 25H). $^{13}$C NMR (125 MHz, CDCl$_3$) δ 16.72, 23.34, 23.82, 28.20, 36.29, 36.59, 50.42, 50.65, 52.45, 52.58, 52.82, 66.69, 66.72, 66.78, 69.26, 73.09, 73.18, 74.80, 75.98, 75.98, 77.73, 79.35, 94.52, 128.0 (m), 135.2, 135.3, 137.5, 183.6, 139.0, 155.3, 169.6, 170.2, 170.6, 171.9. HRMS cacld for $C_{59}H_{71}N_3O_{12}Cs$ (M+Cs$^+$) 1146.4092, found 1146.4035

Compound 19

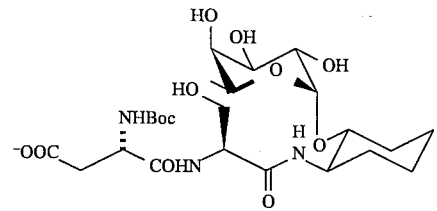
19

Compound 18 (122 mg, 0.12 mmol) was dissolved in methanol (2 mL) and Pd(OH)$_2$ on carbon (wet, Degussa type E101 NE/W, 20 mg) was added and the mixture was stirred under hydrogen (1 atm) for 12

SCHEME 2

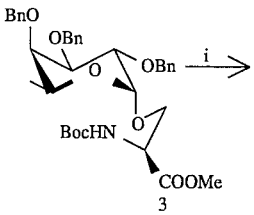
3

-continued
SCHEME 2

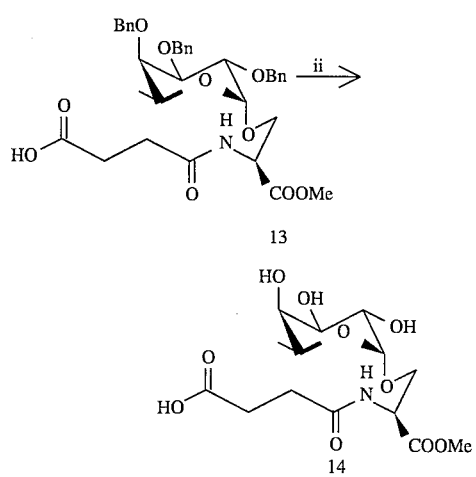

(i) TFA; Succinic anhydride (45%);

(ii) Pd(OH)$_2$/C, H$_2$ (100%).

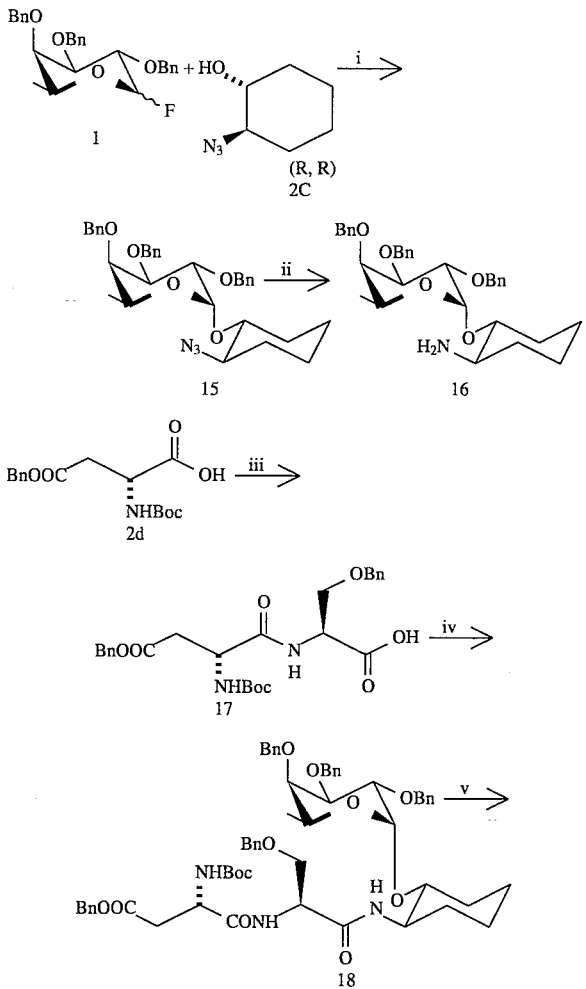

-continued
SCHEME 2

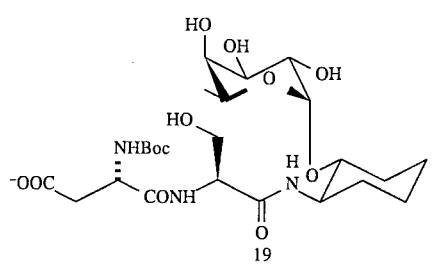

(i) SnCl$_2$, AgClO$_4$, CH$_2$Cl$_2$, 4Å MS (α form, 60%);

(ii) PPh$_3$ (59%) or LAH (100%);

(iii) N-Hydroxysuccinimide, EDAC (35%); O-Benzyl-L-Serine, Et$_3$N (51%);

(iv) EDAC, HOBT, 19 (43%);

(v) Pd(OH)$_2$/C, H$_2$ (59%).

hours. The catalyst was filtered through celite and the product was purified by silica gel chromatography (CHCl$_3$/methanol, 3:1) and biogel P2 chromatography (H$_2$O). Compound 19 (40 mg, 59%) was obtained after purification. $^1$H NMR (500 MHz, D$_2$O) δ 1.48 (d, 3H, J=7.0 Hz, H-6), 1.47–1.74 (m, 4H), 1.74 (s, 9H), 2.00–2.11 (m, 3H), 2.47 (m, 1H), 3.64 (s, 1H, H-4), 3.76 (m, 1H), 3.97–4.25 (m, 6H, H-2, H-3, H-5), 4.65–4.74 (m, 2H), 5.31 (d, 1H, J=3.5 Hz, H-1). $^{13}$C NMR (125 MHz, D$_2$O) δ 15.80, 23.73, 24.51, 28.18, 30.18, 31.60, 39.68, 49.47, 53.42, 55.89, 55.99, 62.39, 67.12, 68.42, 70.08, 72.39, 94.38, 94.65, 170.9, 171.1, 174.7, 178.1. HRMS calcd for C$_{24}$H$_{41}$N$_3$O$_{12}$Cs (M+Cs$^+$) 696.1745, found 696.1717.

Compounds 20 and 21

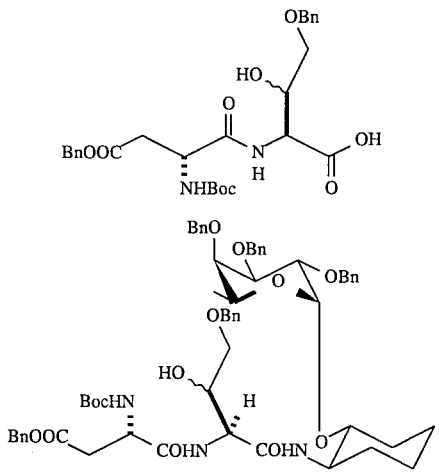

O-Benzyl-N-Boc-aspartic-N-hydroxylsuccinamide ester (from methodology established by Muller et. Al. *Liebigs Ann. Chem.* 1994, 325 and Wong et. Al. *J. Org. Chem.* 1994, 93.3 mg, 0.222 mmol) and (2S, 3S/3R)-2-amino-3-hydroxy-4-benzyloxy butyric acid (24, Wong et. Al. *J. Org. Chem.* 1994; 50 mg, 0.222 mmol) were dissolved in DMF (dimethylformamide 2 mL) and triethylamine (500 μL) was added. The mixture was stirred for 1 h at room temperature before the solvent was evaporated. Water was added to the residue and acidified to pH 4 by 1N HCl. The aqueous solution was extracted with ethyl ether and the organic fractions were combined and dried over anhydrous MgSO$_4$. After filtration, the filtrate was concentrated and applied to silica gel column (CHCl$_3$). Compound 20 (76%) was obtained as a syrup, which was dissolved in anhydrous dichloromethane (2 mL). EDAC (49 mg, 0.256 mmol) and HOBT (33 mg, 0.256 mmol) were added to the solution and the mixture was stirred for 5 min.before amine 16 (90 mg, 0.169 mmol) was added. The reaction was stirred at room temperature for 3 h and the solvent was evaporated. Silica gel chromatography (Ethylacetate/hexane, 1:1→2:1 ) afforded compound 21 (79.3 mg, 45%) as a syrup. $^1$H NMR (500 MHz, CDCl$_3$) δ 1.15 (d, 3H, J=6.5 Hz, H-6), 1.08–1.60 (m, 4H), 1.70 (m, 1H), 1.90 (m, 3H), 2.76 (dd, 1H, J=6.0, 17.0 Hz), 3.02 (dd, 1H, J=5.0, 17.0 Hz), 3.42 (dd, 1H, J=3.5, 10.0 Hz), 3.54 (dd, 1H, J=5.5, 17.0 Hz), 3.63 (dd, 1H, J=5.0, 10.0 Hz), 3.73 (m, 1H), 3.76 (m, 1H, H-4), 3.93 (dd, 1H, J=2.5, 10.0 Hz, H-3), 4.02 (dd, 1H, J=5.0, 10.0 Hz, H-2), 4.04 (m, 1H, H-5), 4.43 (m, 1H), 4.74 (m, 1H), 4.90 (d, 1H, J=3.5 Hz, H-1), 4.30–5.18 (m, 10H), 5.47 (m, 1H), 7.30 (m, 25H). HRMS calcd for C$_{60}$H$_{73}$N$_3$O$_{13}$Cs (M+Cs$^+$) 1176.4198, found 1176.4141.

Compound 22

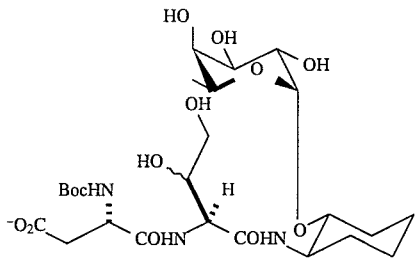

Pd(OH)$_2$ on carbon (wet, Degussa type E101 NE/W, 10 mg) was added to compound 21 (40 mg, 0.038 mmol) in methanol (2 mL). The mixture was stirred under hydrogen (1 atm) for 6 hours. After the catalyst was filtered, the solvent was evaporated and compound 22 (12 mg, 53%) was obtained by silica gel chromatography (CHCl$_3$/methanol, 3:2) and bio gel P2 chromatography (H$_2$O). $^1$H NMR (500 MHz, D$_2$O) δ 1.12 (d, 3H, J=6.5 Hz, H-6), 1.08–1.26 (m, 4H), 1.39 (s, 9H), 1.65–1.80 (m, 3H), 2.14 (m, 1H), 2.74 (m, 2H), 3.39–3.88 (m, 9H), 4.37 (m, 2H), 4.98 (d, 1H, J=3.5 Hz, H-1). $^{13}$C NMR (125 MHz, D$_2$O) δ 15.82, 23.70, 24.58, 28.03, 29.30, 31.78, 37.32, 52.05, 53.40, 55.55, 62.93, 67.14, 68.32, 69.95, 71.99, 72.25, 76.23, 82.21, 94.06, 157.6, 170.8, 173.4, 175.8. HRMS calcd for C$_{25}$H$_{43}$N$_3$O$_{13}$Cs (M+Cs$^+$) 726.1850, found 726.1832.

Compound 23

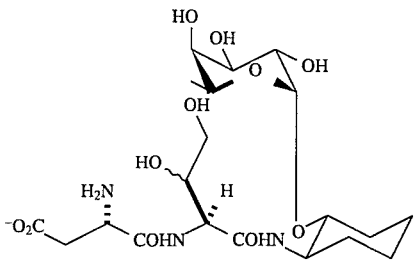

Pd(OH)$_2$ on carbon (wet, Degussa type E101 NE/W, 10 mg) was added to compound 21 (40 mg, 0.038 mmol) in methanol (2 mL). The mixture was stirred under hydrogen (1 atm) for 18 hours. After the catalyst was filtered, the solvent was evaporated and compound 23 (9.3 mg, 49%) was obtained by silica gel chromatography (CHCl$_3$/methanol, 3:2) and bio gel P2 chromatography (H$_2$O). $^1$H NMR (500 MHz, D$_2$O) δ 1.15 (d, 3H, J=6.5 Hz, H-6), 1.10–1.40 (m, 4H), 1.66–1.85 (m, 3H), 2.16 (m, 1H), 2.59 (dd, 1H, J=8.5, 17.5 Hz), 2.72 (dd, 1H, J=5.0, 17.5 Hz), 3.40 (m, 1H), 3.51 (dd, 1H, J=6.0, 12.0 Hz), 3.56 (dd, 1H, J=3.5, 10.0 Hz, H-3), 3.60 (m, 1H), 3.64 (dd, 1H, J=4.0, 10.0 Hz, H-2), 3.69 (m, 1H, H-4), 3.73 (m, 1H), 3.85 (m, 1H), 3.91 (m, 1H, H-5), 4.15 (m, 1H), 4.40 (d, 1H, J=7.0 Hz), 5.00 (d, 1H, J=4.0 Hz, H-1). $^{13}$C NMR (125 MHz, D$_2$O) δ 15.77, 23.69, 24.62, 29.06, 31.80, 38.41, 51.47, 53.40, 55.59, 62.76, 67.09, 68.35, 69.91, 71.79, 72.24, 75.68, 93.63, 170.6, 176.8, 176.8. HRMS calcd for C$_{20}$H$_{35}$N$_3$O$_{11}$Na (M+Na$^+$) 516.2169, found 516.2169.

SCHEME 3

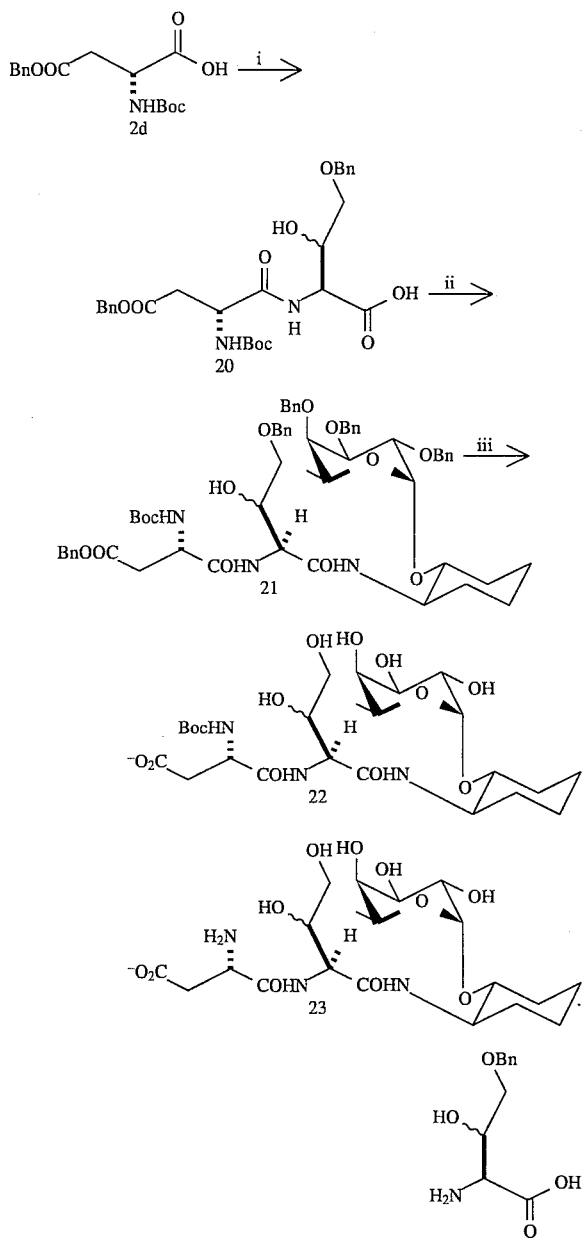

(i) N-Hydroxysuccinimide, EDAC (35%); 23, Et$_3$N (76%);

(iv) EDAC, HOBT, 20 (45%);

(v) Pd(OH)$_2$/C, H$_2$ (6, 53%; 7, 49%).

Compound 25

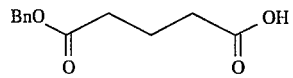

Glutaric anhydride (5.7 g, 0.05 mol), benzyl alcohol (5.41 g, 5.18 mL, 0.05 mol) and DMAP (500 mg; 4-dimethylaminopyridine) were dissolved in pyridine (8 mL) and the mixture was stirred at 50° C. for 12 h. After the evaporation of the solvent, saturated NaHCO$_3$ was added and the aqueous solution was washed twice with ethyl acetate. The resulting aqueous solution was acidified to pH 4 by 1N HCl and extracted with ethyl ester. The organic fractions were combined and dried over MgSO$_4$. After filtration and evaporation of the solvent, compound 25 (7.0 g, 63%, Rf=0.7, Ethylacetate/hexane, 2:1) was obtained as a syrup. $^1$H NMR (500 MHz, CDCl$_3$) δ 1.85 (m, 2H), 2.31 (m, 2H), 2.37 (t, 2H, J=7.5 Hz), 5.07 (s, 2H), 7.29 (m, 5H).

Compound 26

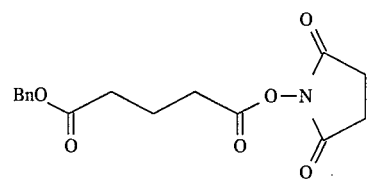

Compound 25 (500 mg, 2.25 mmol) and EDAC (648 mg, 3.38 mmol; Sigma) were dissolved in anhydrous dichloromethane (3 mL) and N-hydroxysuccinimide (389 mg, 3.38 mmol) was added. The mixture was stirred at room temperature for 12 h and the solvent was evaporated. Product 26 (330 mg, 46%) was obtained after silica gel chromatography (CHCl$_3$). $^1$H NMR (500 MHz, CDCl$_3$) δ 2.04 (m, 2H), 2.49 (ddd, 2H, J=2.5, 7.5, 9.5 Hz), 2.67 (ddd, 2H, J=2.5, 7.5, 10.0 Hz), 2.76 (m, 4H), 5.11 (s, 2H), 7.34 (m, 5H).

Compound 27

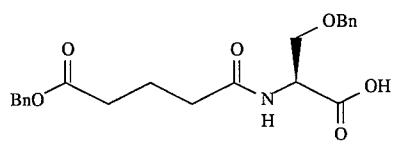

Compound 26 (330 mg, 1.03 mmol) and O-benzyl-L-serine (250 mg, 1.28 mmol, from methodology established by Wong et. Al. *J. Org. Chem.* 1994) were dissolved in anhydrous DMF (2 mL) and anhydrous triethylamine (1 mL) was added. The mixture was stirred at room temperature for 1 h and the solvent was evaporated. Water was added to the resulting residue and the suspension was acidified to pH 4 by 1N HCl. The aqueous suspension was extracted with ethyl ether and the organic fractions were combined and dried over MgSO$_4$. After filtration, the solvent was evaporated and compound 27 (300 mg, 73%) was obtained as a syrup. $^1$H NMR (500 MHz, CDCl$_3$) δ 1.95 (m, 2H), 2.29 (m, 2H), 2.40 (m, 2H), 3.69 (dd, 1H, J=3.5, 9.5 Hz), 3.92 (dd, 1H, J=3.0, 9.5 Hz), 4.49 (m, 2H), 4.76 (m, 1H), 5.09 (m, 2H), 6.77 (d, 1H, J=8.0 Hz, N—H), 7.30 (m, 10H). $^{13}$C NMR (125 MHz, CDCl$_3$) δ 20.58, 32.98, 34.83, 52.39, 66.08, 69.45, 73.10, 128.0 (m), 135.7, 137.2, 172.7, 172.8, 172.9. HRMS calcd for C$_{22}$H$_{25}$NO$_6$Cs (M+Cs$^+$) 532.0736, found 532.0760.

Compounds 28 and 29

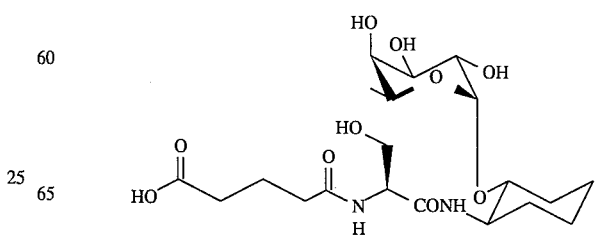

27
-continued

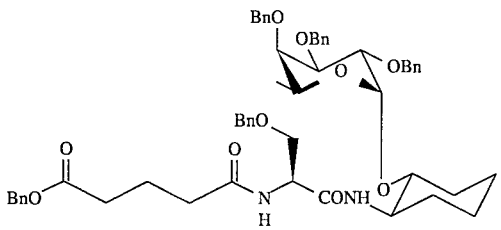

Compound 27 (300 mg, 0.73 mmol), EDAC (172 mg, 0.90 mmol) and HOBT (118 mg, 0.9 mmol) were dissolved in anhydrous dichloromethane and compound 16 (350 mg, 0.66 mmol) was added. The mixture was stirred at room temperature for 3 hours and the solvent was evaporated. Compound 28 (297 mg, 49.3%) was obtained by silica gel chromatography. Compound 28 (40 mg, 0.04 mmol) was dissolved in methanol and Pd(OH)$_2$ on carbon (wet, Degussa type E101 NE/W, 10 mg) was added. The suspension was stirred under hydrogen (1 atm) for 6 hours and the catalyst was filtered through celite. After the solvent was evaporated, the crude product was purified by bio gel P2 chromatography (H$_2$O) and compound 29 (12 mg, 59%) was obtained. $^1$H NMR (500 MHz, D$_2$O) d 1.12 (d, 3H, J=6.5 Hz, H-6), 1.18 (m, 5H), 1.66 (m, 3H), 1.77 (m, 2H), 2.15 (t, 2H, J=7.5 Hz), 2.28 (m, 3H), 3.42 (m, 1H), 3.66 (dd, 1H, J=3.5, 8.0 Hz, H-2), 3.69 (m, 2H, H-3, H-4), 3.74 (m, 2H), 3.85 (m, 1H, H-5), 4.37 (t, 1H, J=5.5 Hz), 5.02 (d, 1H, J=3.5 Hz, H-1). $^{13}$C NMR (125 MHz, CDCl$_3$) δ 15.81, 22.64, 23.62, 24.59, 28.98, 31.54, 35.63, 37.05, 53.47, 55.86, 61.77, 67.09, 68.29, 69.90, 72.26, 75.44, 93.52, 171.9, 176.8. HRMS calcd for C$_{20}$H$_{34}$N$_2$O$_{10}$Na (M+Na$^+$) 485.2111, found 485.2127.

Compound 30

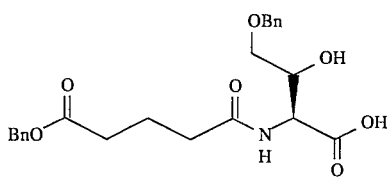

Compound 26 (620 mg, 1.94 mmol) and 2S-2-amino-3-hydroxy-4-benzyloxy butyric acid (24, from methodology established by Muller et. Al. *Liebigs Ann. Chem.* 1994, 325 and Wong et. Al. *J. Org. Chem.* 1994; 500 mg, 2.23 mmol) were dissolved in DMF/H$_2$O (DMF=dimethylformamide; 5:1, 5 mL) and triethylamine (1 mL) was added. The mixture was stirred at room temperature for 1 hour and the solvent was evaporated. Water was added and the solution was acidified to pH 4 by 1N HCl. The aqueous suspension was extracted with ethyl ether and the organic fractions were combined and dried over anhydrous MgSO$_4$. After filtration, the solvent was evaporated and compound 30 (800 mg, 89.5%) was obtained as a syrup. $^1$H NMR (500 MHz, CDCl$_3$) δ 1.91 (m, 2H), 2.24 (m, 2H), 2.37 (t, 2H, J=7.5 Hz), 3.68 (dddd, 1H, J=2.0, 7.0, 9.0, 14.0 Hz ), 4.45 (abs, 1H, J=11.5 Hz,=32 Hz), 4.52 (abs, 1H, J=11.5 Hz,=32 Hz), 4.71 (dd, 1H, J=3.0, 7.0 Hz), 5.09 (s, 2H), 7.32 (m, 10H). $^{13}$C NMR (125 MHz, CDCl$_3$) δ 20.48, 33.09, 34.71, 36.63, 66.11, 70.69, 70.80, 73.21, 128.1 (m), 135.7, 137.5, 171.3, 172.9, 173.5.

28
SCHEME 4

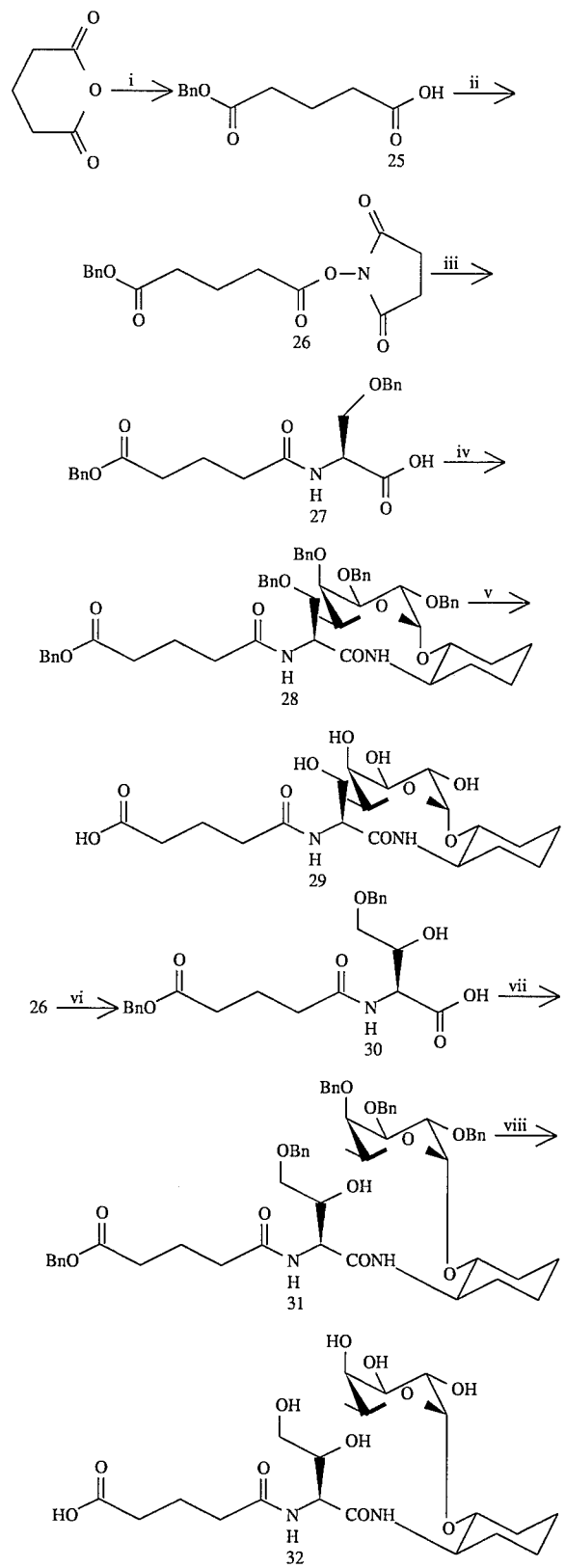

(i) BnOH, Py, DMAP, 50° C. (63%);

(ii) N-hydroxysucciniamide, CH$_2$Cl$_2$ (46%);

(iii) O-Benzyl-L-Serine, DMF, Et$_3$N (73%);

(iv) EDAC, HOBT, 20, CH$_2$Cl$_2$ (49%);

(v) Pd(OH)$_2$/C, H$_2$ (59%);

(vi) 23, DMF/H$_2$O (5:1), Et$_3$N (89.5%);

(vii) 20, EDAC, HOBT, CH$_2$Cl$_2$ (55.2%);

(viii) Pd(OH)$_2$/C, H$_2$ (67%)

Compound 31

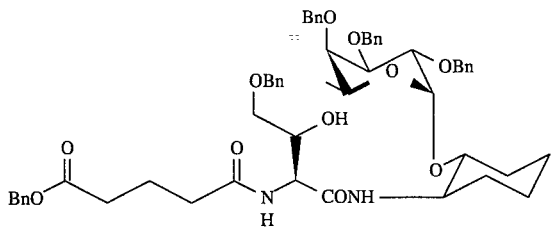

Compound 30 (461 mg, 1.0 mmol), EDAC (287 mg, 1.5 mmol) and HOBT (196 mg, 1.5 mmol) were dissolved in anhydrous dichloromethane and compound 16 (531 mg, 1.0 mmol) was added. The mixture was stirred at room temperature for 3 hours and the solvent was evaporated. Product 31 (520 mg, 55.2%) was obtained as a syrup after silica gel chromatography. $^1$H NMR (500 MHz, CDCl$_3$) δ 1.12 (d, 1H, J=6.5 Hz, H-6), 1.20 (m, 4H), 1.54 (m, 1H), 1.70 (m, 1H), 1.93 (m, 4H), 2.20 (m, 3H), 2.36 (t, 2H, J=7.0 Hz), 3.37 (dd, 1H, J=7.5, (0.5 Hz), 3.46 (dd, 1H, J=6.0, 9.5 Hz), 3.62 (m, 1H, H-4), 3.83 (m, 1H), 3.91 (dd, 1H, J=2.5, 10.0 Hz, H-3), 3.94 (m, 1H, H-5), 4.00 (d, 1H, J=3.5, OH), 4.01 (dd, 1H, J=3.5, 10.0 Hz, H-2), 4.23 (m, 1H), 4.46 (dd, 1H, J=2.0, 6.0 Hz), 4.39–5.10 (m, 10H), 4.93 (d, 1H, J=3.5 Hz, H-1), 7.29 (m, 25H). $^{13}$C NMR (125 MHz, CDCl$_3$) δ 16.58, 20.61, 23.19, 29.21, 30.75, 33.07, 34.97, 52.13, 53.14, 66.28, 66.78, 69.01, 69.43, 73.00, 73.13, 73.35, 74.75, 75.97, 77.15, 77.81, 79.11, 94.58, 128.0 (m), 135.7, 137.5, 138.6, 138.6, 138.9, 170.7, 172.6, 173.0. HRMS calcd for C$_{56}$H$_{66}$N$_2$O$_{11}$Cs (M+Cs$^+$) 1075.3721, found 1075.3760.

Compound 32

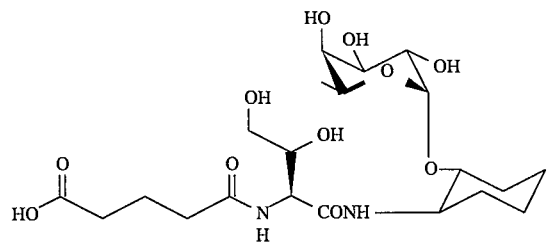

Compound 31 (60 mg, 0.064 mmol) was dissolved in ethylacetate/H$_2$O (1:1) and Pd(OH)$_2$ on carbon (wet, Degussa type E101 NE/W, 10 mg) was added. The suspension was stirred at room temperature under hydrogen (1 atm) for 6 hours. After the catalyst was filtered, the solvent was evaporated and the product was purified by bio gel P2 chromatography (H$_2$O). Compound 32 (21 mg, 67%) was obtained after purification. S isomer: $^1$H NMR (500 MHz, D$_2$O) δ 1.10 (d, 3H, J=6.5 Hz, H-6), 1.20 (m, 4H), 1.75 (m, 6H), 2.16 (m, 1H), 2.56 (t, 2H, J=7.5 Hz), 2.33 (m, 2H), 3.41 (m, 1H), 3.43 (m, 2H), 3.63 (m, 2H, H-2 and H-3), 3.69 (m, 1H, H-4), 3.78 (m, 1H, H-5), 4.09 (ddd, 1H, J=2.5, 6.0, 8.5 Hz), 4.46 (d, 1H, J=2.5 Hz), 5.02 (d, 1H, J=3.0 Hz, H-1). $^{13}$C NMR (125 MHz, D$_2$O) δ 15.85, 21.96, 23.71, 24.60, 28.84, 31.41, 35.38, 35.45, 53.67, 55.19, 62.73, 67.13, 68.26, 69.88, 71.65, 72.22, 75.19, 93.31, 172.3, 176.6. HRMS calcd for C$_{21}$H$_{36}$N$_2$O$_{11}$Cs (M+Cs$^+$) 625.1373, found 625.1355.

Compound 33

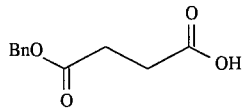

Succinic anhydride (1.0 g, 0.01 mol), benzyl alcohol (1.08 g, 1.03 mL, 0.01 mol) and DMAP (200 mg) were dissolved in pyridine (3 mL) and the mixture was stirred at 50° C. for 12 h. After the evaporation of the solvent, saturated NaHCO$_3$ was added and the aqueous solution was washed twice with ethyl acetate. The resulting aqueous solution was acidified to pH 4 by 1N HCl and extracted with ethyl ether. The organic fractions were combined and dried over MgSO$_4$. After filtration and evaporation of the solvent, compound 33 (1.01 g, 48.6%, Rf=0.4, ethylacetate/hexane, 1:1) was obtained as a syrup. $^1$H NMR (500 MHz, CDCl$_3$) δ 2.59 (m, 4H), 5.10 (s, 2H), 7.31 (m, 5H). $^{13}$C NMR (125 MHz, CDCl$_3$) δ 29.67, 30.01, 67.35, 129.2 (m), 137.5, 174.0, 175.9. HRMS calcd for C$_{11}$H$_{13}$O$_4$ (M+H$^+$) 209.0814, found 209.0806.

Compound 34

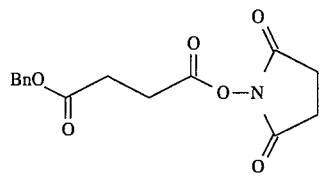

Compound 33 (500 mg, 2.4 mmol) and EDAC (690 mg, 3.6 mmol) were dissolved in anhydrous dichloromethane (3 mL) and N-hydroxysuccinimide (553.4 mg, 4.81 mmol) was added. The mixture was stirred at room temperature for 12 h and the solvent was evaporated. Product 34 (250 mg, 34%, Rf=0.3, Ethylacetate/Hexane, 1:1) was obtained after silica gel chromatography (CHCl$_3$). $^1$H NMR (500 MHz, CDCl$_3$) δ 2.77 (m, 6H), 2.95 (t, 2H, J=7.0 Hz), 5.14 (s, 2H), 7.34 (m, 5H). $^{13}$C NMR (125 MHz, CDCl$_3$) δ 25.38, 26.06, 28.53, 66.68, 128.3 (m), 135.4, 167.6, 169.0, 170.7. HRMS calcd for C$_{15}$H$_{15}$NO$_6$Na (M+Na$^+$) 328.0797, found 328.0785.

Compound 35

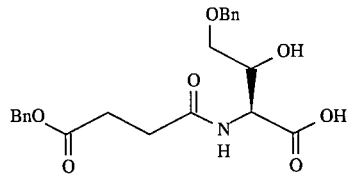

Compound 34 (250 mg, 0.82 mmol) and 24 (150 mg, 0.667 mmol) were dissolved in DMF/H$_2$O (5:1, 2 mL) and triethylamine (0.5 mL) was added. The mixture was stirred at room temperature for 1 h and the solvent was evaporated. Water was added to the resulting residue and the suspension was acidified to pH 4 by 1N HCl. The aqueous suspension was extracted with ethyl ether and the organic fractions were combined and dried over MgSO$_4$. After filtration, the solvent was evaprated and compound 35 (240 mg, 87%) was obtained as a syrup. $^1$H NMR (500 MHz, CDCl$_3$) δ 2.50 (m 2H), 2.67 (m, 2H), 3.58 (dd, 1H, J=5.5, 10.0 Hz), 3.64 (dd, 1H, J=5.5, 10.0 Hz), 4.29 (m, 1H), 4.47 (d, 1H, J=11.5 Hz), 4.53 (d, 1H, J=11.5 Hz), 4.72 (dd, 1H, J=3.5, 7.0 Hz), 5.12

(m, 2H), 6.93 (d, 1H, J=7.0 Hz, N—H), 7.32 (m, 10H). $^{13}$C NMR (125 MHz, CDCl$_3$) δ 28.98, 29.31, 30.53, 31.63, 36.74, 56.25, 66.57, 70.77, 70.81, 73.38, 135.5, 137.6, 163.1, 171.7, 172.6, 172.8. HRMS calcd for C$_{22}$H$_{25}$NO$_7$Cs (M+Cs$^+$) 548.0685, found 548.0671.

Compound 36 and 37

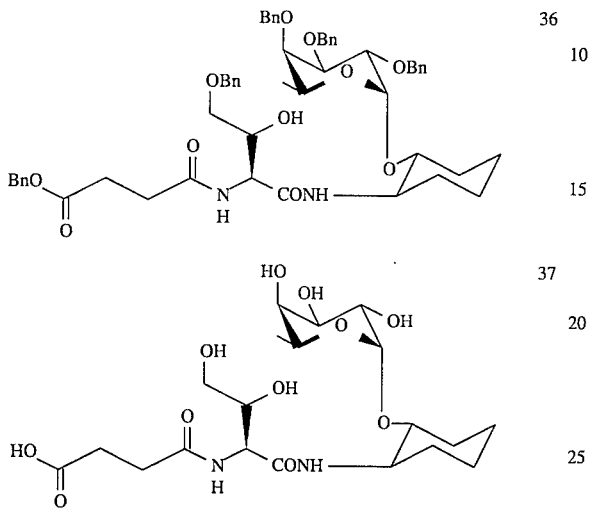

Compound 35 (240 mg, 0.58 mmol), EDAC (166 mg, 0.87 mmol) and HOBT (113 mg, 0.87 mmol) were dissolved in anhydrous dichloromethane and compound 16 (307 mg, 0.58 mmol) was added. The mixture was stirred at room temperature for 3 hours and the solvent was evaporated. Product 36 (280 mg, 52.2%) was obtained as a syrup after silica gel chromatography (Ethylacetate/Hexane, 1:1). R and S isomers could not be seperated. HRMS calcd for C$_{55}$H$_{64}$N$_2$O$_{11}$Cs (M+Cs$^+$) 1061.3564, found 1061.3589.

Compound 36 ( 150 mg, 0.16 mmol) was dissolved in ethylacetate/H$_2$O (1:1) and Pd(OH)$_2$ on carbon (wet, Degussa type E101 NE/W, 20 mg) was added. The suspension was stirred at room temperature under hydrogen (1 atm) for 6 hours. After the catalyst was filtered, the solvent was evaporated and the product was purified by bio gel P2 chromatography (H$_2$O). Compound 37 (51 mg, 65.4%, S/R, 4:1) was obtained after purification.

S isomer (Major): $^1$H NMR (500 MHz, D$_2$O) δ 1.09 (d, 3H, J=6.5 Hz, H-6), 1.25 (m, 3H), 1.45 (m, 1H), 1.65 (m, 3H), 2.18 (m, 1H), 2.57 (m, 2H), 2.63 (m, 2H), 3.40 (m, 1H), 3.47 (d, 2H, J=6.5 Hz), 3.72 (m, 5H, H-2, H-3, H-4 and H-5), 4.22 (ddd, 1H, J=2.0, 6.5, 6.5 Hz), 4.49 (d, 1H, J=2.0 Hz), 5.03 (d, 1H, J=3.0 Hz, H-1) $^{13}$C NMR (125 MHz, D$_2$O) δ 15.83, 23.61, 24.66, 28.72, 30.19, 30.89, 31.37, 53.57, 54.96, 62.66, 67.23, 68.29,

SCHEME 5

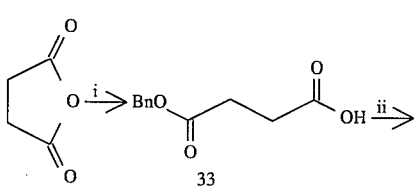

-continued
SCHEME 5

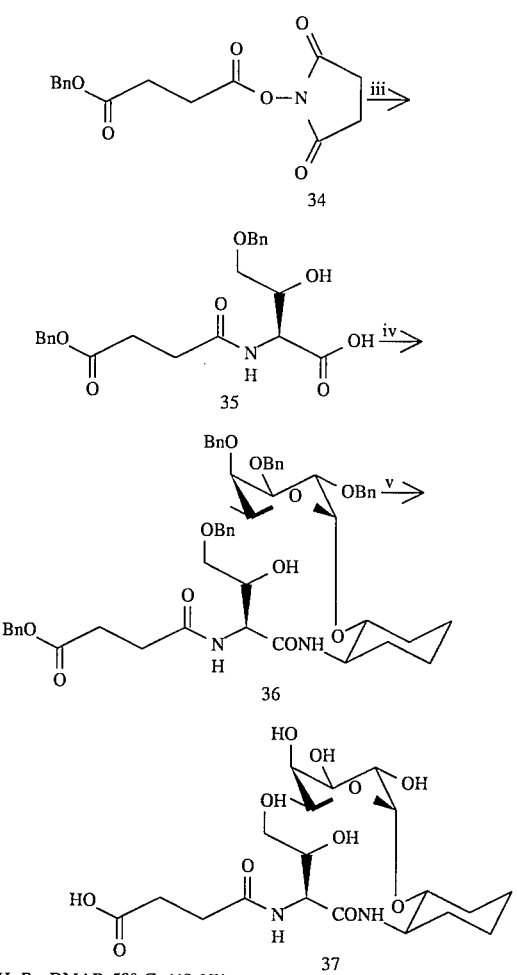

(i) BnOH, Py, DMAP, 50° C. (48.6%);
(ii) N-hydroxylsuccinamide, CH$_2$Cl$_2$(34%);
(iii) 23, DMF/H$_2$O, Et$_3$N(87%);
(iv) EDAC, HOBT, 20(52.2%);
(v) Pd(OH)$_2$/C, H$_2$, EtOAc/H$_2$O, 1:1(65.4%).

69.95, 71.32, 72.22, 75.24, 93.03, 172.2, 175.7, 178.0. HRMS calcd for C$_{20}$H$_{34}$N$_2$O$_{11}$Cs (M+Cs$^+$) 611.1217, found 611.1241.

R isomer (Minor): $^1$H NMR (500 MHz, D$_2$O) δ 1.11 (d, 3H, J=6.5 Hz, H-6), 1.17 (m, 4H), 1.70 (m, 3H), 2.15 (m, 1H), 2.60 (m, 2H), 3.30–3.90 (m, 6H, H-2, H-3, H-4 and H-5), 4.36 (d, 1H, J=7.5 Hz), 4.99 (d, 1H, J=4.0 Hz, H-1) $^{13}$C NMR (125 MHz, D$_2$O) δ 15.77, 23.72, 24.63, 29.05, 30.27, 30.92, 31.68, 53.23, 55.31, 62.88, 67.13, 68.38, 70.02, 72.22, 72.27, 75.87, 93.61, 171.1, 171.1, 174.5. HRMS calcd for C$_{20}$H$_{34}$N$_2$O$_{11}$Cs (M+Cs$^+$) 611.1217, found 611.1231.

Compound 40

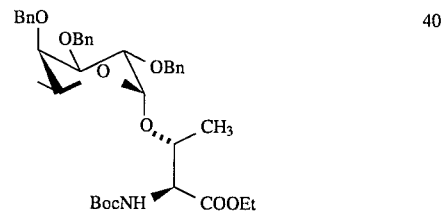

L-Fucose was first converted to tribenzylfucosyl phosphite 38, from methodology established by Muller et. Al.

*Liebigs Ann. Chem.* 1994, 325 and Wong et. Al. *J. Org. Chem.* 1994, 59, 864. The resulting compound (1.0 equivalents) was successfully coupled to Boc-L-Thr-OEt 39 (1.1 equivalents; Wong et. al. *J. Org. Chem.* 1994, 59, 864) using trifluromethanesulfonic acid or TMSOTf (0.1 equivalents) as catalyst in methylene chloride at 0° C. to give the Boc-L-Thr (tri-o-benzyl-α-Fuc)-OEt (40) in 80% yield after standard workup and purification (1× water, 1× NaHCO$_3$, brine, dry over sodium sulfate and then flash chromatography). $^1$H NMR (400 MHz, CDCl$_3$) δ 7.25–7.40 (m, 15 H), 5.34 (d, J=9.6 Hz, 1 H, N H), 4.92 (d, J=11.6 Hz, 1 H), 4.84 (d, J=3.8 Hz, 1 H), 4.79 (d, J=11.4 Hz, 1 H), 4.76 (d, J=11.5 Hz, 1 H), 4.67 (d, J=11.7 Hz, 1 H), 4.62 (d, J=11.9 Hz, 1 H), 4.60 (d, J=11.6 Hz, 1 H), 4.32–3.99 (m, 5H), 3.80 (dd, J=2.8 and 10.1 Hz, 1 H), 3.69 (dq, J=7.0 Hz, 1 H), 3.60 (d, J=2.4 Hz, 1 H), 1.48 (s, 9H), 1.20–1.26 (m, 6 H), 1.06 (d, J=6.4 Hz, 3 H); HRMS for $C_{38}H_{49}NO_9+CS^+$ (M+Cs$^+$), calcd 796.2462, found 796.2485.

Compound 44

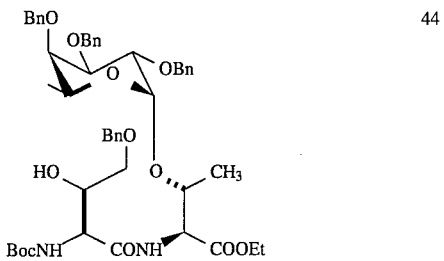

First Boc deprotection of 40 in 30% TFA (trifluoracetic acid) in 0.1 Molar CH$_2$Cl$_2$ at 25° C., 30 min; quench water, wash NaHCO$_3$, dry sodium sulfate; purification by flash chromatography gave the free amine: L-Thr (tri-O-benzyl-a-Fuc)-OEt. Next, the free amino moiety (1.0 equivalents) of L-Thr (tri-O-benzyl-a-Fuc)-OEt was coupled with 1.1 equivalents of (1S, 2R)-N-Boc-1-amino-3-benzyl-oxy-2-hydroxy-butyric-acid 43 (as synthesized below) using 1.5 equiv of EDCl, 1.5 equiv of HOBt, 0.1 Molar CH$_2$Cl$_2$, 0° C., 30 h and 60% yield, to provide 44 after standard workup and flash column chromatography purification conditions.

The (1S, 2R)-N-Boc-1-amino-3-benzyloxy-2-hydroxy butyric acid 43 was prepared from glycine 42 and O-benzylgycolaldehyde 41 by a L-threonine aldolase-catalyzed reaction as adopted from Wong et. al. *Tetrahedron Lett.* 1995, 36, 4081. Subsequent protection with 1.1 equivalents of BocN$_3$ (Aldrich company) in 0.10 Molar methylene chloride gave compound 43 after standard workup and flash chromatography; 73% overall yield 2 steps: $^1$H NMR (400 MHz, CDCl$_3$) δ 7.21–7.50 (m, 20 H), 5.38 (d, J=9.4 Hz, 1 H), 4.95–4.57 (m, 9 H), 4.35–3.99 (m, 7H), 3.80–3.60 (m, 5 H), 1.48 (s, 9H), 1.20–1.26 (m, 6 H), 1.06 (d, J=6.4 Hz, 3 H); HRMS for $C_{49}H_{62}N_2O_{12}+Cs^+$ (M+Cs$^+$), calcd 1003.3357, found 1003.3315.

Compound 45.

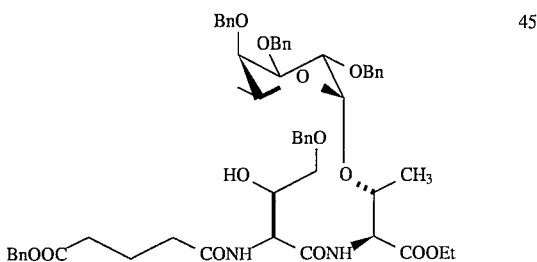

Boc deprotection of 44 in 30% TFA (trifluoracetic acid), 0.1 Molar CH$_2$Cl$_2$ at 25° C., 30 min was followed by quench with water, wash with NaHCO$_3$ and drying over sodium sulfate. Purification by flash chromatography was followed by coupling with 1.1 equivalents monobenzyl glutarate (Sigma company), 1.5 equiv of EDCl, 1.5 equiv of HOBt, CH$_2$Cl$_2$, 25° C., 20 h, to provide compound 45 70% after purification by flash chromatography. Compound 45: $^1$H NMR (400 MHz, CDCl$_3$) δ 8.00 (d, J=9.1 Hz, 1 H), 7.21–7.50 (m, 25 H), 6.75 (d, J=7.6 Hz, 1 H), 5.12–4.57 (m, 11 H), 4.35–3.99 (m, 7H), 3.80–3.60 (m, 5 H), 2.45 (t, J=7.5 Hz, 2H), 2.43 (t, J=7.0 Hz, 2H), 1.98 (t, J=7.5 Hz, 2H) 1.20–1.26 (m, 6 H), 1.06 (d, J=6.4 Hz, 3 H); HRMS for $C_{56}H_{66}N_2O_{13}+Cs^+$ (M+Cs$^+$), calcd 1107.3614, found 1107.3667.

SCHEME 6

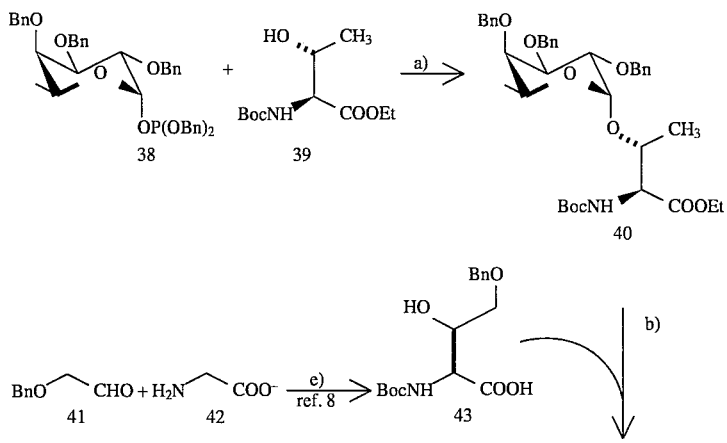

-continued
SCHEME 6

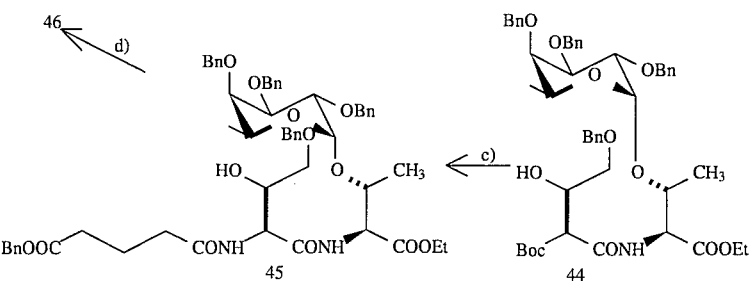

Scheme 6. Reagents and conditions:
a) TfOH, CH₂Cl₂, −15° C., 1h, 84%;
b) (i) 30% TFA in CH₂Cl₂, 25° C., 30 min. (ii) HOBt, EDCI, CH₂Cl₂, 0° C., 30 h, 60% yield for two steps;
c) (i) 30% TFA in CH₂Cl₂, 25° C., 30 min. (ii) mono-benzyl glutarate, HOBt, EDCI, CH₂Cl₂, 25° C., 20 h, 70%;
d) H₂ (1 atm), 20% Pd(OH)₂ on C, MeOH, 24h, 50%;
e) (i) threonine aldolase, 86%. (ii) BocN₃, 90%.

Compound 46

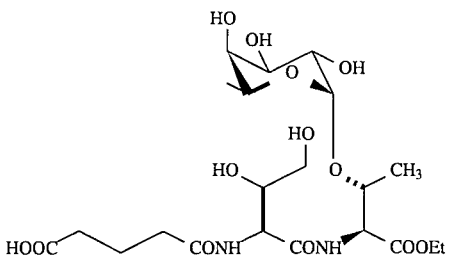

The benzyl groups of 45 were cleaved by hydrogenation over 20% Pd(OH)₂/C in methanol and the crude product was purified on Biogel P-2 chromatography to obtain 46 (54%). Compound 46 and other key intermediates were characterized by ¹H NMR and high resolution mass analysis. Compound 46 (amorphous): ¹H NMR (400 MHz, D₂O) δ 4.98 (d, J=3.2 Hz, 1 H, H-1), 4.61 (d, J=2.2 Hz, 1 H), 4.56 (d, J=7.2 Hz, 1 H), 4.46–4.44 (dd, J=2.2 and 6.4 Hz, 1 H), 4.28–4.13 (m, 3 H), 4.02–3.98 (m, 1 H), 3.86–3.59 (m, 5 H), 2.42–2.22 (m, 4 H), 1.90–1.79 (m, 2 H), 1.30–1.18 (m, 9 H); electrospray negative ion mass (declustering potential=−80 V) m/z 523 [(M−H)⁻; calcd for C₂₁H₃₆N₂O₁₃: 524].

Compound 47.

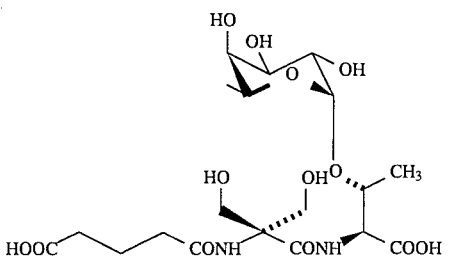

Compound 47 was synthesized from the key intermediate 40 by the same methods as that of compound 46. First Boc deprotection of 40 in 30% TFA (trifluoracetic acid) in 0.1 Molar CH₂Cl₂ at 25° C., 30 min; quench water, wash NaHCO₃, dry sodium sulfate; purification by flash chromatography gave the free amine. Next, the free amino moiety (1.0 equivalents) was coupled with 1.1 equivalents of N-BOC-α-hydroxymethyl serine (prepared according to the procedure described previously: Otani et. al Arch. Biochem. Biophys. 1960, 90, 254) using 1.5 equiv of EDCl, 1.5 equiv of HOBt, 0.1 Molar CH₂Cl₂, 0° C., 30 h and 60% yield, to provide the intermediate after standard workup and flash column chromatography purification conditions.

Boc deprotection of this intermediate, in 30% TFA (trifluoracetic acid), 0.1 Molar CH₂Cl₂ at 25° C., 30 min was followed by quench with water, wash with NaHCO₃ and drying over sodium sulfate. Purification by flash chromatography was followed by coupling with 1.1 equivalents monobenzyl glutarate (Sigma company), 1.5 equiv of EDCl, 1.5 equiv of HOBt, CH₂Cl₂, 25° C., 20 h, to provide anonther intermediate compound 60% after purification by flash chromatography.

The benzyl groups of this intermediate compound were cleaved by hydrogenation over 20% Pd(OH)₂/C in methanol and the crude product was purified on Biogel P-2 chromatography to obtain 47. Compound 47 and other key intermediates were characterized by ¹H NMR and high resolution mass analysis. Compound 47 (amorphous): ¹H NMR (400 MHz, D₂O) δ 4.96 (d, J=3.2 Hz, 1 H, H-1), 4.68–4.37 (m, 3 H), 4.07–3.63 (m, 7 H), 2.43–2.37 (m, 4 H), 1.83 (t, 2 H), 1.23–1.13 (m, 6 H); electrospray negative ion mass (declustering potential=−80 V) m/z 495 [(M−H)⁻; calcd for C₁₉H₃₂N₂O₁₃: 496].

Compound 48

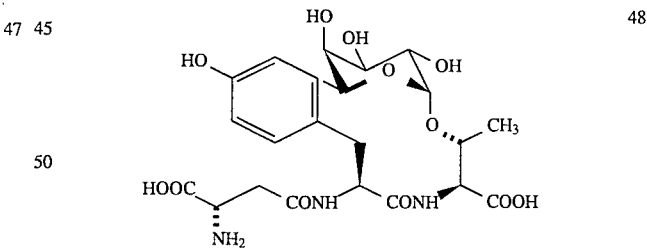

Compound 48 was synthesized from the key intermediate 40 by the same methods as that of compound 46. First Boc deprotection of 40 in 30% TFA (trifluoracetic acid) in 0.1 Molar CH₂Cl₂ at 25° C., 30 min; quench water, wash NaHCO₃, dry sodium sulfate; purification by flash chromatography gave the free amine. Next, the free amino moiety (1.0 equivalents) was coupled with 1.1 equivalents of compound 49 (synthesized infra), using 1.5 equiv of EDCl, 1.5 equiv of HOBt, 0.1 Molar CH₂Cl₂, 0° C., 30 h and 60% yield, to provide an intermediate compound after standard workup and flash column chromatography purification conditions.

Compound 49

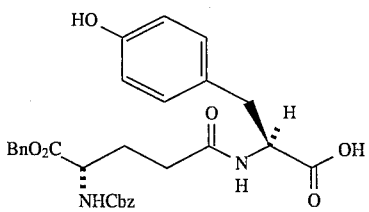

Compound 49 was prepared from the coupling of N-Cbz-O-Bn-Glu (Sigma company) with tyrosine, using standard coupling conditions (I.e. 1.5 equiv of EDCl, 1.5 equiv of HOBt, 0.1 Molar $CH_2Cl_2$, 0° C., 30 h). After standard workup, the compound was subsequently purified by flash chromatography Boc deprotection of the intermediate compound from 48, in 30% TFA (trifluoracetic acid), 0.1 Molar $CH_2Cl_2$ at 25° C., 30 min was followed by quench with water, wash with $NaHCO_3$ and drying over sodium sulfate. Purification by flash chromatography, provided another intermediate compound, after purification by flash chromatography.

The benzyl groups of this second intermediate compound, were cleaved by hydrogenation over 20% $Pd(OH)_2/C$ in methanol and the crude product was purified on Biogel P-2 chromatography to obtain 48. Compound 48 and other key intermediates were characterized by $^1H$ NMR and high resolution mass analysis. Compound 48 (amorphous): $^1H$ NMR (500 MHz, $D_2O$) δ 7.02 (d, J=8.4 Hz, 1 H), 6.69 (d, J=8.3 Hz, 1 H), 4.81 (d, J=4.0 Hz, 1 H), 4.57 (dd, J=4.8, 9.0 Hz, 1 H), 4.29–4.07 (m, 3 H), 3.85 (q, J=6.5 Hz, 1 H), 3.74–3.55 (m, 3 H), 3.05 –2.99 (m, 1 H), 2.81–2.72 (m, 2 H), 2.58–2.50 (m, 1 H), 1.01 (d, J=6.5 Hz, 3 H), 0.97 (d, J=6.0 Hz, 3 H); electrospray negative ion mass (declustering potential=–80 V) m/z 542 [(M–H)$^-$; calcd for $C_{23}H_{33}N_3O_{12}$: 543].

Compound 50

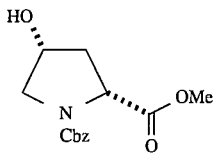

To a solution of cis-4-hydroxy-D-proline (Aldrich company, 502 mg 3.8 mmole) in MeOH (7 mL), at 0° C. was added thionyl choride (0.3 mL, 4.25 mmole) dropwise. The reaction was stirred at 25° C. for 1 hour before it was heated at reflux for 22 hour. The resulting solution was concentrated, and the residue was azeotroped with MeOH. The white product formed was kept under reduced pressure at 0.5 mmHg for 2 hour (699 mg, 99% yield). A mixture of methyl cis-4-hydroxy-D-prolinate HCl salt (699 mg, 3.83 mmole) was cooled to 0° C. With efficient stirring, CbzCl (Benzyl chloroformate, Aldrich company, 0.6 mL, 4.2 mmole) was added, followed by DIEA (diisopropylethylamine, Aldrich Company, 1.6 mL, 9.2 mmole) dropwise and $H_2O$ (3 mL). The reaction was stirred at room temperature for 12 hour and then evaporated the organic solvent. This aqueous residue was extracted with ethylacetate (50 mL), the organic layer was washed with 5% aqueous HCl (10 mL), 5% aqueous $NaHCO_3$ (10 mL) and saturated aqueous NaCl (10 mL), dried ($MgSO_4$), filtered and concetrated. The crude product was purified by flash column chromatograph eluting with Ethylacetate:Hexane (3:2) to provide compound 50 as a viscous oil (897 mg, 84%). $^1H$ NMR (500 MHz, $CDCl_3$) δ 7.37–7.27 (m, 10H), 5.20 (d, J=12.7 Hz, 2H), 5.11 (d, J=12.4 Hz, 1H), 5.06 (d, J=12.4 Hz, 1H), 4.45 (dd, J=9.8, 1.2 Hz, 1H), 4.42–4.38 (m, 3H), 3.81 (s, 3H), 3.77–3.70 (m, 2H), 3.65–3.58 (m, 2H), 3.62 (s, 3H), 3.39 (d, J=9.6 Hz, 1H), 3.23 (d, J=9.3 Hz, 1H), 2.38–2.29 (m, 2H), 2.16–2.12 (m, 2H); $^{13}C$ NMR (125 MHz, $CDCl_3$) δ 175.2, 174.9, 155.0, 154.2, 136.3, 128.5, 128.4, 128.1, 128.0, 127.8, 71.2, 70.2, 67.3, 58.1, 57.7, 56.0, 55.7, 52.9, 52.6, 38.6, 37.7; MS m/e calc'd for $C_{14}H_{17}NO_5Cs$ (M+Cs$^+$): 412.0161, found 412.0175.

Compound 51.

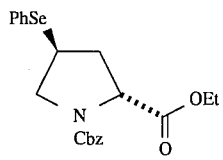

To a solution of protected hydroxyl proline 50 in $CH_2Cl_2$ (30 mL) at 0° C. was added triethylamine (0.46 ml, 3.39 mmole) dropwise, followed by mesyl cholride. A catalytic amount of DMAP (dimethylaminopyridine) was added, and the reaction mixture was stirred at 0° C. to 25° C. for 1.5 hr. The mixture was poured into 30 mL of ice/$H_2O$ with stirring. The product was extracted with ethylacetate (2×30 mL). The combined orgranic layer were washed with 0.1M HCl, 5% aqueous $NaHCO_3$, and saturated aqueous NaCl, dried over $MgSO_4$, filtered, and concentrated. The crude product was purified by flash column chromatograph eluting with ethylacetate:Hexane (2:1) to give mesylate proline 3 (935 mg, 87.5%) as a clear oil. Sodium borohydride (26.6 mg, 0.7 mmole) was added in small portions to a solution of diphenyl selenide (109.6 mg, 0.35 mmole) at 0° C. The mixture was stirred for 5 min until the bright yellow color disappered. The mixture solution was added to the previously prepared mesylate (209 mg, 0.59 mmole), followed by refluxing for 2 hr, and then the solvent was removed in vacuum. The residue was diluted with ethylacetate (50 mL), and the organic layer were washed with $H_2O$. The resulting organic phase was dried ($MgSO_4$), filtered, and concentrated. The crude product was purified by flash column chromatograph eluting with ethylacetate:hexane (1:4) to afford phenylselenyl proline 51 (179 mg, 70%). Compound 51.: $^1H$ NMR (500 MHz, $CDCl_3$) δ 7.57–7.52 (m, 4H), 7.38–7.26 (m, 16H), 5.18 (d, J=8.0 Hz, 1H), 5.15 (d, J=8.0 Hz, 1H), 5.09 (d, J=12.5 Hz, 1H), 5.04 (d, J=12.5 Hz, 1H), 4.45 (dd, J=8.5, 4.0 Hz, 1H), 4.39 (dd, J=8.5, 4.5 Hz, 1H), 4.22–4.16 (m, 2H), 4.06–3.95 (m, 4H), 3.82–3.76 (m, 2H), 3.59 (dd, J=11.5, 7.0 Hz, 1H), 3.51 (dd, J=11.0, 7.0 Hz, 1H), 2.38–2.25 (m,1.26, t, 7.0, 3), 1.11 (t, J=7.5 Hz, 3H),; $^{13}C$ NMR (125 MHz, $CDCl_3$) δ 172.3, 172.1, 154.5, 153.9, 135.3, 135.1, 129.3, 128.5, 128.4, 128.3, 128.0, 128.0, 127.9, 127.8, 67.2, 61.4, 61.3, 59.0, 58.7, 53.3, 52.8, 37.7, 36.9, 36.8, 36.3, 14.1, 14.0; MS m/e calc'd for $C_{21}H_{25}NO_4Se$ (M+H$^+$): 434.0871, found 434.0858.

Compound 52.

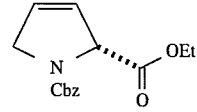

A mixture of phenylselenyl proline (146.4 mg, 0.38 mmole) and $CH_2Cl_2$ (5 mL) was initially cooled to 0° C. in an ice bath. Pyridine (1.1 equivalents) was added dropwise to this solution. A solution of 30% $H_2O_2$ was then gradually added over a 5 min period. The mixture was stirred at 25° C. for 1 hour and then diluted with ethylacetate (25 mL). The orgranic layer was washed with 0.1M HCl (5 mL), saturated aqueous NaHCO$_3$ (5 mL), and saturated aqueous NaCl. The organic phase was dried over MgSO$_4$, filtered, and concentrated. The resulting residue was purified by flash column chromatography eluting with ethylacetate:hexane (1:4) to afford the product 52 (76 mg, 73%) as a clear oil. $^1$H NMR (500 MHz, CDCl$_3$) δ 7.39–7.26 (m, 10H), 6.01–5.94 (m, 1H), 5.80–5.73 (m, 1H), 5.23–5.03 (m, 6H), 4.38–4.25 (m, 4H), 4.21 (dq, J=0.7, 7.1 Hz, 2H), 4.10–4.02 (m, 2H), 1.27 (dt, J=0.8, 7.1 Hz, 3H), 1.14 (dt, J=0.7, 7.1 Hz, 3H); $^{13}$C NMR (125 MHz, CDCl$_3$) δ 170.2, 169.9, 154.3, 153.9, 136.5, 136.4, 129.1, 129.1, 129.0, 129.0, 128.5, 128.4, 128.4, 128.4, 128.0, 128.0, 127.9, 127.9, 127.8, 127.7, 67.1, 66.7, 66.4, 61.4, 61.3, 53.8, 53.4, 14.1, 14.0; MS m/e calc'd for C$_{15}$H$_{18}$NO$_4$ (M+H$^+$): 276.1236, found 276.1241.

Compound 53

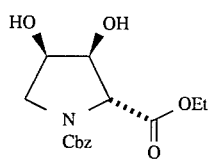

A mixture of compound 52 (405 mg, 1.48 mmole) and H$_2$O: Acetone:t-Butanol (6.25:2.5:1, 4.68 mL) was added N-methyl-morpholine-N-oxide (518 mg, 4.43 mmole) and catalytic amount of K$_2$OSO$_4$. The reaction mixture was stirred at 0° C. for overnight. The reaction mixture was added Na$_2$SO$_3$ (559 mg, 4.4 mmole) and stirred at 25° C. for 1 hr. The organic solvent was evaporated and the aqueous layer was extracted with ethylacetate (3×25 mL). The organic phase was dried over MgSO$_4$, filtered, and concentrated. The resulting residue was purified by flash column chromatography eluting with EtOAc:Hexane:MeOH (10:10:1) to afford the product 53 (375 mg, 82%) as a clear oil. $^1$H NMR (500 MHz, CDCl$_3$) δ 7.34–7.27 (m, 10H), 5.14 (d, J=12.4 Hz, 2H), 5.09 (d, J=12.4 Hz, 1H), 5.01 (d, J=12.4 Hz, 1H), 4.34–4.20 (m, 8H), 4.07–4.00 (m, 2H), 3.78–3.73 (m, 2H), 3.60 (dd, J=11.7, 4.1 Hz, 1H), 3.51 (dd, J=11.4, 4.6 Hz, 1H), 1.27 (t, J=7.1 Hz, 3H), 1.01 (t, J=7.1 Hz, 3H); $^{13}$C NMR (125 MHz, CDCl$_3$) δ 128.5, 128.4, 128.1, 127.9, 127.9, 75.8, 74.7, 70.5, 69.8, 67.4, 64.9, 64.6, 61.7, 61.6, 51.2, 50.8, 31.0, 14.1, 14.0; MS m/e calc'd for C$_{15}$H$_{19}$NO$_6$Na: 332.1110, found 332.1124.

Compound 54

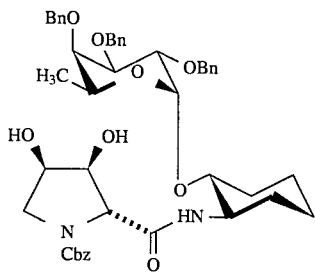

To a mixture of dihydroxyl proline 53 (94.8 mg, 0.3 mmole) and THF (3 mL) at 0° C. was added a cooled 0.2M aqueous solution of LiOH (3 mL) dropwise over a 10 min period. After being stirred at 25° C. for 5 hr, the solution was concetrated to one-half volume. The aqueous solution was added Dowex 50 (0.2 g) and stirred till solution pH=2 (40 min). After filtrated, the aqueous solution was extracted with ethylacetate (4×15 mL), dried over MgSO$_4$, and concentrated to produce the desired acid as a clear oil, which need no further purification. A mixture of prolinate-fucosyl amine (compound 16 synthesized infra), and CH$_2$Cl$_2$ was cooled to 0° C. The coupling reagent HOBT (1-hydroxybenzotriazole hydrate, Aldrich company, 53 mg, 0.39 mmole) was added followed by EDCl (1-(3-dimethylaminopropyl)-3-ethylcarbodiimide-hydrochloride, Aldrich company, 75 mg, 0.39 mmole), and the solution was stirred at 0° C. for 10 min. After being stirred at 25° C. for 10 hours, the solvent was evaporated and the residue was diluted with ethylacetate. The resulting organic layer was washed with H$_2$O (2×10 mL), 0.1M HCl (2×5 mL), saturated aqueous NaHCO$_3$ (2×5 mL), and saturated aqueous NaCl. The organic phase was dried over MgSO$_4$, filtered, and concentrated. The resulting residue was purified by flash column chromatography eluting with ethylacetate:Hexane:MeOH (10:10:1) to afford the product 54 (186 mg, 78%) as a clear oil; MS m/e calc'd for C$_{15}$H$_{19}$NO$_6$CS (M+Cs$^+$): 927.2833, found 927.2864.

Compound 55

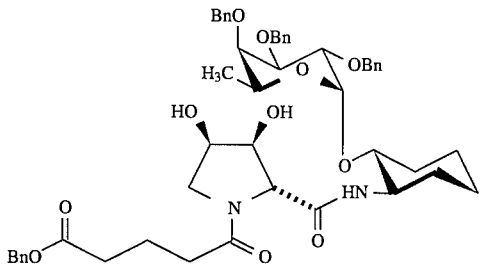

Compound 54 (70 mg, 0.088 mmole) was dissolved in MeOH (3 mL) and stirred in the presence of 20% Pd(OH)$_2$ on carbon (Pearlman's type, 1 mg) under an atmosphere of hydrogen (1 atm) for 1 hour. After filtration, the filtrate was evaporated in vacuo to obtain an amine intermediate, which did not need any further purification. A mixture of the resulting amine, monobenzyl glutarate (1.1 equivalent, Aldrich company), and CH$_2$Cl$_2$ was cooled to 0° C. The coupling reagent HOBT (14.8 mg, 0.11 mmole) was added followed by EDCl (21 mg, 0.11 mmole), and the solution was stirred at 0° C. for 10 min. After being stirred at 25° C. for 10 hour, the solvent was evaporated and the residue was diluted with ethylacetate. The resulting organic layer was washed with H$_2$O (2×10 mL), 0.1M HCl (2×5 mL), saturated aqueous NaHCO$_3$ (2×5 mL), and saturated aqueous NaCl. The organic phase was dried over MgSO$_4$, filtered, and concentrated. The resulting residue was purified by flash column chromatography eluting with CHCl$_3$:Methanol (20:1) to afford compound 55 (54.7 mg, 72%) as a clear oil. $^1$H NMR (500 MHz, CDCl$_3$) δ 7.38–7.24 (m, 20H), 6.92 (d, J=8.4 Hz, 1H), 5.08 (s, 2H), 4.95 (d, J=3.5 Hz, 1H), 4.92 (d, J=11.5 Hz, 1H), 4.78 (d, J=11.8 Hz, 1H), 4.74 (d, J=11.8 Hz, 1H), 4.70 (d, J=11.8 Hz, 1H), 4.64 (d, J=11.8 Hz, 1H), 4.59 (d, J=11.5 Hz, 1H), 4.32 (t, J=4.1 Hz, 1H), 4.27 (q, J=6.5 Hz, 1H), 4.14 (d, J=4.1 Hz, 1H), 4.01–4.00 (m, 2H), 3.89 (dd, J=9.8, 2.7 Hz, 1H), 3.81–3.77 (m, 1H), 3.63 (br., 1H), 3.52 (dd, J=10.8, 2.8 Hz, 1H), 3.39 (dd, J=10.8, 4.7 Hz, 1H), 3.35 (dd, J=9.8, 3.5 Hz, 1H), 2.4 (t, J=7.1 Hz, 2H), 2.33–2.23 (m, 2H), 1.91 (t, J=7.2 Hz, 2H), 2.00–1.93 (m, 1H), 1.80–1.52 (m, 3H), 1.33–1.17 (m, 4H), 1.14 (t, J=6.5 Hz, 3H); $^{13}$C NMR (125 MHz, CDCl$_3$) δ 173.0, 172.7, 169.5, 139.1, 138.6, 138.5, 135.8, 128.6, 128.3, 128.3, 128.2, 127.9, 127.6, 127.6, 127.4, 94.3, 78.9, 77.7, 76.4, 74.7, 73.7, 73.1, 72.9, 70.8, 67.1, 66.3, 65.2, 52.5, 51.5, 33.1, 32.9, 31.1, 29.7, 29.4, 23.9, 23.5, 19.9, 16.6; MS m/e calc'd for C$_{50}$H$_{60}$N$_2$O$_{11}$Cs (M+Cs$^+$): 997.3251, found 997.3275.

Compound 56

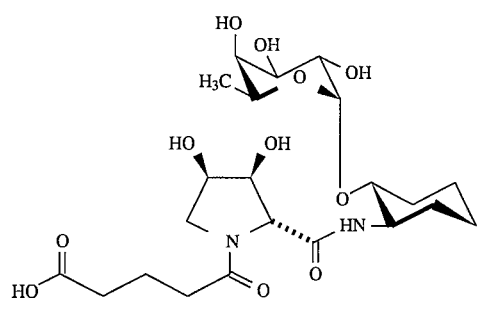

SCHEME 7

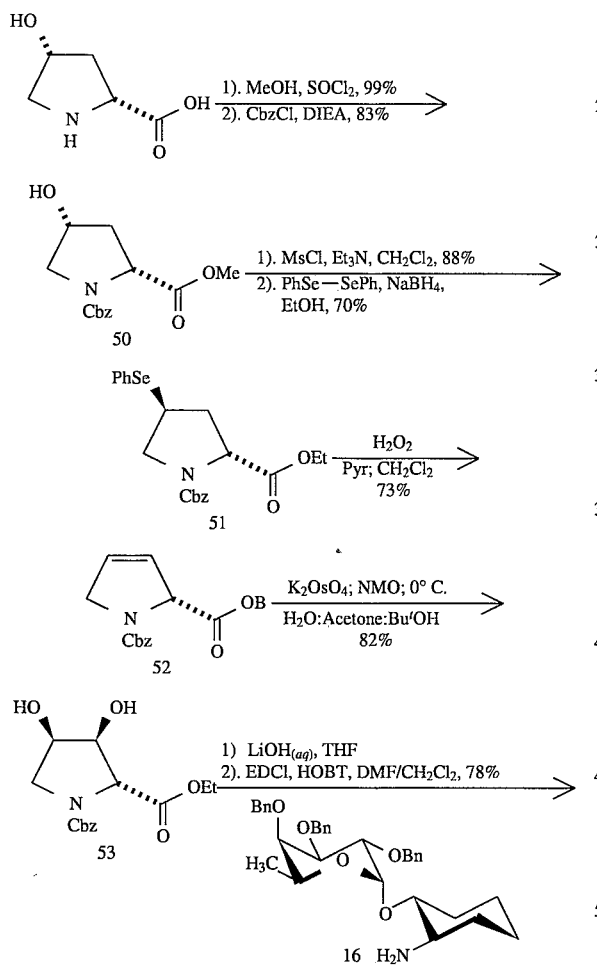

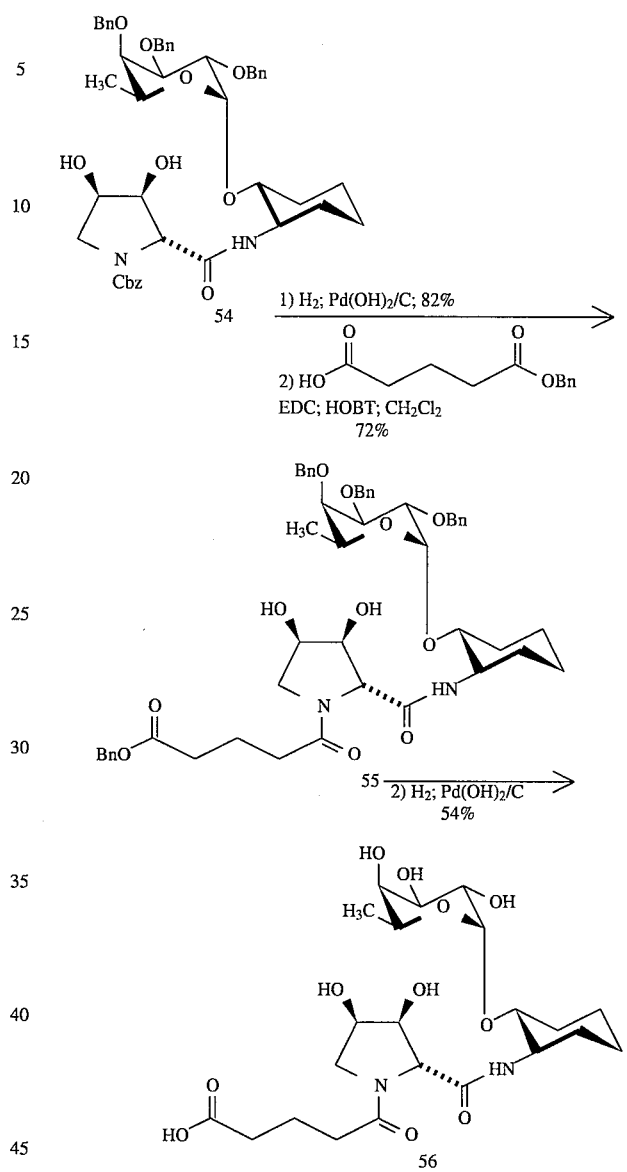

Compound 55 (34 mg, 0.04 mmole) was dissolved in methanol:H$_2$O (9:1, 2 mL), and then a catalytic amount of Pd(OH)$_2$ (Degussa type) on carbon was added. Hydrogen was supplied to the reaction system through a balloon. The reaction was complete in 8 h. The mixture was filtered througt celite and concentrated in vacuo. The crude product was purified by biogel P2 (water). The collect fractions were combined and freeze dried to afford the title compound 56 (10.7 mg, 54%). $^1$H NMR (500 MHz, D$_2$O) δ 4.95 (d, J=3.8 Hz, 1H), 4.16 (dd, J=6.2, 3.8 Hz, 1H), 4.02 (dd, J=7.1, 3.8 Hz, 1H), 3.95 (q, J=6.5 Hz, 1H), 3.88 (d, J=7.1 Hz, 1H), 3.67 (dd, J=11.8, 4.1 Hz, 1H), 3.64–3.53 (m, 3H), 3.60 (br., 1H), 3.51 (dd, J=11.8, 2.2 Hz, 1H), 3.36–3.31 (m, 1H), 2.29–2.05 (m, 4H), 2.09 (t, J=7.3 Hz, 2H), 1.76–1.55 (m, 6H), 1.25–1.05 (m, 2H), 1.03 (d, J=6.5 Hz, 3H); $^{13}$C NMR (125 MHz, D$_2$O) δ 182.1, 175.5, 172.4, 92.9, 75.1, 74.6, 72.2, 70.7, 69.9, 68.2, 66.9, 64.9, 53.5, 52.9, 36.2, 33.0, 31.6, 30.5, 28.6, 24.4, 23.5, 21.1, 15.6; MS m/e calc'd for C$_{22}$H$_{36}$N$_2$O$_{11}$Cs (M+Cs$^+$): 637.1373, found 637.1353.

Compound 58.

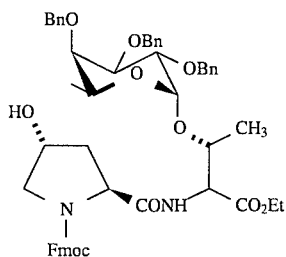

Compound 40 (synthesized supra –1.0 equivalents) was exposed to Boc deprotection in 30% TFA (trifluoroacetic acid) in 0.10 Molar CH$_2$Cl$_2$ at 25° C., 30 min followed by a water quench, wash with NaHCO$_3$ and drying over sodium sulfate. Subsequent purification by flash chromatography gave the free amine. Next, the free amino moiety (1.0 equivalents) was coupled with 1.1 equivalents of FMOC-trans-4-hydroxy-L-proline 57 (synthesized infra) using 1.5 equiv of EDCl, 1.5 equiv of HOBt, 0.1 Molar CH$_2$Cl$_2$, 0° C., 30 hours to provide 58 in a 78% yield, after standard workup and flash column chromatography purification conditions.

The FMOC-trans-4-hydroxy-L-proline 57 was prepared as follows: 1.1 equivalents of FMOC-chloride is added to 1.0 equivalents of trans-4-hydroxy-L-proline (Aldrich company) and allowed to stir for 12 hour at 25° C. in 0.10M methylene chloride. The resulting mixture is quenched with water, washed with sodium bicarbonate and dried over magnesium sulfate (standard workup conditions). The crude compound can then be purified by flash chromatography. Mass Spectral analysis: m/e calc'd for C$_{53}$H$_{58}$O$_{11}$N$_2$Cs (M+Cs$^+$): 1031.3095, found 1031.3143

Compound 59.

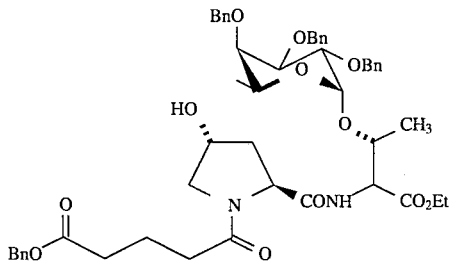

Compound 58 (1.0 equivalents) is resuspended in 0.10 Molar methylene chloride and cooled to 0° C. Next, 1.1 equivalents of diethylamine is added dropwise and allowed to stir for 6 hours, warming to 25° C. The reaction mixture is quenched with 5% HCl solution (0.25 volume of methylene chloride) and washed with sodium bicarbonate, water and brine. The compound is then dried over magnesium sulfate and purified by flash chromatography. Next, the free amino moiety (1.0 equivalents) was coupled with 1.1 equivalents of compound 25 (synthesized supra) using 1.5 equiv of EDCl, 1.5 equiv of HOBt, 0.1 Molar CH$_2$Cl$_2$, 0° C., 30 hours to provide 59 in a 75% overall yield, after standard workup and flash column chromatography purification conditions. $^1$H NMR (500 MHz, CDCl$_3$) δ 8.26 (d, J=9.5 Hz, 1H), 7.40–7.23 (m, 20H), 5.08 (s, 2H), 4.94 (d, J=11.5 Hz, 1H), 4.93 (d, J=3.5 Hz, 1H), 4.79–4.61 (m, 7H), 4.55 (t, J=8.0 Hz, 1H), 4.45 (br., 1H), 4.40–4.36 (m, 1H), 4.21–4.15 (m, 1H), 4.07 (dd, J=10.5, 3.5 Hz, 1H), 4.05–3.97 (m, 1H), 3.78 (dd, J=10.5, 2.5 Hz, 1H), 3.70–3.65 (m, 2H), 3.42 (dd, J=11.0, 3.5 Hz, 1H), 3.17–3.15 (m, 1H), 2.41–2.30 (m, 2H), 2.24–2.19 (m, 1H), 2.10–1.98 (m, 3H), 1.93–1.85 (m, 2H), 1.26 (d, J=6.5 Hz, 3H), 1.24 (q, J=7.0 Hz, 3H), 1.10 (d, J=6.5 Hz, 3H); $^{13}$C NMR (125 MHz, CDCl$_3$) δ 173.2, 72.5, 171.1, 170.6, 138.4, 137.5, 128.5, 128.5, 128.3, 128.3, 128.2, 128.2, 128.2, 128.1, 128.0, 127.7, 127.5, 127.1, 92.9, 79.4, 76.2, 74.8, 73.6, 72.7, 71.0, 70.2, 66.4, 66.1, 61.2, 58.6, 56.4, 55.9, 37.5, 33.5, 33.4, 33.2, 20.0, 16.6, 14.5, 14.2; MS m/e calc'd for C$_{50}$H$_{60}$N$_2$O$_{12}$Cs (M+Cs$^+$): 1013.3201, found 1013.3171.

Preparation of compound 25. Glutaric anhydride (5.7 g, 0.05 mol), benzyl alcohol (5.41 g, 5.18 mL, 0.05 mol) and DMAP (500 mg; 4-dimethylaminopyridine) were dissolved in pyridine (8 mL) and the mixture was stirred at 50° C. for 12 h. After the evaporation of the solvent, saturated NaHCO$_3$ was added and the aqueous solution was washed twice with ethyl acetate. The resulting aqueous solution was acidified to pH 4 by 1N HCl and extracted with ethyl ester. The organic fractions were combined and dried over MgSO$_4$. After filtration and evaporation of the solvent, compound 25 (7.0 g, 63%, Rf=0.7, Ethylacetate/hexane, 2:1) was obtained as a syrup. $^1$H NMR (500 MHz, CDCl$_3$) δ 1.85 (m, 2H), 2.31 (m, 2H), 2.37 (t, 2H, J=7.5 Hz), 5.07 (s, 2H), 7.29 (m, 5H).

Compound 60.

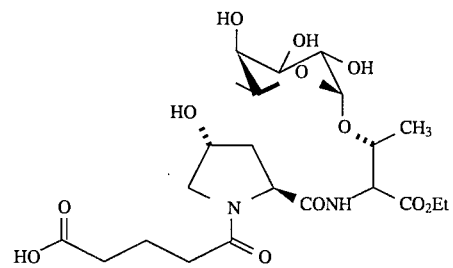

Compound 59 was dissolved in MeOH (0.10 Molar) and stirred in the presence of 0.01 equivalents 10% Pd on carbon under an atmosphere of hydrogen (1 atm) for 12 hours at 25° C. After 12 hours of reaction, the mixture was exposed to filtration; the filtrate was evaporated in vacuo and further purified by flash column chromatography to give compound 60. $^1$H NMR (500 MHz, D$_2$O) δ 4.87 (d, J=3.9 Hz, 1H), 4.52–4.48 (m, 1H), 4.45 (br., 1H), 4.37–4.33 (m, 1H), 4.14–4.08 (m, 1H), 4.03–3.97 (m, 1H), 3.67–3.52 (m, 6H), 2.33–2.22 (m, 3H), 2.11 (t, J=7.0 Hz, 2H), 1.97–1.91 (m, 1H), 1.68 (t, J=7.5 Hz, 2H), 1.15–1.12 (m,

SCHEME 8

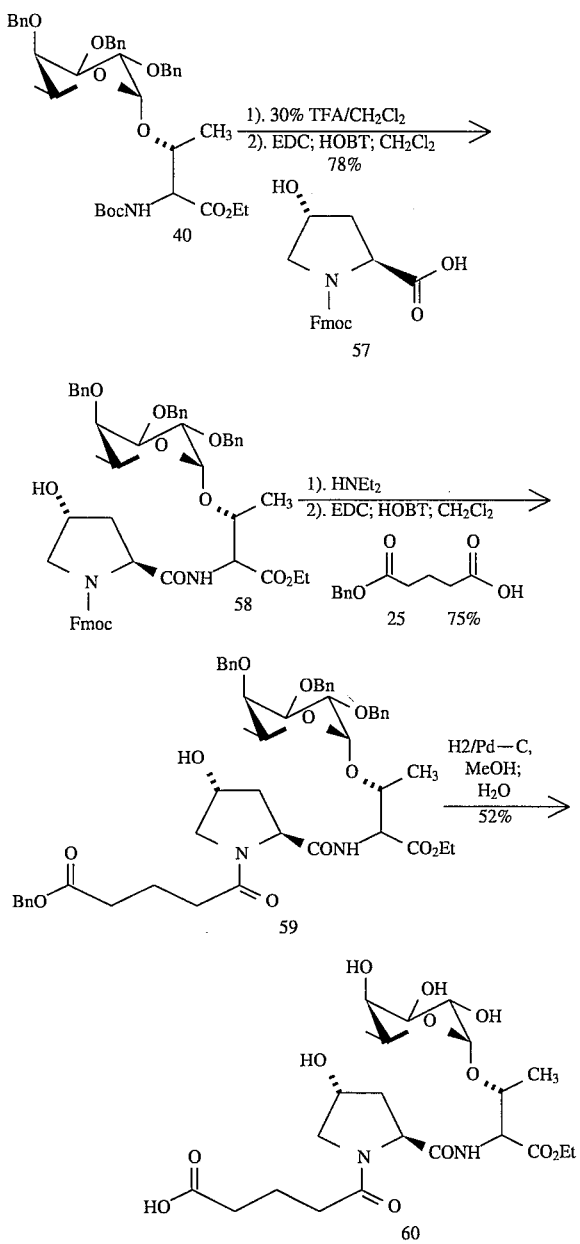

6H), 1.05 (d, J=6.5 Hz, 3H); $^{13}$C NMR (125 MHz, D$_2$O) δ 175.3, 172.3, 94.7, 71.9, 70.9, 70.1, 69.7, 68.0, 63.3, 58.8, 57.8, 55.9, 52.5, 37.6, 36.4, 33.9, 21.4, 15.6, 14.5, 13.6; MS m/e calc'd for negative electrospray C$_{22}$H$_{35}$N$_2$O$_{12}$ (M–H$^+$): 519, found 519.

Compound 61.

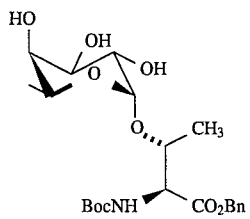

L-Fucose was first converted to fucosyl phosphite from methodology established by Muller et. Al. *Liebigs Ann. Chem.* 1994, 325 and Wong et. Al. *J. Org. Chem.* 1994, 59, 864. The resulting compound (1.0 equivalents) was successfully coupled to Boc-L-Thr-OBn (1.1 equivalents; Wong et. al. *J. Org. Chem.* 1994, 59, 864) using trifluromethanesulfonic acid (TMSOTf; 0.1 equivalents) as catalyst in 0.1 Molar methylene chloride at 0° C. to give the Boc-L-Thr (α-Fuc)-OBn (61) after standard workup and purification (1×water, 1×NaHCO$_3$, brine, dry over sodium sulfate and then flash chromatography).

Compound 62.

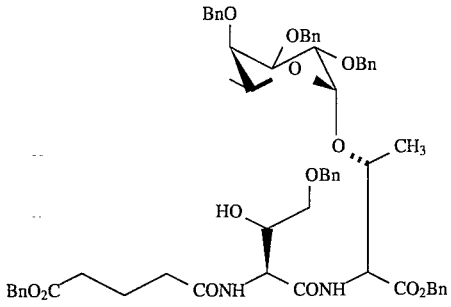

Compound 61 (1.0 equivalents) was exposed to a Boc deprotection in 30% TFA (trifluoracetic acid)/CH$_2$Cl$_2$ solution at 25° C. and 30 min. The reaction mixture was next quenched with water, washed with NaHCO$_3$, and dried over sodium sulfate. Further purification by flash chromatography gave the free amine. Next, the free amino moiety (1.0 equivalents) was coupled with 1.1 equivalents of compound 30, synthesized supra, using 1.5 equiv of EDCl, 1.5 equiv of HOBt, 0.1 Molar CH$_2$Cl$_2$, 0° C., 30 hours to provide 62 in a 71% yield, after standard workup and flash column chromatography purification conditions. Data for compound 62: $^1$H NMR (500 MHz, CDCl$_3$) δ 8.00 (d, J=9.1 Hz, 1H), 7.36–7.24 (m, 30H), 6.75 (d, J=7.6 Hz, 1H), 5.12 (d, J=12.2 Hz, 1H), 5.10 (s, 2H), 5.08–5.07 (m, 1H), 5.02 (d, J=12.2 Hz, 1H), 4.91 (d, J=11.5 Hz, 1H), 4.82 (d, J=3.8 Hz, 1H), 4.75–4.68 (m, 4H), 4.61 (d, J=11.7 Hz, 1H), 4.61–4.57 (m, 1H), 4.55–4.48 (m, 2H), 4.38 (dd, J=6.3, 2.0 Hz, 1H), 4.00–3.98 (m, 2H), 3.66–3.58 (m, 2H), 3.51–3.37 (m, 2H), 3.33 (br., 1H), 2.37 (t, J=7.3 Hz, 2H), 2.25–2.20 (m, 2H), 1.94 (t, J=7.2 Hz, 2H), 1.16 (d, J=6.3 Hz, 3H), 0.90 (d, J=6.5 Hz, 3H); $^{13}$C NMR (125 MHz, CDCl$_3$) δ 172.9, 172.4, 170.8, 170.4, 138.8, 138.5, 138.4, 138.1, 137.8, 135.9, 135.0, 128.7, 128.5, 128.5, 128.4, 128.3, 128.2, 128.2, 127.9, 127.8, 127.7, 127.7, 127.5, 127.5, 94.3, 79.0, 77.3, 76.0, 74.6, 73.5, 73.3, 73.1, 73.0, 72.0, 71.4, 71.2, 71.0, 67.5, 66.9, 66.3, 66.2, 57.3, 55.0, 35.1, 33.3, 20.7, 16.5, 15.6.

Compound 63

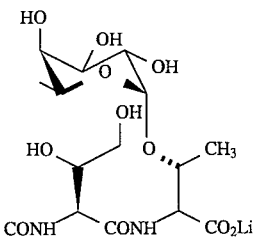

Compound 62 was dissolved in MeOH (0.10 Molar) and stirred in the presence of 0.01 equivalents 10% Pd on carbon under an atmosphere of hydrogen (1 atm) for 12 hours at 25° C. After 12 hours of reaction, the mixture was exposed to filtration; the filtrate was evaporated in vacuo and if necessary, further purified by flash column chromatography to give compound. The compound was next suspended in 0.10 Molar Methanol and room temperature, the mixture was poured into water (30 mL) and washed with ether (3×30 mL). The aqueous layer was then acidified to pH 2 using 1M HCl solution and

SCHEME 9

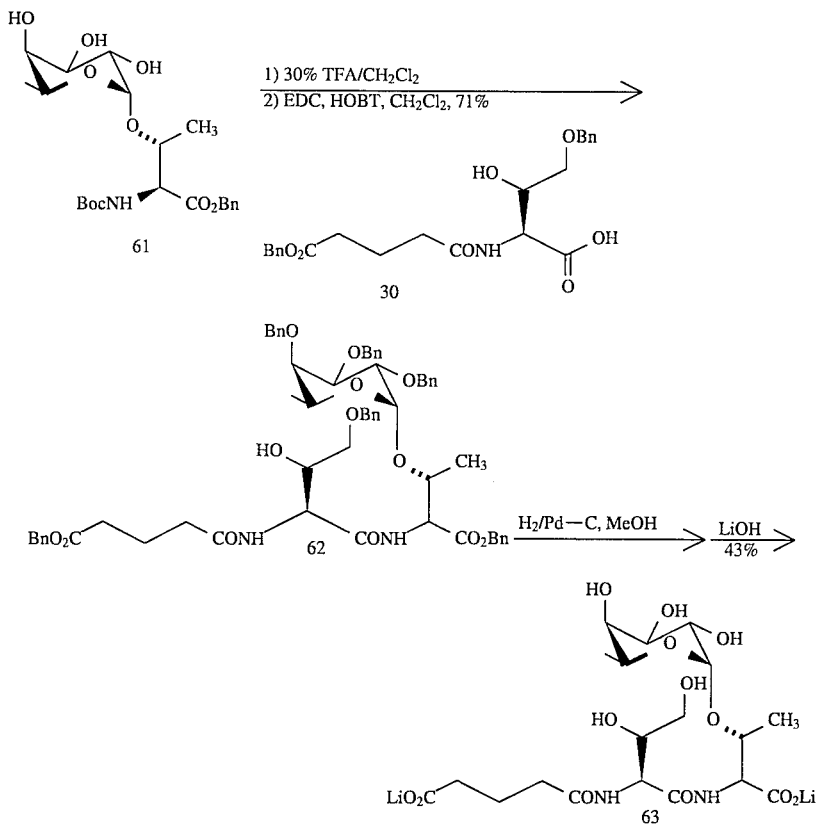

exposed to 1.0 equivalents of LiOH and stirred at 0° C. for 2 hours. The solvent was next removed invacuo, and the compound 63 was further purified by recrystallization or flash chromatography using a polar solvent such as ethylacetate, methanol, methanol: ethyl acetate, etc. $^1$H NMR (400 MHz, D$_2$O) δ 4.98 (d, J=3.2 Hz, 1H), 4.58 (dd, J=1.1 and 8.3 Hz, 1H), 4.40–4.42 (m, 1H), 4.33–4.34 (bs, 1H), 3.94–4.03 (m, 2H), 3.57–3.86 (m, 5H), 2.32 (t, J=7.5 Hz, 2H), 2.20 (t, J=7.4 Hz, 2H), 1.77–1.85 (m, 2H), 1.18 (d, J=6.5 Hz, 3H). MS m/e calc'd for negative electrospray C$_{19}$H$_{31}$N$_2$O$_{13}$ (M–H$^+$): 495, found 495.

Compound 64:

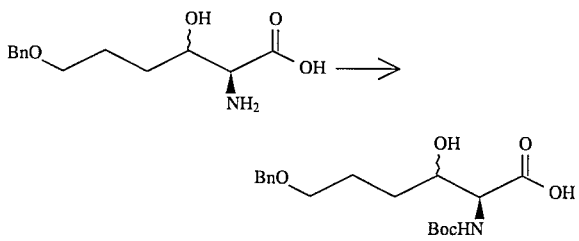

A solution of di tert-butyl dicarbonate (175 mg, 800 μmol) in 1,4-dioxane (2 mL) and triethylamine (100 μL, 700 μmol) were added in one portion to a stirred solution of (2S,3RS)-2-amino-6-benzyloxy-3-hydroxy-hexanoic-acid (derived from Wong et. al. *Tetrahedron Lett*, in press) (172 mg, 677 μmol) in water (2 mL) at room temperature. After 14 hr at extracted with ethyl acetate (5×50 mL). The combined ethyl acetate extracts were washed with sat. sodium chloride solution (3×30 mL), dried (MgSO$_4$) and evaporated down under reduced pressure. This gave (64) (204 mg, 85%) as a viscous yellow gum, which was greater than 90% pure by nmr and used directly without purification: R$_f$ (10% acetic acid in ethyl acetate) 0.55: IR (Film) cm-1 3422, 2964, 2934, 2861, 1714, 1508, 1454, 1393, 1367, 1250, 1163, 1097, 1072, 1027, 739, 698 $^1$H nmr (250 MHz; CD$_3$OD) 7.23–7.13 (5H, m, aromatics), 4,38 (2H, s, 2×C$\underline{H}_2$Ph), 4.07–3.97 (1.5H, m, 2×H2+H3), 3.72–3.68 (0.5H, m, H3), 3.43–3.38 (2H, m, C$_6$H$_2$), 1.67–1.46 (4H, m, 2×H4+2×H5), 1.33 (9H, s, 2x$^t$Bu): $^{13}$C nmr (63 MHz; CD$_3$OD) 174.57, 173.40, 156.38, 156.14, 137.63, 128.40, 127.79, 80.18, 72.89, 71.65, 70.00, 58.12, 57.61, 30.79, 30.46, 28.23, 26.07: High Resolution Mass Spectrum (Doped with CsI): Found M+Cs, 486.0914. C$_{18}$H$_{27}$NO$_6$ requires M+Cs, 486.0893.

Compound 65: Coupling of N-protected amino acids to sugar

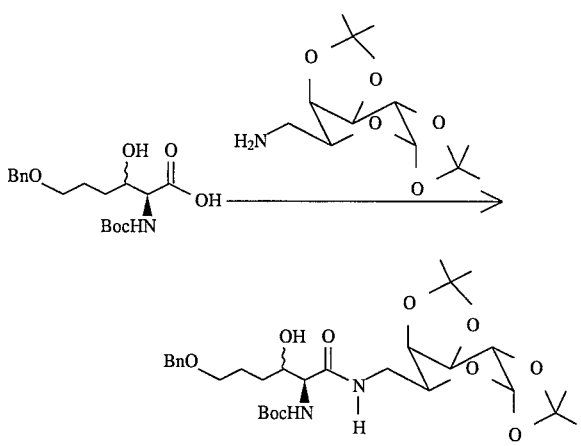

1-(3-Dimethylaminopropyl)-3-ethylcarbodiimide hydrochloride (EDCl, commercially available from Aldrich) (95.4 mg, 500 μmol) was added to a stirred solution of 6-amino-6-deoxy-1,2,3,4-diisopropylidene-α-L-galactopyrano side (derived from the conditions of Surfin et. al., *J. Med. Chem.*, (1980), 23(2), 143–149 and May et. al. *J. Med. Chem.*, (1979), 22(8), 971–976) (130 mg, 500 μmol), N-Boc amino acid (64) (177 mg, 500 μmol), 1-hydroxy benzotriazole (68 mg, 500 μmol) and 4-methyl morpholine (108 μL, 1000 μmol) in dry DMF (5 mL) under argon at −20° C. The resulting mixture was stirred at −20° C. for 1 hr and then allowed to warm slowly to room temperature. After 14 hours, the reaction solution was quenched 5% w/v citric acid solution (20 mL) and extracted with ethyl acetate (6×25 mL). The combined organic extracts were washed with saturated sodium hydrogen carbonate solution (50 mL) and saturated sodium chloride solution (50 mL), dried (MgSO$_4$) and evaporated down under reduced pressure. The residual oil was purified by flash chromatography (silica gel, using gradient elution 40%AE50%AE66% ethyl acetate in hexanes) to give (65) (257 mg, 86%) as a pale yellow foam: R$_f$ (75% ethyl acetate in hexane) 0.66; IR (Film) cm-1 3345, 2980, 2933, 1707, 1662, 1497, 1454, 1369, 1254, 1212, 1167, 1110, 1070, 1007, 918, 902, 859, 736, 698: $^1$H nmr (400 MHz; CDCl$_3$) 7.33–7.25 (5H, m, aromatic), 6.82 (0.5H, br m, C6NH), 6.64 (0.5H, br m, C6NH), 5.49–5.45 (1H, br s, 2×C2'NH), 5.48 (0.5H, d, J 5.0, H1), 5.47 (0.5H, d, J 5.0, H1), 4.58–4.55 (1H, dm, J 7.9, 2×H3), 4.49 (1H, s, CH$_2$Ph), 4.48 (1H, s, CH$_2$Ph), 4.27 (0.5H, dd, J 5.0 and 2.3, H2), 4.26 (0.5H, dd, J 5.0 and 2.3, H2), 4.17 (1H, dd, J 7.9 and 1.5, 2×H4), 4.12 (0.5H, br d, H2'), 4.09–4.06 (0.5H, m, H2'), 3.98–3.92 (1.5H, m, 2×H5+H3'), 3.78–3.76 (1H, m, 2×C$_3$'OH), 3.69–3.56 (1.5H, m, 2×C6H$_a$H$_b$+H3'), 3.51–3.43 (2H, m, 2×C6'H$_2$), 3.26–3.15 (1H, m, 2×C6HH$_b$), 1.85–1.49 (4H, m, 2×C4'H$_2$+2×C5'H$_2$), 1.44 (3H, s, acetonide Me), 1.42 (9H, s, 2×$^t$Bu), 1.41 (3H, s, acetonide Me), 1.31 (3H, s, acetonide Me), 1.27 (3H, s, acetonide Me): $^{13}$C nmr (100 MHz; CDCl$_3$) 171.63, 171.43, 156.02, 155.69, 138.36, 138.08, 128.40, 128.34, 127.71, 127.63, 127.53, 109.53, 109.42, 108.73, 96.39, 96.31, 79.91, 72.99, 72.86, 71.52, 71.46, 71.29, 70.79, 70.45, 70.26, 70.11, 65.63, 65.50, 57.77, 57.27, 39.98, 30.49, 29.62, 28.28, 26.40, 26.03, 25.92, 24.95, 24.85, 24.30: High Resolution Mass Spectrum (Doped with CsI): Found M+Cs, 727.2237. C$_{30}$H$_{46}$N$_2$O$_{10}$ requires M+Cs, 727.2207.

Compound 66. Removal of the t-Boc group

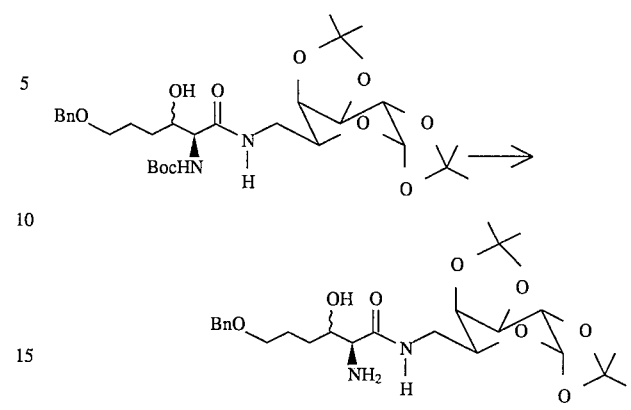

A solution of the glycopeptide (65) (59.5 mg, 100 μmol) in 15% v/v trifluoroacetic acid in dry DCM (4-(dicyanomethylene)-2-methyl-6-(4-dimethylaminostyryl)-4H-pyran; commercially available from Aldrich; 1 mL) was stirred under argon at room temperature. After 2 hr, the solution was evaporated down under reduced pressure and the residual oil dissolved up in n-butanol:water:methanol (5:3:2) (10 mL). To the solution was added Dowex (Cl−, prewashed with methanol, 100 mg) and the mixture stirred for 30 mins, then filtered and the solid washed with methanol (3×5 mL) and the combined filtrate and washings evaporated under reduced pressure. The residual oil was purified by flash chromatography (silica gel, using gradient elution 19:0.9:0.1AE9:0.9:0.1 DCM:MeOH:NH$_3$ $_{(aq)}$) to give (66) (42.5 mg, 86%) as a light brown oil: R$_f$ (9:0.9:0.1 DCM:MeOH:NH$_3$ $_{(aq)}$) 0.42; IR (Film) cm-1 3368, 2987, 2932, 2857, 1657, 1526, 1454, 1383, 1255, 1211, 1167, 1109, 1070, 1007, 919, 902, 736, 698: $^1$H nmr (400 MHz; CDCl$_3$) 7.59 (0.5H, br m, C6NH), 7.44 (0.5H, br m, C6NH), 7.35–7.26 (5H, m, aromatic), 5.49 (1H, d, J 5.0, 2×H1), 4.57 (1H, dd, J 7.9 and 2.3, 2×H3), 4.50 (2H, s, 2×CH$_2$Ph), 4.30–4.27 (1H, m, 2×H2), 4.19 (1H, d, J 7.9, 2×H4), 4.01–3.98 (0.5H, m, H2'), 3.95–3.89 (1.5H, m, 2×H5+H2'), 3.71–3.64 (2H, m, 2×C6H$_a$H$_b$+2×H3'), 3.56–3.49 (2H, m, 2×C6'H$_2$), 3.28–3.18(1H, m, 2×C6H$_a$H$_b$), 3.24 (0.5H, br d, J 3.6, C3'OH), 3.21 (0.5H, br d, J 4.5, C3'OH), 1.85–1.45 (6H, m, 2×C2'NH$_2$+2×C4'H$_2$+2×C5'H$_2$), 1.45 (3H, s, acetonide Me), 1.44 (3H, s, acetonide Me), 1.32 (3H, s, acetonide Me), 1.29 (3H, s, acetonide Me): $^{13}$C nmr (63 MHz; CDCl$_3$) 174.71, 174.07, 138.22, 138.13, 128.33, 127.64, 109.35, 108.65, 96.27, 73.21, 72.90, 71.89, 71.62, 70.76, 70.46, 70.23, 66.18, 66.00, 58.79, 58.64, 39.66, 30.04, 29.86, 29.62, 26.36, 25.92, 25.71, 24.89, 24.24: High Resolution Mass Spectrum (Doped with CsI): Found M+H, 495.2727. C$_{25}$H$_{38}$N$_2$O$_8$ requires M+H, 495.2706: Found: C, 61.01; H, 8.02; N, 5.36. C$_{25}$H$_{38}$N$_2$O$_8$ requires C, 60.71; H, 7.74; N, 5.66.

Compound 67. Reaction with succinic anhydride

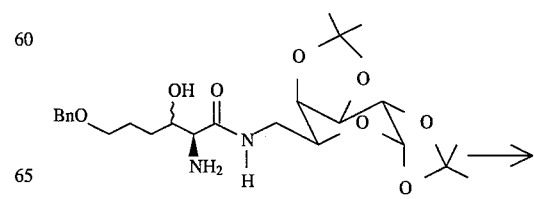

51
-continued

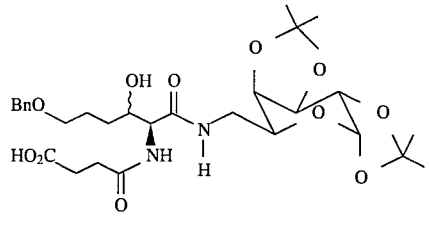

Succinic anhydride (6.0 mg, 60 μmol) was added to a stirred solution of amino glycopeptide 66 (27.7 mg, 56 μmol) in methanol (1 mL) at room temperature. After 1 hr, the solution was evaporated down under reduced pressure. The residual solid 67 was purified by flash chromatography (silica gel, using gradient elution 5AE10% acetic acid in ethyl acetate) to give (X) (29.4 mg, 85%) as a pale yellow gum. $R_f$ (10% acetic acid in ethyl acetate)). 0.49: IR (Film) cm-1 3303, 2980, 2935, 1644, 1558, 1436, 1382, 1255, 1211, 1167, 1109, 1070, 1006, 901: $^1$H nmr (400 MHz; CD$_3$OD) 7.32–7.23 (5H, m, aromatic), 5.44 (1H, d, J 5.0, 2×H1), 4.59 (1H, dd, J 7.9 and 2.1, 2×H3), 4.48 (2H, s, 2× $\underline{CH_2}$Ph), 4.38–4.34 (1H, m, 2×H'2), 4.31 (1H, dd, J 5.0 and 2.4, 2×H2), 4.21 (1H, d, J 7.9, 2×H4), 4.00–3.89 (1.5H, m, 2×H5+H3'), 3.84–3.76 (0.5H, m, H3'), 3.52–3.46 (3H, m, 2×C6$\underline{H_a}$H$_b$+2×C6H$_2$), 3.27–3.20 (1H, m, 2×C6H$_a$$\underline{H_b}$), 2.56–2.48 (4H, m, 2×C2"H$_2$+2×C3"H$_2$), 1.80–1.54 (4H, m, 2×C4'H$_2$+2×C5'H$_2$), 1.45 (3H, s, acetonide Me), 1.40 (3H, s, acetonide Me), 1.32 (3H, s, acetonide Me), 1.29 (3H, s, acetonide Me): $^{13}$C nmr (100 MHz; CD$_3$OD) 137.21, 126.78, 126.24, 126.03, 107.86, 107.34, 95.19, 71.24, 70.06, 69.56, 69.28, 69.24, 68.58, 64.68, 56.66, 38.02, 28.96, 28.35, 24.54, 23.83, 23.75, 22.62, 21.99: High Resolution Mass Spectrum (Doped with CsI): Found M+Cs, 727.1875. C$_{29}$H$_{42}$N$_2$O$_{11}$ requires M+Cs, 727.1843.

52
Compound 68. Removal of the protecting groups

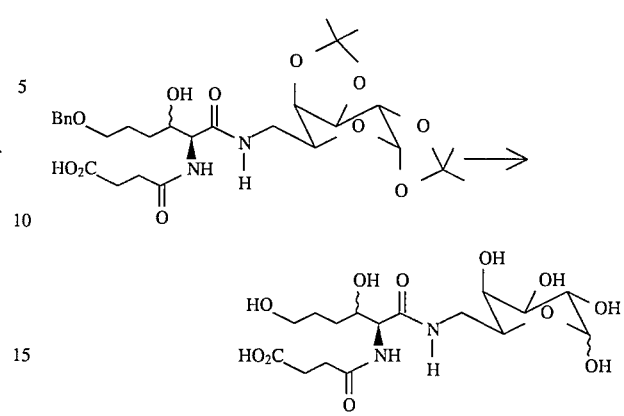

A solution of glycopeptide 67 (23.7 mg, 40 μmol) was stirred in 90% TFA in water (1 mL) at room temperature. After 3 hrs, the reaction solution was evaporated down under reduced pressure and azeotroped twice with toluene (2×5 mL). An nmr on the crude product was performed to ensure that the isopropylidene moieties were removed and then taken on to the next step without purification.

10% Palladium on carbon (50 mg) was added carefully to a stirred solution of crude glycopeptide in methanol (5 mL) and hydrogenated (1 atm) at room temperature. After 14 hrs, the 10% palladium on carbon was filtered through Celite® and the solid washed twice with methanol (2×5 mL). The combined filtrate and washings were evaporated down under reduced pressure. The crude product 68 was purified by Biogel P2 column and lyopholization of the fractions containing the compound gave (68) (14.6 mg, 86% over 2 steps) as a white solid: $R_f$(4:1:1 "BuOH:H$_2$O:HOAc) 0.29: $^1$H nmr (400 MHz; D$_2$O) (400 MHz; D$_2$O) 5.23 (d, J 3.7, H1$_\alpha$), 4.55 (dd, J 7.9 and 4.7, H1$_\beta$), 4.37–4.32 (m, H2'$_{(\alpha+\beta)}$), 4.15–4.05 (m, H5$_\alpha$+H3'$_\beta$),

SCHEME 10

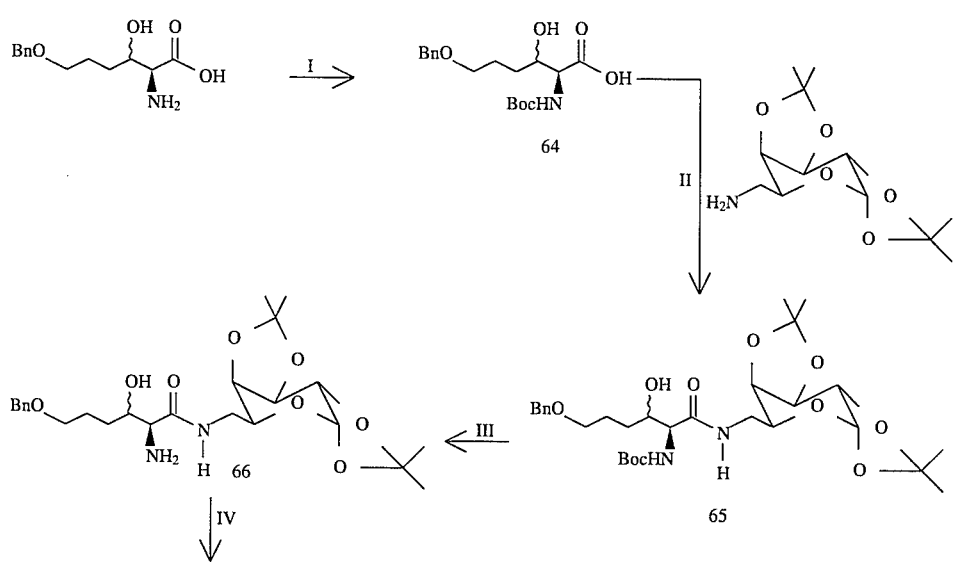

SCHEME 10 -continued

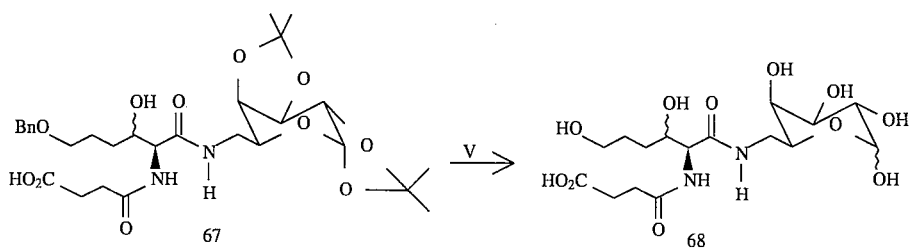

(I) di tert-butyl dicarbonate, triethylamine, 1,4-dioxane (84%);
(II) EDCI, 4-methyl morpholine, DMF (86%);
(iii) 15% TFA/DCM (86%);
(iv) succinic anhydride, methanol, (85%);
(v) 90% TFA/H$_2$O; workup then 10% palladium on carbon; methanol.

3.95–3.92 (m, H4$_\alpha$+H3'$_\alpha$), 3.86 (d, J 3.4, H4$_\beta$), 3.83 (dd, J 10.3 and 3.2 H3$_\alpha$), 3.78 (dd, J 10.3 and 3.7, H2$_\alpha$), 3.74–3.68 (m, H5$_\beta$), 3.64–3.61 (m, H3$_\beta$+C6'H$_2$($_\alpha+\beta$)), 3.55–3.44 (m, H2$_\beta$+C6H$_a$H$_{b(\alpha+\beta)}$), 3.42–3.31 (m, C6H$_a$H$_{b(\alpha+\beta)}$), 2.62–2.48 (m, C2"H$_2$($_\alpha+\beta$)+C3IH$_{2(\alpha+\beta)}$), 1.76–1.47 (m, C4'H$_2$($_\alpha+\beta$)+ C5'H$_{2(\alpha+\beta)}$); $^{13}$C nmr (100 MHz; D$_2$O) 182.93, 179.11, 175.20, 174.66, 98.86, 94.80, 75.19, 75.08, 75.02, 74.21, 72.91, 71.78, 71.48, 71.28, 71.18, 70.71, 70.52, 63.84, 63.80, 61.00, 60.90, 60.48, 42.15, 42.03, 34.71, 34.19, 34.12, 31.84, 31.44, 31.14: High Resolution Mass Spectrum (Doped with NaI): Found M+Na, 447.1570. C$_{16}$H$_{28}$N$_2$O$_{11}$ requires M+Na, 447.1591.

Compound 69

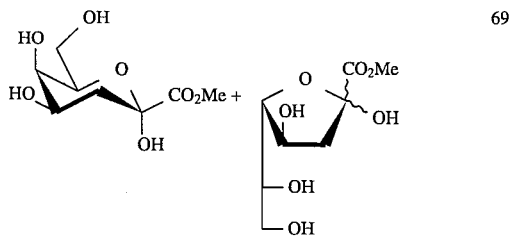

To a solution of D(–)threose (1.0 equivalents; Sigma chemical company) in 0.10 Molar potassium phosphate buffer at 37° C., is added 0.10 equivalents of sodium pyruvate and 1 unit of Neu5A (Neuraminidase; Sigma chemical company). The mixture is alowed to stir for 72 hours and then filtered and purified by reverse phase chromatography or HPLC (high performance liquid chromatography). The resulting 3:1 isomeric mixture is then resuspended in 0.10 Molar methanol and 1% Dowex 50W-X8 [H+; Aldrich chemical company] is added and allowed to stir for 12 hours at 25° C. The mixture is then filtered through a scinterred glass funnel to remove remaining Dowex ion exchange resin and condensed to provide a 49% overall yield (3:1 mixture for compound 69).

Compound 70

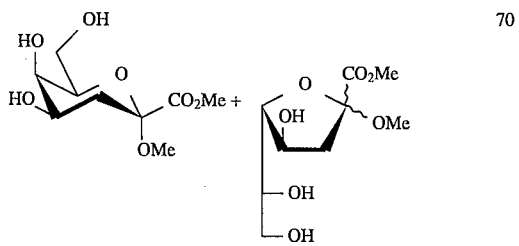

To a solution of compound 69 in methanol (0.10 molar) is added Dowex 50W-X8 [H+] and allowed to reflux for 2 hours. The mixture is then filtered and condensed to give compound 70 in a 60% yield.

Compound 71

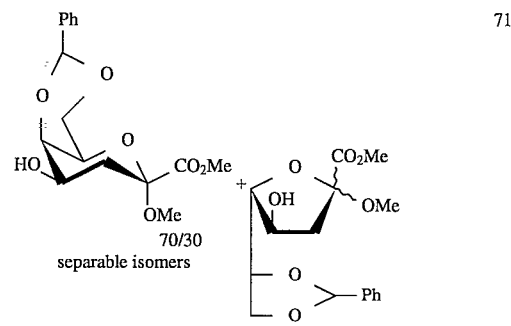

Compound 70 (1.0 equivalents)is then resuspended in DMF (dimethylformamide, 0.10 Molar) and 1.1 equivalents of benzaldehyde dimethyl acetal and 0.10 equivalents of camphorsulfonic acid is added and allowed to stir for 16 hours. The 70/30 mixture is then condensed and purified by flash chromatography to afford compound 71 in 72% overall yield as a single compound.

Compound 72

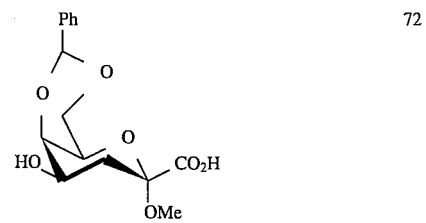

Compound 71 is dissolved in methanol/H$_2$O (2:1). LiOH.H$_2$O (0.10 equivalents) is added and the solution is stirred at room temperature for 2 hours. Methanol is evaporated and the remaining aqueous solution is acidified to pH 4 by 1N HCl and extracted with ethyl ether. The organic fractions are combined and dried over MgSO$_4$. Evaporation of the solvent affords 72 (68%, one single isomer).

SCHEME 11

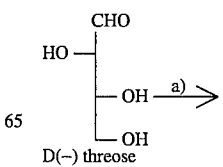

SCHEME 11 -continued

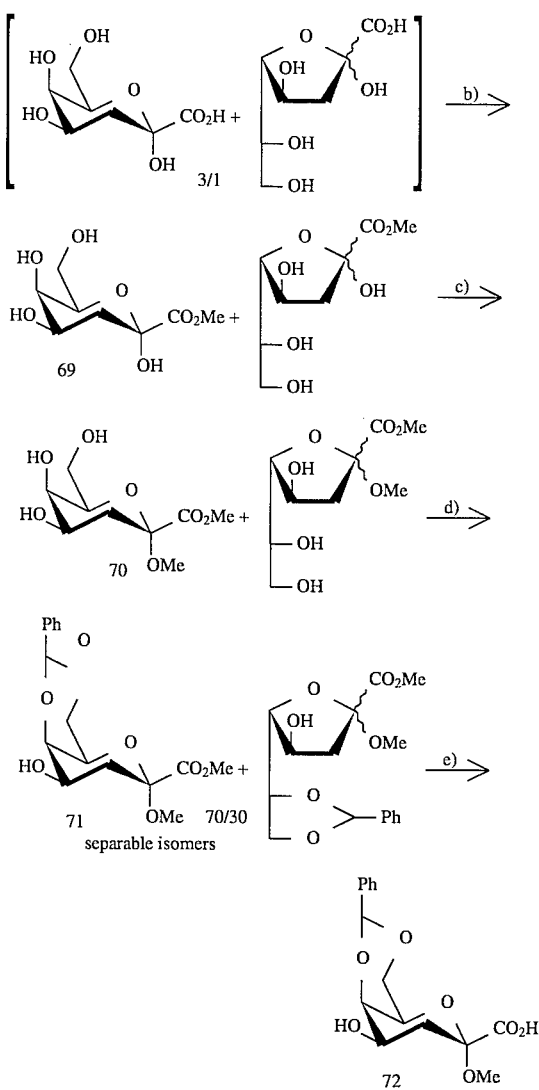

Reagents and conditions:
(a) Sodium pyruvate, Neu5A., Potassium phosphate buffer, 37°C., 72h;
(b) MeOH, Dowex 50W-X8 [H⁺], 25°C.,12h, 49% for 2 steps;
(c) MeOH, Dowex 50W-X8 [H⁺], reflux, 2h, 60%;
(d) benzaldehyde dimethyl acetal, CSA DMF 60°C., 16h, 72%;
(e) LiOH, MeOH, 25°C., 2h, 68%.

Compound 73

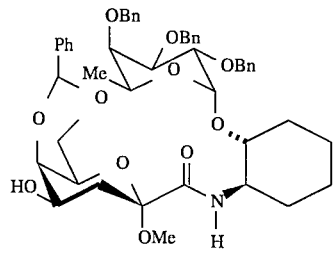

Compound 16 (1.0 equivalents), EDAC (1-ethyl-3-(3-dimethylaminopropyl)-carbodiimide; Sigma company; 1.5 equivalents) and HOBT (1-hydroxybenzotriazole hydrate; Aldrich company; 1.5 equivalents) was dissolved in dry dimethylformamide (0.10 Molar) and compound 72 (1.2 equivalents) was added. The mixture was stirred at −20° C. and gradually warmed to room temperature and stirred for a total of 12 hours. The organic layer was diluted with dichloromethane, washed with water twice and dried over MgSO₄. Silica gel chromatography afforded compound 73 (58% yield).

Compound 74

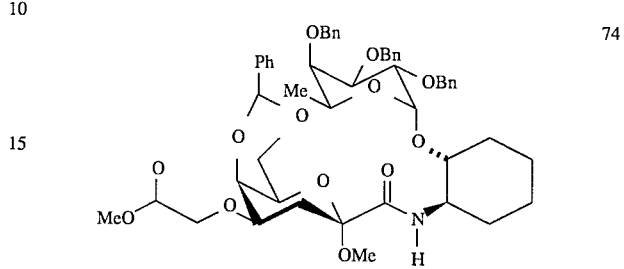

To a solution of compound 73 in 0.10 Molar dimethylformamide is added 1.1 equivalents of methylbromacetate, 1.1 equivalents sodium hydride, and 0.10 equivalents tetrabutylammonium iodide (Aldrich chemical) and allowed to stir for 4 hours at 25° C. The mixture is then diluted with methylene chloride, quenched with water, washed with sodium bicarbonate, water, brine and dried over magnesium sulfate. The mixture is condensed and purifed by flash chromatography to give compound 74 in 53% yield.

Compound 75

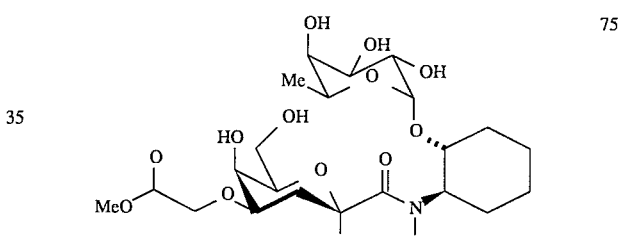

Compound 74 (1.0 equivalents) was dissolved in methanol (0.10 Molar) and Pd(OH)₂ on carbon (wet, Degussa type E101 NE/W, 0.10 equivalents; Aldrich company) was added. The mixture was stirred under hydrogen (1 atm) at room temperature for 12 h. The catalyst was filtered through celite and the filtrate was evaporated to afford 75 in 90% overall yield.

Compound 76

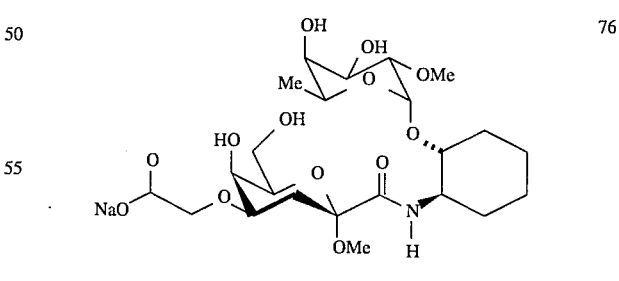

MPH II 74

To a solution of compound 75 in methanol (0.10 Molar) is added 0.10 Molar NaOH and allowed to stir for 4 hours at room temperature. The solvent was next removed invacuo, and the compound 76 was further purified by recrystallization or flash chromatography using a polar solvent such as ethylacetate, methanol: ethylacetate, etc. to give a 70% yield of compound 76.
SCHEME 12
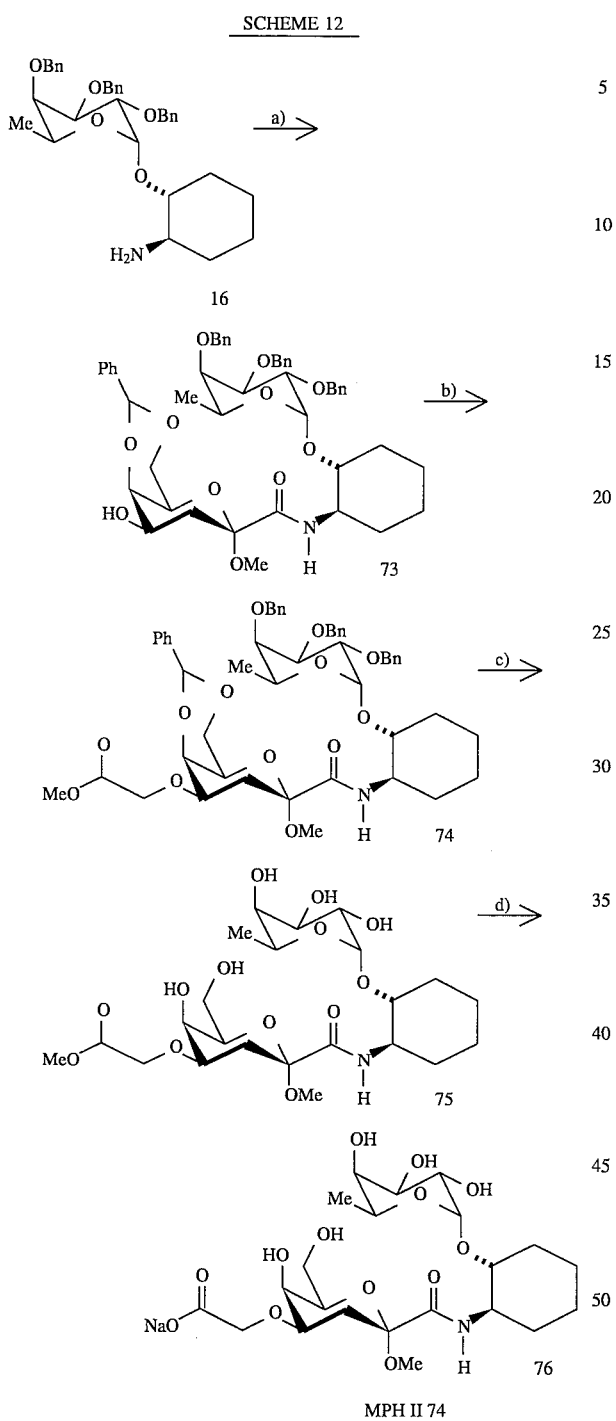
Reagents and conditions:
(a) Acid 72, HOBt, NMM, EDCI, DMF, −20°C. ⟶ r.t., 12h, 58%;
(b) Methylbromoacetate, NaH, NBu₄I, DMF, 4h, 53%;
(c) H₂, Pd(OH)₂, MeOH, 12h, 90%;
(d) NaOH, 0.1 N, 4h, 70%.
What is claimed is:
1. A compound of the formula:
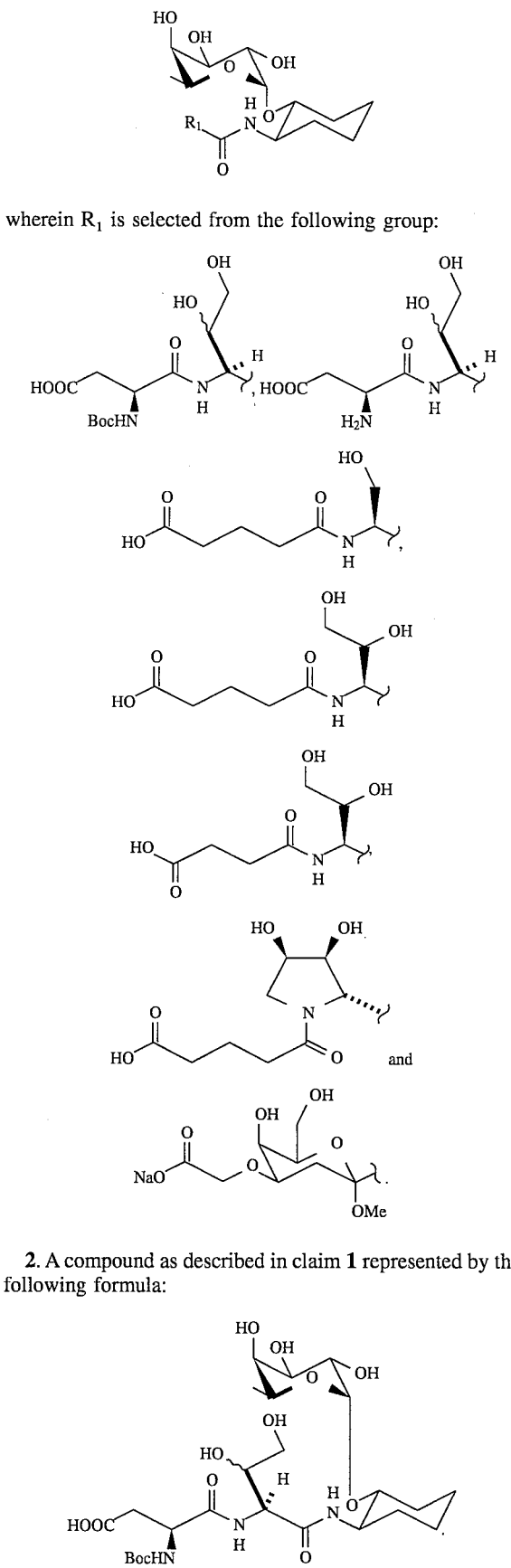
wherein $R_1$ is selected from the following group:
2. A compound as described in claim 1 represented by the following formula:

3. A compound as described in claim 1 represented by the following formula:

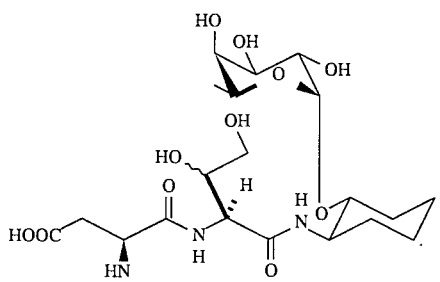

4. A compound as described in claim 1 represented by the following formula:

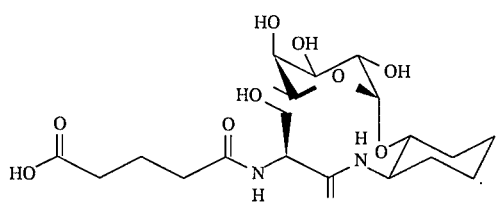

5. A compound as described in claim 1 represented by the following formula:

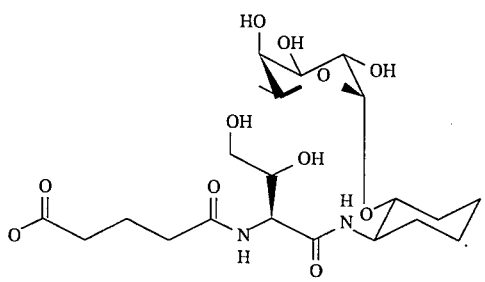

6. A compound as described in claim 1 represented by the following formula:

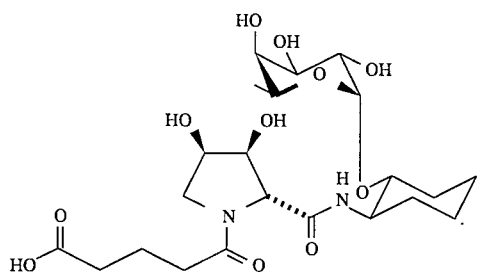

7. A compound as described in claim 1 represented by the following formula:

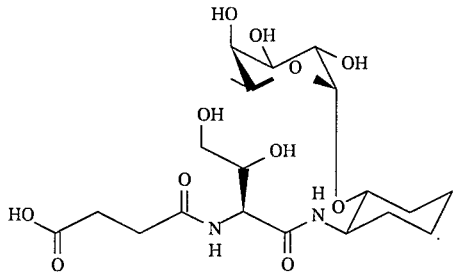

8. A compound as described in claim 1 represented by the following formula:

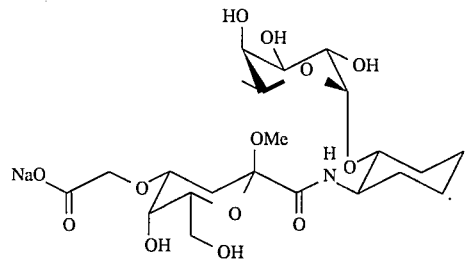

9. A compound as described in claim 7 with a (2S,3R) isomeric structure.

10. A compound as described in claim 7 with a (2S,3S) isomeric structure.

11. A compound of the formula:

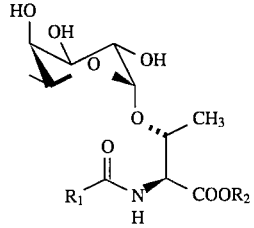

wherein $R_2$ is selected from the group consisting of hydrogen and C1–C6 alkyl groups and $R_1$ is selected from the following group:

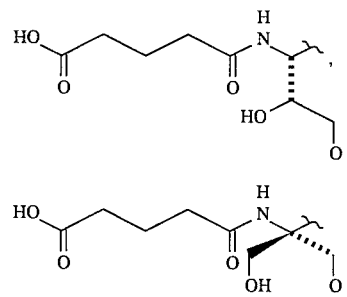

-continued

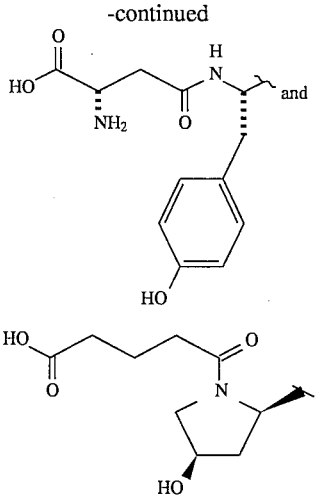
and

12. A compound as described in claim 11 represented by the following formula:

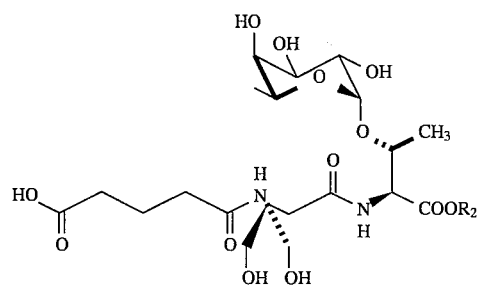

wherein $R_2$ is selected from the group consisting of hydrogen and C1–C6 alkyl groups.

13. A compound as described in claim 11 represented by the following formula:

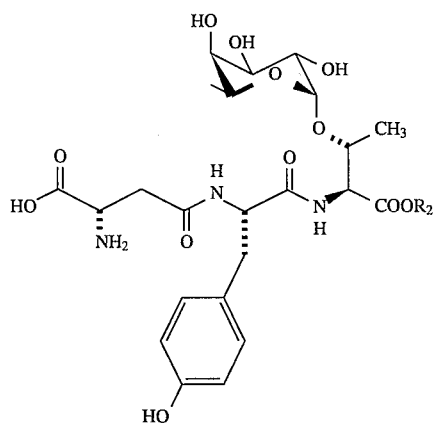

wherein $R_2$ is selected from the group consisting of hydrogen and C1–C6 alkyl groups.

14. A compound as described in claim 11 represented by the following formula:

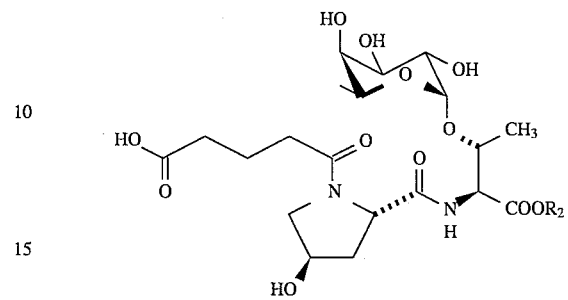

wherein $R_2$ is selected from the group consisting of hydrogen and C1–C6 alkyl groups.

15. A compound as described in claim 11 represented by the following formula:

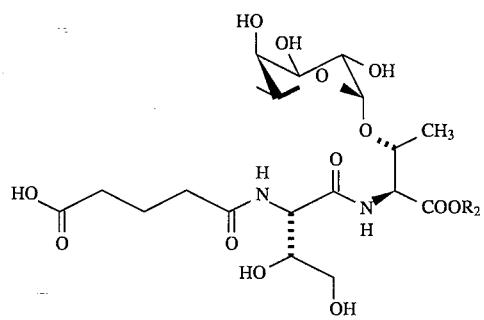

wherein $R_2$ is selected from the group consisting of hydrogen and C1–C6 alkyl groups.

16. A compound as described in claim 14 wherein $R_2$ is hydrogen.

17. A compound as described in claim 14 wherein $R_2$ is an ethyl group.

18. A compound represented by the following formula:

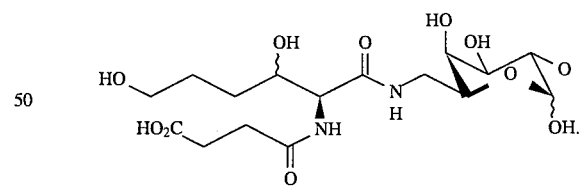

* * * * *